(12) United States Patent
Heber-Katz

(10) Patent No.: US 6,538,173 B2
(45) Date of Patent: Mar. 25, 2003

(54) COMPOSITIONS AND METHODS FOR WOUND HEALING

(75) Inventor: Ellen Heber-Katz, Philadelphia, PA (US)

(73) Assignee: The Wistar Institute, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/249,155

(22) Filed: Feb. 12, 1999

(65) Prior Publication Data

US 2003/0037345 A1 Feb. 20, 2003

Related U.S. Application Data

(60) Provisional application No. 60/074,737, filed on Feb. 13, 1998, provisional application No. 60/097,937, filed on Aug. 26, 1998, and provisional application No. 60/102,051, filed on Sep. 28, 1998.

(51) Int. Cl.[7] .................... A01K 67/00; A61K 49/00; C12Q 1/00; C12Q 1/68; G01N 33/00
(52) U.S. Cl. ................ 800/8; 800/3; 424/9.1; 435/4; 435/6
(58) Field of Search ................ 424/9.1; 435/4, 435/6; 800/3, 8

(56) References Cited

FOREIGN PATENT DOCUMENTS

WO          97 33980 A        9/1997

OTHER PUBLICATIONS

Lander & Kruglyak "Genetic Dissection of Complex Traits: Guidelines for Interpreting and Reporting Linkage Results" Nature Genetics, vol. 11, Nov. 1995, pp. 241–247.

Yu et al. "Differential Gene Expression in Healing Rat Corneal Epithelium" Investigative Ophthalmology and Visual Science, vol. 36, No. 10, 1995 pp. 1997–2007.

Fassler et al. "Differential Regulation of Fibulin, Tenascin–C, and Nidogen Expression During Wound Healing of Normal and Glucoccorticoid–Treated Mice" Experimental Cell Research, vol. 222, 1996, pp. 111–116.

Hirobe "Genetic Factors Controlling the Proliferative Activity of Mouse Epidermal Melanocytes During the Healing of Skin Wounds" Genetics, vol. 120, 1988 pp. 551–558.

Dietrich et al. "A Genetic Map of the Mouse with 4,006 Simple Sequence Length Polymorphisms" Nature Genetics, vol. 7, 1994, pp. 220–224.

Hubner et al. "Differential Regulation of Pro–Inflammatory Cytokines During Wound Healing in Normal and Glucocorticoid–Treated Mice" Cytokine, vol. 8, No. 7, 1996, pp. 548–556.

Heber–Katz, Ellen, Abstract of NIH Grant No. 1 RO1 AI42395–01, obtained from the CRISP database available at <http://www.nih.gov>; Letter from Dorrette M. Finch, Director of Division of Research Documentation at NIH, stating that the abstract of NIH Grant No. 1 RO1 AI42395–01 was posted on the CRISP system on May 1, 1998.

McBrearty et al. "Genetic analysis of a mammalian wound––healing trait" Proc. Natl. Acad. Sci, USA vol. 95, pp. 11792–11797, Sep. 1998.

Clark et al. "A New Murine Model for Mammalian Wound Repair and Regeneration" Clinical Immunology and Immunopathology, vol. 88, No. 1, Jul. pp. 35–45, 1998.

Goss and Grimes "Epidermal Downgrowths in Regenerating Rabbit Ear Holes" J. Morph., 146: 533–542 (1975).

*Primary Examiner*—Annie-Marie Baker
(74) *Attorney, Agent, or Firm*—Banner & Witcoff, Ltd.

(57) ABSTRACT

Mice in which enhance wound healing occurs can be used to identify genes and gene products which are involved in enhanced wound healing in mammals, including humans.

Methods and compositions for treating wounds, including central and peripheral nerve wounds, are also provided.

20 Claims, 32 Drawing Sheets

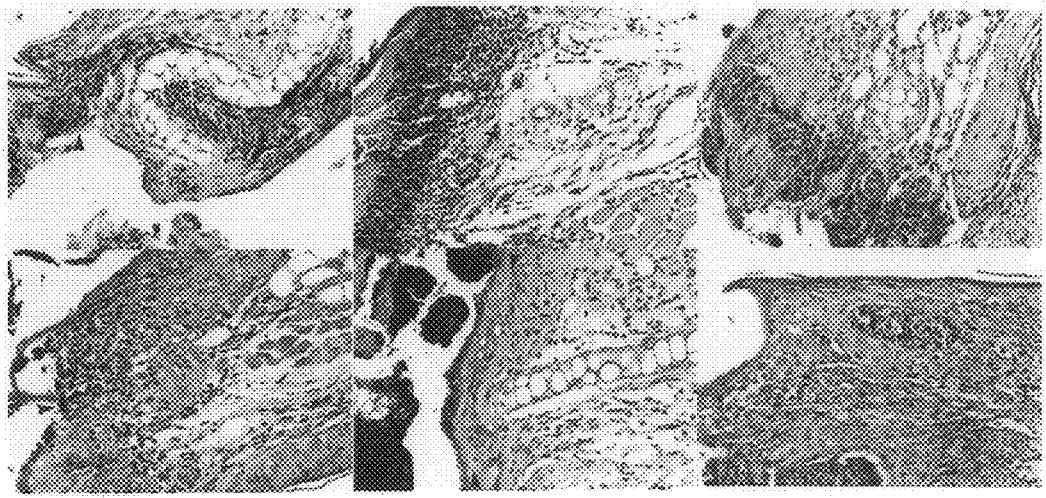

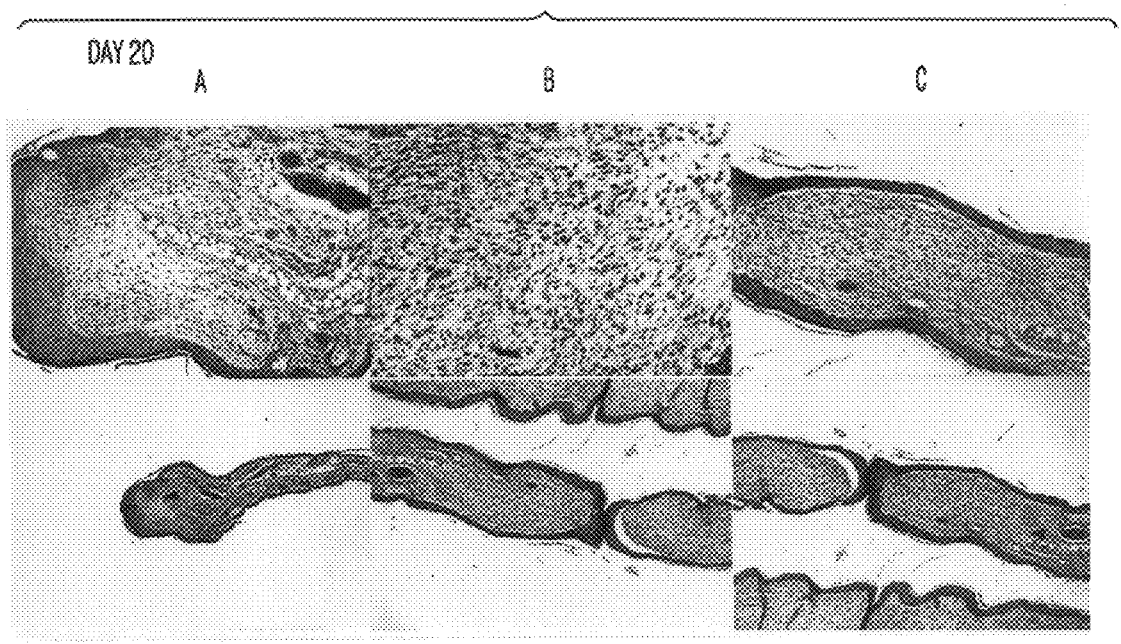

DAY 81

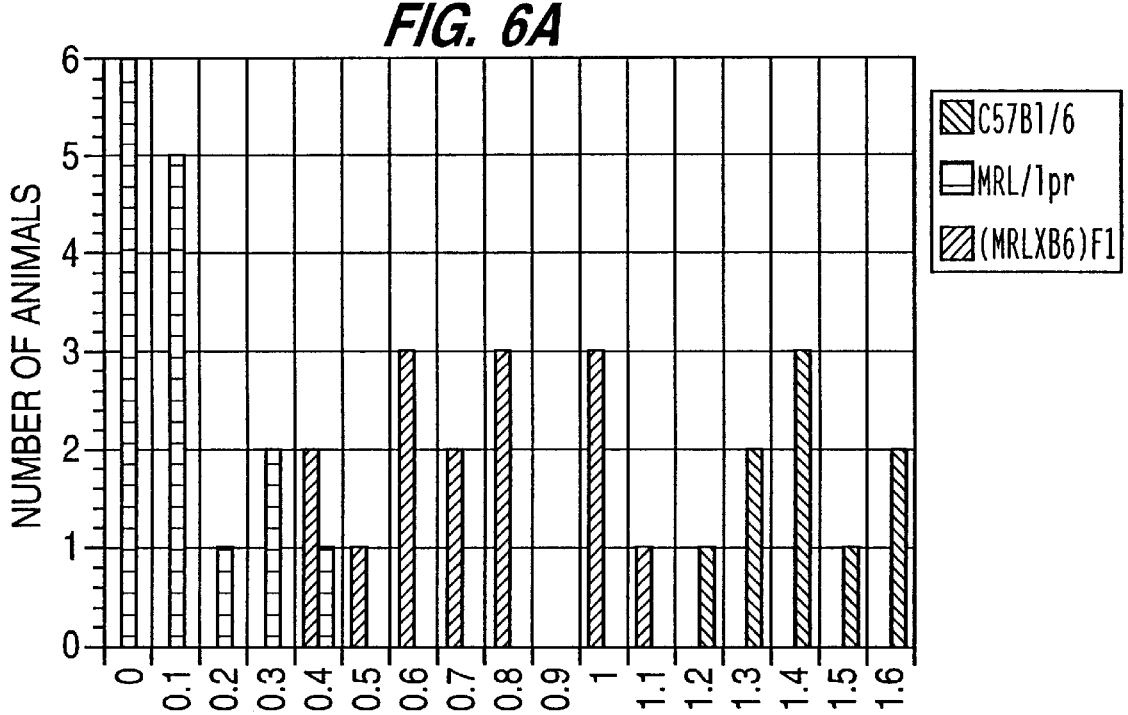
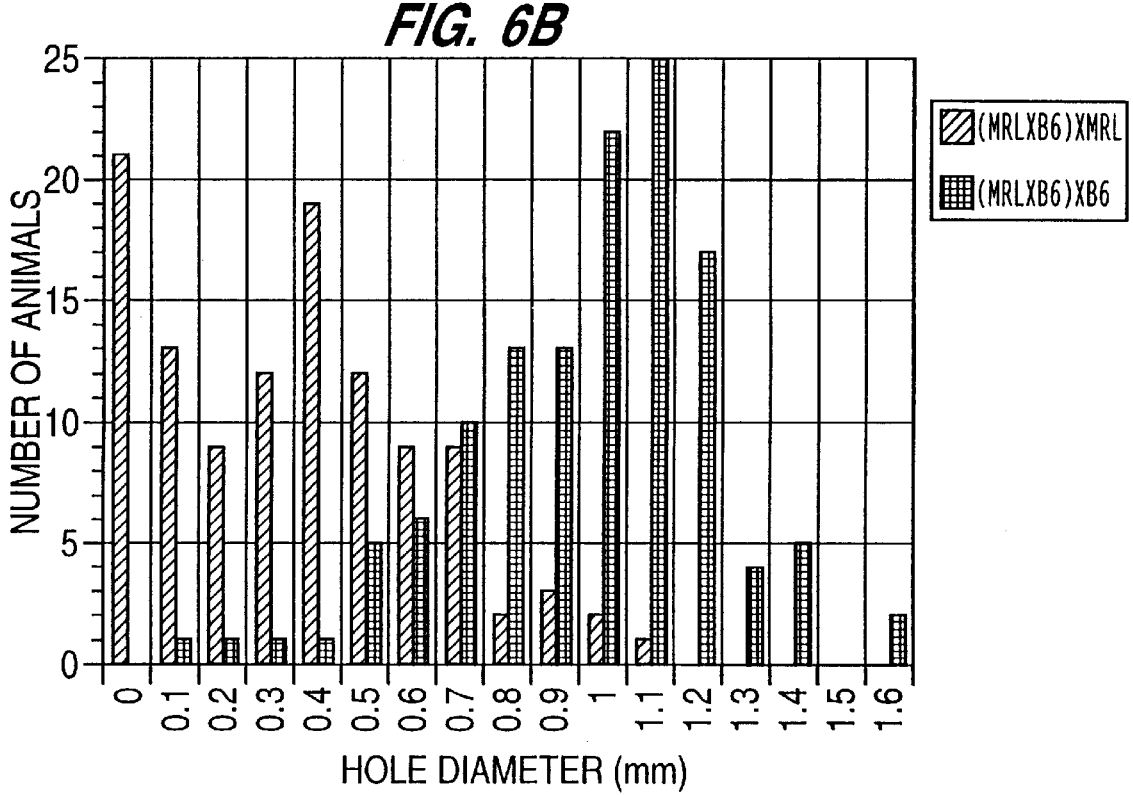

← EYE    BRAIN →

← EYE   NERVE FIBERS   OLIGODENDROCYTES   BRAIN →

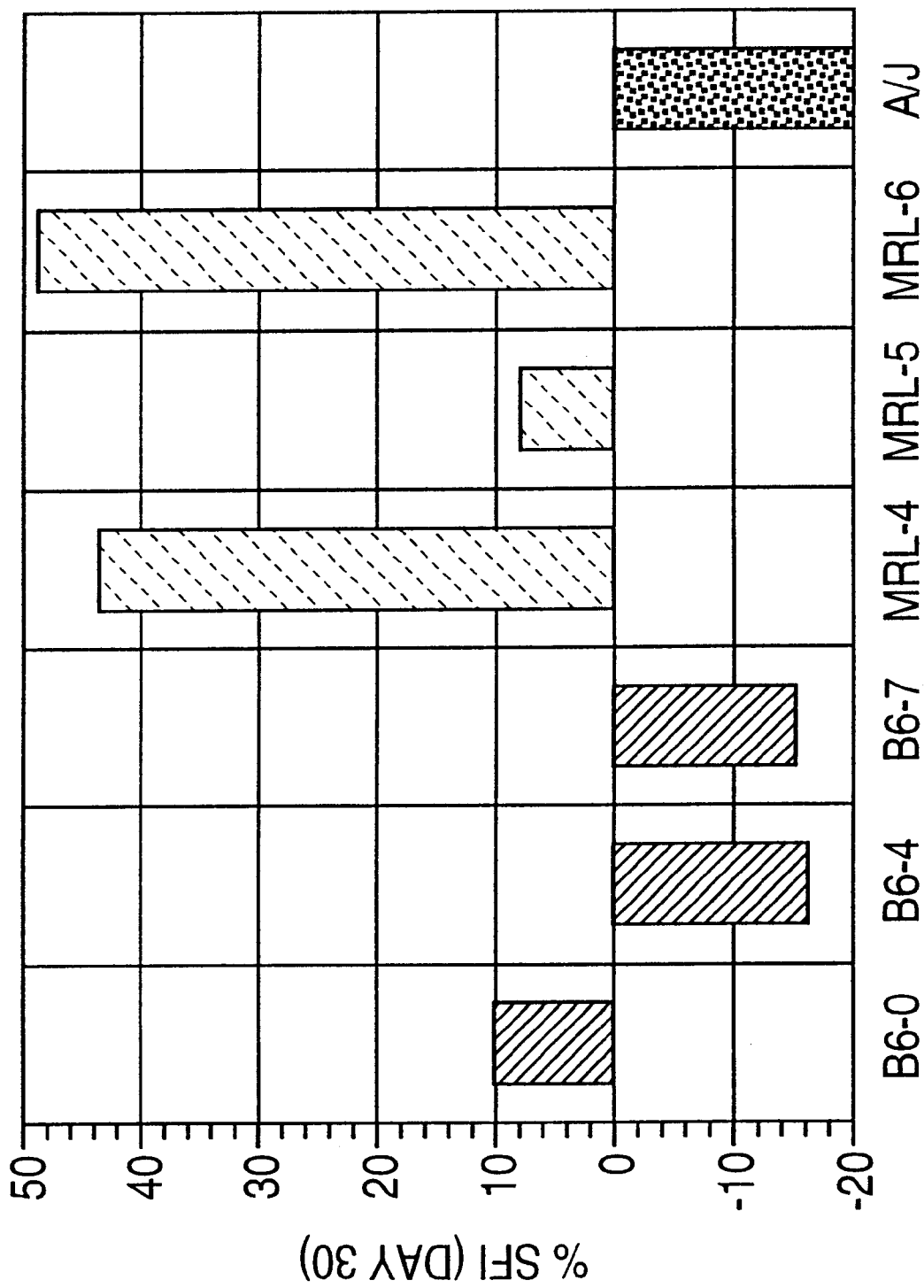

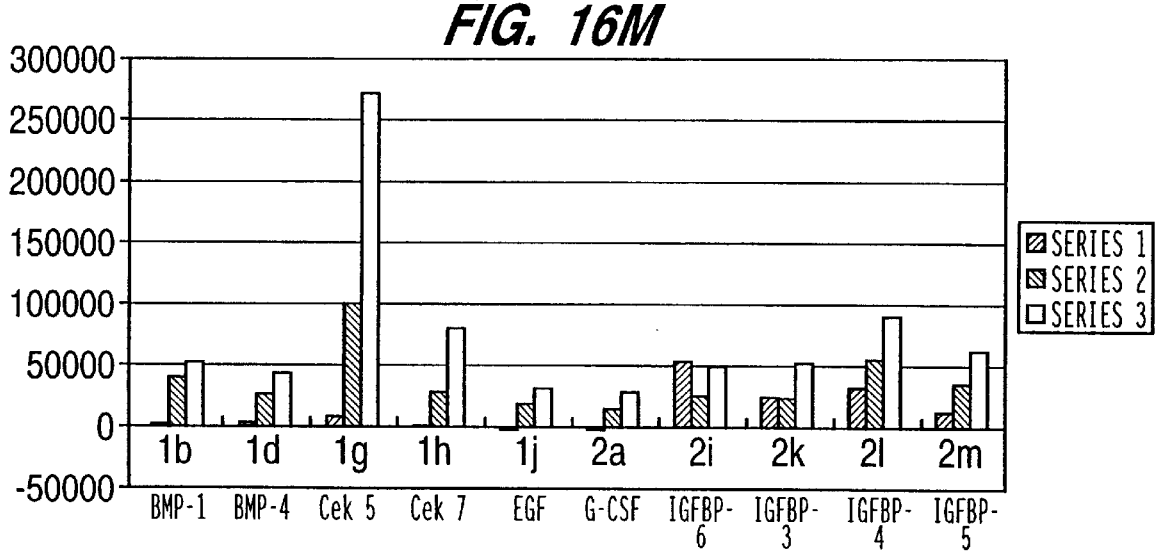
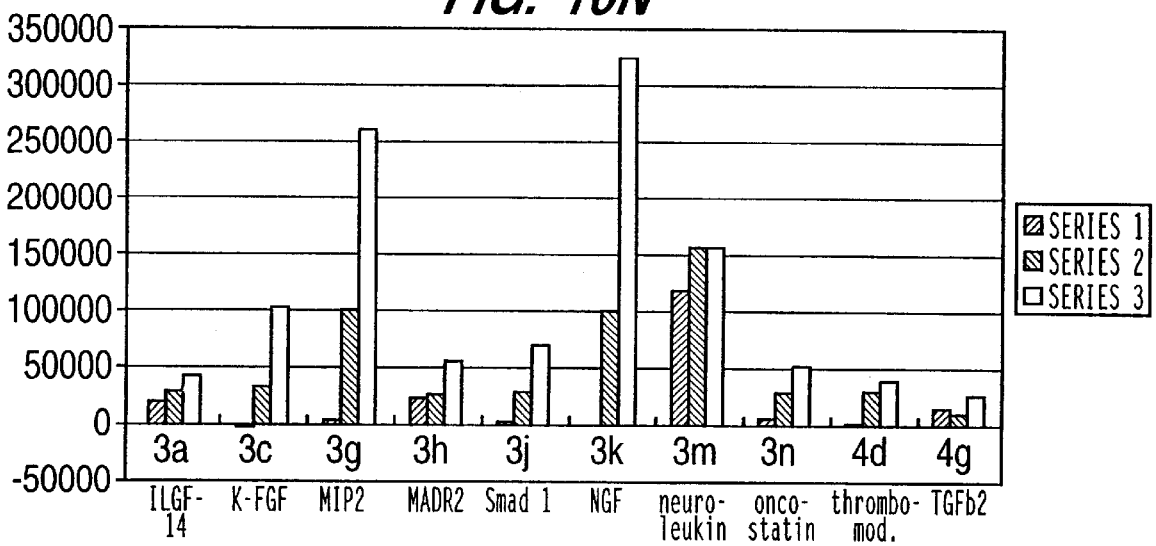
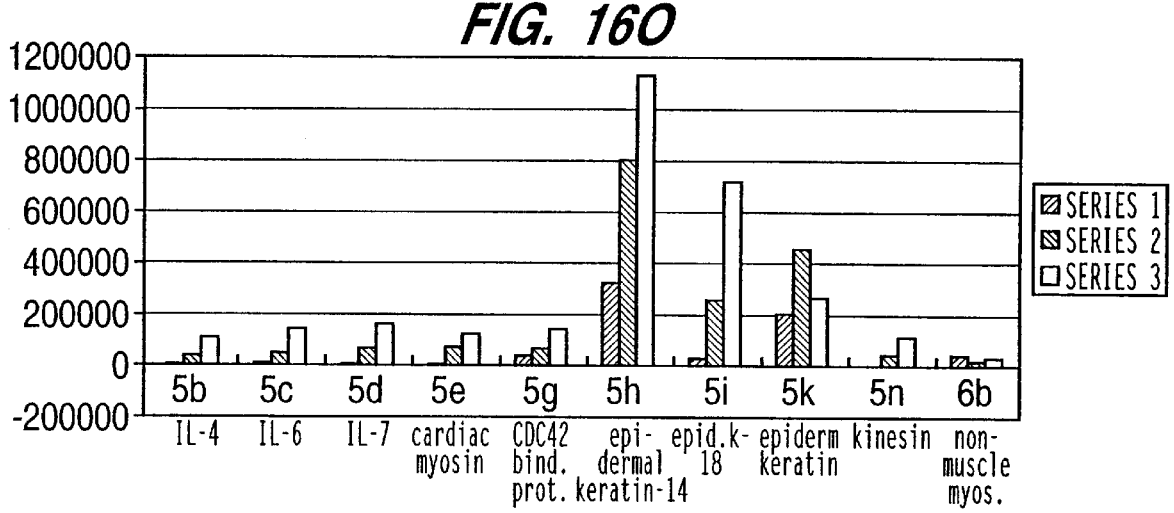

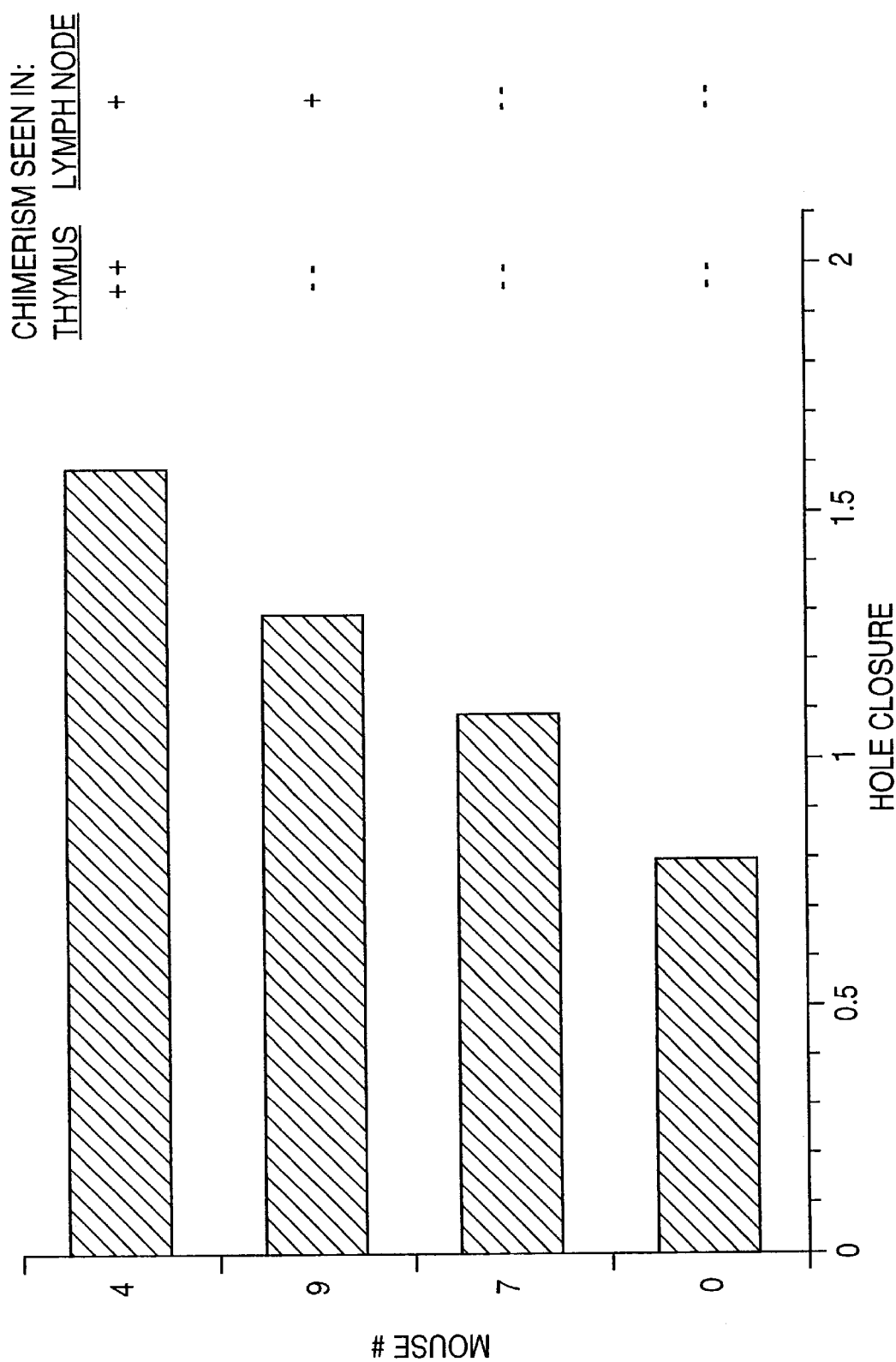

HEALER

NON-HEALER

COMPOSITIONS AND METHODS FOR WOUND HEALING

This application claims the benefit of co-pending provisional applications Serial No. 60/074,737 filed Feb. 13, 1998, Ser. No. 60/097,937 filed Aug. 26, 1998, and Ser. No. 60/102,051 filed Sep. 28, 1998, which are incorporated herein by reference.

This work was partially supported by the U.S. Government under USPHS grant AI42395 awarded by the National Institutes of Health. The U.S. Government retains certain rights in this invention.

TECHNICAL FIELD OF THE INVENTION

This invention is related to the field of wound healing. More particularly, the invention is related to methods and compositions for enhancing wound healing in mammals.

BACKGROUND OF THE INVENTION

The biological response to tissue injury in higher organisms falls into two main categories: wound repair and regeneration (1). In amphibians, the form of wound healing seen is often epimorphic regeneration, where entire limbs can be reformed after amputation (1). In adult mammals, wound healing can involve wound repair or tissue regeneration, including the replacement of mature cells through cell proliferation (7) or replenishment of cells, but not organs, from immature stem cells (9, 11, 25). Complete wound healing, however, with perfect replacement of tissue and function, is typically not observed. Injuries to the central and peripheral nervous system, including optic nerve and spinal cord injuries, are especially refractory to healing. Thus, there is a need in the art for methods and compositions for enhancing wound healing in mammals.

SUMMARY OF THE INVENTION

It is an object of the invention to provide methods and compositions for use in healing wounds. These and other objects of the invention are provided by one or more of the embodiments described below.

One embodiment of the invention is a method of identifying a gene involved in enhanced wound healing. DNA microsatellite markers which can distinguish a first and a second mouse strain are identified. The first mouse strain is a healer mouse strain, and the second mouse strain is not a healer mouse strain. Microsatellite markers which segregate with enhanced wound healing in progeny of the first and second mouse strains are identified. A chromosomal locus which contains at least one gene involved in enhanced wound healing is thereby identified.

Still another embodiment of the invention is a method of treating a wound in a mammal. A reagent which specifically binds to an expression product of a gene whose expression is decreased in a healer mouse relative to a non-healer mouse is administered to a mammal with a wound. Expression of the gene is thereby decreased.

Even another embodiment of the invention is a method of treating a wound in a mammal. An expression product of a gene whose expression is increased after wounding in a healer mouse relative to expression of the gene after wounding in a non-healer mouse is administered to a mammal with a wound. The level of the expression product in the wound is thereby increased.

Yet another embodiment of the invention is a method of restoring function after nerve injury in a mammal. A reagent which specifically binds to an expression product of a gene whose expression is decreased after wounding in a healer mouse relative to expression of the gene after wounding in a non-healer mouse is administered to a mammal with a nerve injury. Expression of the gene is thereby decreased.

Another embodiment of the invention is a method of restoring function after nerve injury in a mammal. An expression product of a gene whose expression is increased after wounding in a healer mouse relative to expression of the gene after wounding in a non-healer mouse is administered to a mammal with a nerve injury. The level of the expression product in the wound is thereby increased.

Still another embodiment of the invention is a method of treating a wound in a mammal. A cell or cellular extract obtained from a healer mouse is administered to a mammal with a wound. Healing of the wound in the mammal is thereby enhanced.

Yet another embodiment of the invention is a method of treating a wound in a mammal. A cell in which expression of a wound healing gene has been altered is administered to a mammal with a wound. Healing of the wound in the mammal is thereby enhanced.

Even another embodiment of the invention is a healer mouse having at least one quantitative trait locus selected from the group consisting of the quantitative trait loci shown in Tables 2, 9 and 16. The healer mouse exhibits an enhanced healing response to a wound compared to a mouse which does not have the at least one chromosomal locus. The healer mouse is not an MRL mouse.

Yet another embodiment of the invention is a preparation comprising a fraction of an extract of a tissue of a healer mouse. The preparation alters a biological property of a model of wound healing.

Still another embodiment of the invention is a preparation comprising cells of a healer mouse. The preparation alters a biological property of a model of wound healing.

Another embodiment of the invention is a method of identifying a factor involved in enhanced wound healing. A model of wound healing is contacted with a preparation selected from the group consisting of serum, a fraction of serum, an extract of at least one healer mouse tissue, and a fraction of an extract of at least one healer mouse tissue. A property of the model of wound healing is assayed. A preparation which alters the property of the model of wound healing is identified as comprising a factor involved in enhanced wound healing.

Yet another embodiment of the invention is a method of screening test compounds for the ability to enhance wound healing. A healer model of wound healing is contacted with a test compound. The healer model comprises cells of a healer mouse. The effect of the test compound on a biological property associated with wound healing is measured in the healer model. A test compound which enhances the biological property of the healer model is identified as a potential factor for enhancing wound healing.

The present invention thus provides the art with a mammalian model of enhanced wound healing. The healer mouse described herein can be used, inter alia, to identify genes and gene products involved in enhanced wound healing and to provide methods and compositions for healing wounds, particularly wounds of the nervous system, in mammals.

BRIEF DESCRIPTION OF THE DRAWINGS

FIGS. 3A–3F. Histological examination of early events in ear hole closure. The first two days after wounding of C57BL/6 ears (FIGS. 3A and 3D) and MRL/+ (FIGS. 3B and 3E) and MRL/lpr ears (FIGS. 3C and 3F) were examined. Day 1: these sections show more swelling at the wound site for the MRL tissue (smaller arrows). Eschar and inflammatory cellular infiltrate at the wound margin is similar for both strains and re-epithelialization is not seen (larger arrows). Day 2: The C57BL/6 wound is partially covered (arrow) by eschar with migrating epithelium not yet covering the wound (9 out of 14 edges examined did not close) while the MRL wound is completely covered (arrows) with epithelium (10 out of 14 edges examined completely closed). Magnification=40x; tissue is stained with hematoxylin and eosin.

FIG. 4. Day 5, 10, and 20 wounds. For all days indicated for C57BL/6 tissue (A), MRL/+ tissue (B) and MRL/lpr tissue (C). All sections are stained with hematoxylin and eosin (pictures are representative of 4 edges examined). FIG. 4C, Panels A–C. Day 20 (A, C:20x; B:40x-upper panels and 5x-lower panels): The prominent proliferation of fibroblasts in the dermis and the appearance of a blastema-like structure has led to significant closure of the MRL wound as originally marked by the cut edges of cartilage at the right and left margins of the photograph (5x-between arrows). By comparison, there is little extension of C57BL/6 tissue into the wound space. The homogeneity of fibroblast proliferation and ECM deposition is most striking in MRL (B:40x-upper panel).

FIG. 6. The analysis of frequencies of wound closure on day 30 in parental and crossbred populations. Histograms of day 30 ear punch hole diameters can be seen for the following genotypes: C57BL/6 and MRL/lpr parental mice and $F_1$ mice (upper panel) and the first backcross to each parental strain (lower panel).

FIG. 9. Healer and non-healer mice 1.5 months after transection of the left optic nerve.

FIG. 12.

FIG. 13. Graph depicting nerve regeneration in various strains of mice. SFI, Sensory Function Index.

FIG. 20. Bar graph showing that adoptive transfer of fetal liver into X-irradiated non-healer recipients enhances wound healing.

FIG. 21. Two-day old explant cultures of punched ears of healer and non-healer mice.

DETAILED DESCRIPTION

Figure 1:
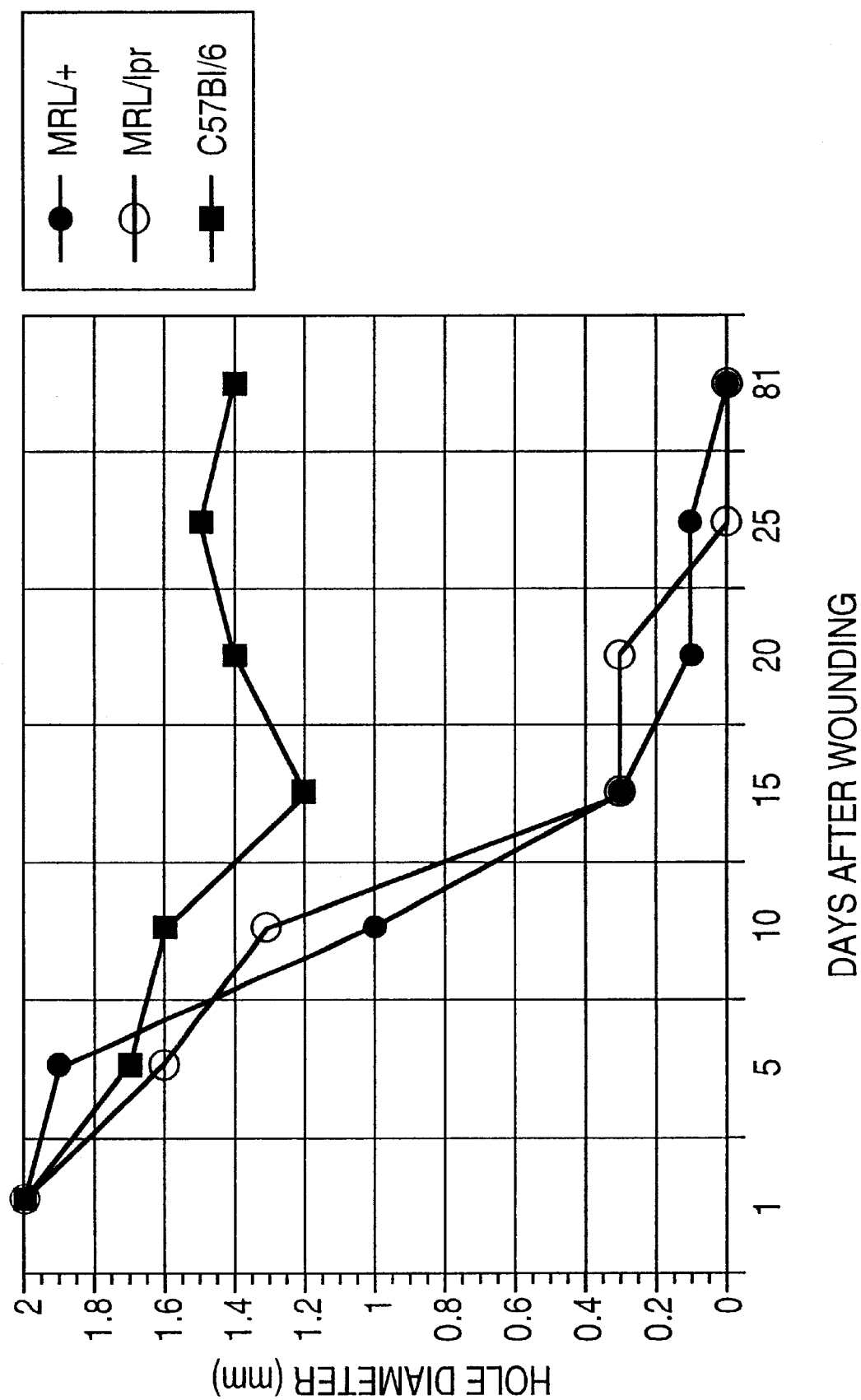
FIG. 1. The kinetics of ear punch hole closure. Two mm holes were punched in ears on day 0 and, for each strain of mouse, holes were measured at days indicated on the horizontal axis. Average hole diameters are shown (n=4).
Figures 2A, 2E:
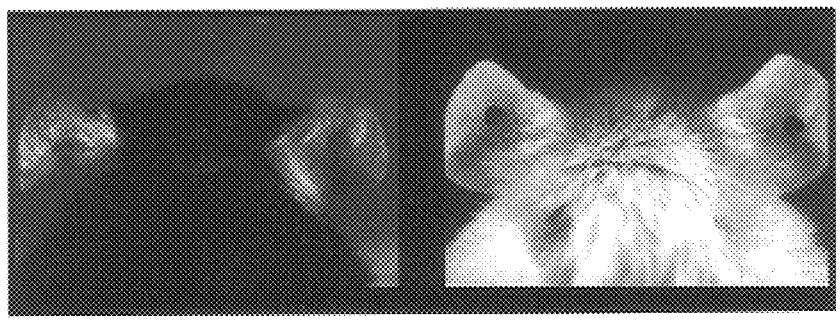
FIGS. 2A–2H. Photographs of the healing ear wounds. C57BL/6 (left side) and MRL/lpr (right side) ears were punched bilaterally in the center of the ears creating a 2 mm through-and-through wound and followed for 33 days. The ear holes of the C57BL/6 mouse remained open 1 day (FIG. 2A), 9 days (FIG. 2B), 20 days (FIG. 2C), and 33 days (FIG. 2D) after punching. In the MRL/lpr mouse, one can see the progression of hole closure from day 1 (FIG. 2E), day 9 (FIG. 2F), day 20 (FIG. 2G), to day 33 (FIG. 2H).
Figures 2B, 2F:
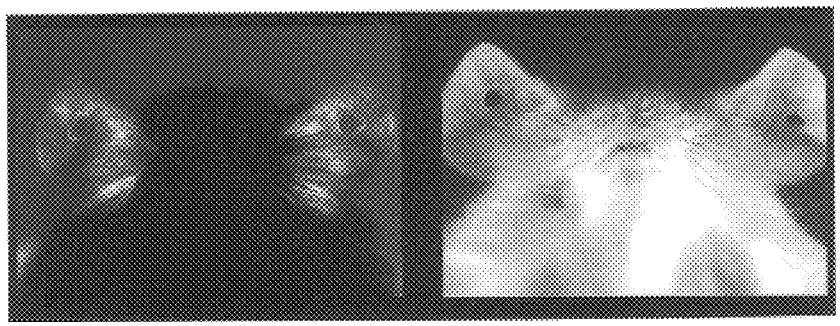
Figures 2C, 2G:
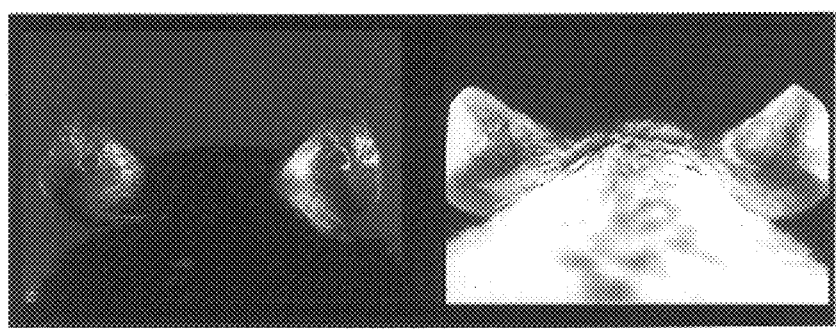
Figures 2D, 2H:
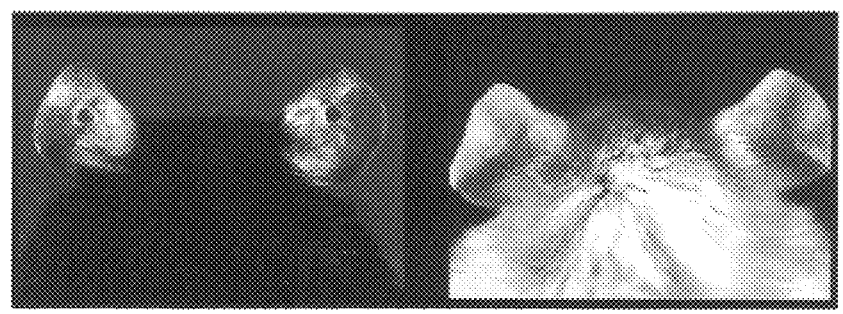

It is a discovery of the present invention that healer mice, including MRL mice and strains derived from MRL mice, can be used as murine models of wound healing, particularly of the central and peripheral nervous system. These models are useful for identifying genes and gene products which are involved in enhanced wound healing in mammals, including humans, as well as for developing therapeutic compounds and methods to enhance wound healing.

Healer Mice

Typically, holes punched in the ears of non-healer mice are permanent and exhibit at most about 25% closure even 60 days after punching. Patterns of such holes can thus be used to distinguish individual non-healer mice from one another, which is a standard laboratory method for animal identification. In contrast, a hole punched in the ear of a healer mouse will close at least 70%, more preferably at least 80% or 90%, within 60 days, more preferably within 45 or 30 days. Most preferably, an ear hole of a healer mouse closes completely.

The percent closure of a hole punched in the ear of a mouse can be determined by measuring the initial diameter of the hole and by taking subsequent measurements during the first thirty days after punching. Typically, a 2 mm hole is punched. In particularly preferred healer mouse strains, complete ear hole closure occurs 30 days after punching, without scar tissue and with regeneration (perfect replacement) of cell types initially present in the ear, such as cartilage, dermis, epidermis, and blood vessels.

The healing capacity of a mouse strain can easily be tested by an ear punch assay, as described above. However, healing capacity can be assessed following other types of wounds in the mouse, including, but not limited to, digit cutting, tail cutting, and cutting or crushing of a nerve, particularly an optic or sciatic nerve, or a partial or complete cutting or crushing of the spinal cord. Liver regeneration can also be measured.

In addition to ear hole closure as described above, a mouse strain with a healer phenotype, in contrast to a non-healer mouse, may also exhibit one or more of the following characteristics. All such aspects of the healer phenotype, including enhanced tissue regeneration, are components of enhanced wound healing. Blastemas may form in the vicinity of a cut in the ear, digits, tail, or liver in a strain of healer mouse. Following injury to the liver, a strain of healer mouse may exhibit rapid replacement of liver mass and homeostasis. A healer mouse strain may exhibit breakdown in the extracellular matrix-basement membrane to allow epithelial-mesodermal interaction and may express forms of extracellular matrix-basement membrane components, such as tenascin, which are typically expressed only during development or regeneration. Organ regeneration can also occur.

Healer mouse strains may also exhibit rapid recovery from central or peripheral nerve damage, such as sciatic or optic nerve crush, or cutting or crushing of the spinal cord, and can thus be used as models in which to study regeneration of injured nerves. Nerve regeneration can be detected using functional assays appropriate for the particular nerve involved, such as electrical stimulation of the nerve and detection of contraction of the reinnervated muscle, or can be detected by observing restoration of normal neuronal architecture as a precursor to reacquisition of complete or partial normal function. In preferred healer mouse strains, regrowth and connection occurs after complete transection of nerves of the central or peripheral nervous system. Most preferably, healer mice exhibit maintenance of the optic nerve and eye with no accompanying degeneration of either structure following injury, such as crushing or transection, of the optic nerve. In addition, neurites regrow in the proper direction through a cut region of the optic nerve, and glial cells, such as oligodendrocytes, reappear in the injured area. After cutting or crushing of the spinal cord at the thoracic level, for example, preferred strains of healer mice recover at least partial function in their hind limbs and tail.

Healer mouse strains can be naturally occurring or can be generated, for example, by traditional genetic crossings, by transgenic manipulation, or by mutagenic techniques, as is known in the art. One strain of healer mouse is the MRL mouse. The MRL mouse (H-2k) is derived from an inter-breeding of the LG mouse (75%; H-2d/f), the AKR mouse (12.6%; H-2k); the C3H mouse (12.1% h–2k) and the C57B1/6 mouse (0.3%; H-2b) (13) and was selected originally for its large size. A mutant derived from this colony, MRL/lpr showed enlarged spleen and lymph nodes with age, lymphoproliferation with aberrant control of apoptosis in germinal centers, and a high susceptibility to autoimmune disease with autoantibodies, an arthritis-like syndrome, and glomerulonephritis. This was shown to be the direct result of a retrotransposon insertion into the second intron of the fas gene in the lpr strain (16, 17, 23). However, the rapid and complete wound closure described here is unrelated to fas since the MRL/+ mouse has the same healing characteristics. Furthermore, wound closure is unlinked to the lympadenopathy (R=0.4) associated with lpr mice and the autoantibodies made to histone proteins by these animals (13–15, 24). This lack of fas involvement has been confirmed in mapping studies using MRL/lpr and C57BL/6 backcross mice showing a clear genetic basis for this regeneration trait, unlinked to the fas genetic locus (McBrearty et al., *Proc. Natl. Acad. Sci. U.S.A.* 95, 11792–97, 1998). One characteristic of the MRL mouse is its large size, but there is no evidence that this trait is linked to adult body weight (R=0.12).

Other preferred strains of healer mice can be generated by crossing a healer mouse, such as an MRL mouse, with a non-healer mouse, such as a C57BL/6 mouse, and selecting progeny ($F_1$) mice which display a healer phenotype. $F_1$ healer mice can be intercrossed to form an $F_2$ generation, in which mice with a healer phenotype can be identified. Alternatively, a male or female $F_1$ healer mouse can be backcrossed with a female or male mouse of its healer or non-healer parent strain. The progeny of any of these crosses which display a partial or a complete healer phenotype are healer mice according to the invention. Other non-healer mouse strains, such as 129, can be crossed with a non-healer strain such as C57BL/6 to form healer mouse strains. Characteristics of the healer phenotype are those which are described above.

Mutagenic techniques, including but not limited to, targeted and non-targeted chemical mutagenesis using agents such as DMBA and ENU, as well as irradiation, for example with UV light or X-rays, can be used to induce mutations in one or more genes involved in enhanced wound healing to form a healer phenotype. Genes which can be mutated include, but are not limited to, the genes disclosed herein in Tables 4–11, 14, 15, and genes comprising the SAGE tags disclosed in Tables 12 and 13, as well as genes which regulate them.

It is also possible to create healer mouse strains using transgenic manipulations, to create transgenic, knock-in, or knock-out mice in which the function of one or more genes involved in the enhanced healing response is altered to achieve a healer phenotype. The genes of Tables 4–11, 14, 15, and genes comprising the SAGE tags disclosed in Tables 12 and 13, as well as genes which regulate them, are candidates for such manipulation. Conditional knock-in or knock-out mice, which will express one or more wound healing genes at a designated developmental stage or under particular environmental conditions, can also be constructed. Methods of creating transgenic, knock-in, and knock-out mice are wellknown in the art. (See, e.g., U.S. Pat. Nos. 5,464,764 and 4,873,191).

Identification of Wound Healing Factors

Healer mice can also be used to identify factors which promote wound healing, particularly recovery from central or peripheral nerve injury, as well as genes which encode the factors. Either in vitro or in vivo models of wound healing can be used for this purpose. In vitro models can comprise tissue explants or cells. For example, all or a portion of an ear comprising a cut or a punch wound can conveniently be maintained as an explant in a collagen gel. Explants of other tissues, such as skin and nerve tissue, can also be used. Methods of maintaining tissue explants are well known in the art.

Mammalian cell lines or primary cultures of mammalian cells can also be used as in vitro models of wound healing. Suitable cell types include, but are not limited to, epidermal, mesodermal, cartilage, muscle, neuronal, glial, macrophage, and liver cells or cell lines. Many such cell lines can be obtained from commercial sources such as the American Type Culture Collection. Primary cells can be isolated from mammals such as mice, rabbits, rats, pigs, hamsters, monkeys, or humans. Methods of maintaining such cells in vitro as monolayers, suspension cultures, or cellular reaggregates are also well known.

Alternatively, the model can be a mammal, such as a rat or mouse, which has a wound. The wound can be, for example, a cut or abrasion in the skin, a tail or ear cut or an ear punch, a cut in the liver, or a severed or crushed nerve, including an optic nerve or spinal cord.

The effects of partially or fully purified proteins or nucleic acids, whole cells, such as macrophages or fibroblasts, or tissue extracts, including serum, obtained from healer mice can be tested in the in vitro or in vivo model of wound healing. Regeneration of the tissues and cells and/or morphological or biochemical changes associated with wound healing can be assessed and compared with those processes in the absence of added proteins, cells, or tissue extracts obtained from healer mice or in the presence of proteins, cells, or extracts obtained from non-healer mice. Cells such as fibroblasts, macrophages, and nerve cells isolated from healer and non-healer mice can be treated with cells, serum, or cell extracts from either non-healer or from healer mice.

Properties of a wound healing model which can be assessed include, but are not limited to, enhanced wound healing, enhanced tissue regeneration, cell growth, apoptosis, cell replication, cell movement, cell adhesion, DNA synthesis, protein synthesis, mRNA synthesis, and mRNA stability. Methods of assessing these properties include morphological assessment, either with or without the aid of a microscope, as well as biochemical and molecular biology methods well-known in the art. The alteration of at least one of these properties or of another property associated with enhanced wound healing or tissue regeneration, including an alteration in the time course of an effect, identifies a factor involved in these processes.

Extracts can be prepared from tissues and cells of healer mice using standard tissue disruption techniques, such as sonication, passage through a French press, Dounce homogenization, blending, Polytron disruption, enzymatic digestion, or blending with glass beads, followed by centrifugation. If desired, an extract can be divided into one or more fractions to further identify particular factors involved in enhanced wound healing. Any known method of fractionation, including fractional precipitation with ammonium sulfate, polyethylene glycol, or organic solvents, gel permeation or gel filtration chromatography, ion exchange chromatography, hydrophobic chromatography, dye-ligand affinity chromatography, bio-ligand affinity chromatography, high performance liquid chromatography, fast-flow liquid chromatography, electrophoretic separation methods, and the like, can be used, as is convenient.

Extracts or fractions of extracts which cause an alteration in an in vitro model or which enhance wound healing in an explant or an in vivo model can be purified by biochemical, molecular biological, and/or immunological means using standard technology or can be identified, for example, by selective inactivation. Methods such as two-dimensional gel electrophoresis can also be used to identify proteins which are present or absent, or which are present in different amounts in healer mice compared with non-healer mice. The effects of a purified factor can be confirmed using either an in vitro or an in vivo model of wound healing, as described above.

Alternatively, a subtractive hybridization-type approach can be used to identify factors capable of enhancing wound healing or tissue can be obtained from healer mice, and mRNA can be extracted from these cells using methods well known in the art. Specific mRNAs which are expressed in the cells of healer mice can be isolated by subtractive hybridization of healer mRNA with mRNA obtained from identical cells from non-healer mice. Differentially expressed mRNAs can then be reverse transcribed to form cDNA.

Genes encoding such factors may then be identified, cloned, sequenced and otherwise characterized, as is known in the art. cDNA can be cloned into an expression vector using standard methodologies. Protein expressed from the cDNA can be tested for the ability to enhance wound healing or tissue regeneration of mammalian tissue in an in vitro or in vivo model such as those described above. cDNA which encodes a protein identified as involved in enhanced wound healing can be sequenced and further characterized as desired using ordinary molecular biology technology. The technology required to perform these experiments is well known in the art and is described, for example, in Sambrook et al., Molecular Cloning: A Laboratory Manual (Cold Spring Harbor Laboratory, New York, 1989) and in Ausubel et al., Current Protocols in Molecular Biology, Green & Wiley, New York, 1993).

Any murine wound healing factors which are identified using a healer mouse can be used to identify counterpart factors in other mammals, particularly in humans. For example, degenerate primers encoding portions of murine wound healing factors can be constructed and used to probe cDNA libraries of other mammalian species, preferably human cDNA libraries. Antibodies which specifically bind to a murine wound healing factor can be used to identify similar factors in cells, tissues, extracts, or expression libraries of other mammalian species, preferably human. Thus, the invention should be construed to include the identification of any and all mammalian wound healing factors which share homology with those identified in the murine systems described herein.

The invention also provides methods of screening test compounds for the ability to enhance wound healing. The test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. Members of combinatorial libraries can also be screened for wound healing activity.

A healer model of wound healing is contacted with a test compound. The healer model comprises cells of a healer mouse, and can be any of the in vitro or in vivo types of wound healing models described above. Healer models in which healer and non-healer cells are mixed can also be used. The effect of the test compound on a biological property associated with wound healing is measured in the healer model. These biological properties include, but are not limited to, enhanced wound healing, enhanced tissue regeneration, cell growth, apoptosis, cell replication, cell movement, cell adhesion, DNA synthesis, protein synthesis, mRNA synthesis, and mRNA stability. A test compound which enhances the biological property of the healer model is identified as a potential factor for enhancing wound healing.

Optionally, the effect of the test compound on the biological property of the healer model can be compared with its effect on the same or a similar biological property of a non-healer model of wound healing. Non-healer models are any of the in vitro or in vivo models described above, but do not comprise healer mouse cells. A test compound which alters the biological property of the non-healer model such that it resembles the biological property of the healer model is identified as a potential factor for enhancing wound healing.

Identification of Healer Chromosomal Loci and Genes

Healer mice are particularly useful for identifying genes which are differentially expressed in healer vs. non-healer mice and which are involved in enhanced wound healing. Wound healing genes include genes whose products are directly involved in enhanced wound healing or tissue regeneration, as well as genes which regulate them. Such genes can be identified by a variety of methods. For example, differentially expressed wound healing genes can be identified based on microarray, SAGE, and RT-PCR analyses, as described in the Examples, below.

Chromosomal loci which contain at least one gene which encodes a protein involved in enhanced wound healing can be identified by genome screening. DNA microsatellite markers are identified which can distinguish two strains of mice. One of the two strains is a healer mouse strain, such as the MRL mouse or its progeny. The other strain is a non-healer mouse, such as a C57BL/6. A number of suitable mouse strains are available commercially, for example from Jackson or Taconic Laboratories. Microsatellite markers which segregate with enhanced wound healing in progeny of the two strains identify a chromosomal locus which contains at least one gene which is involved in enhanced wound healing. The product of this gene may be directly involved in enhanced wound healing or may regulate expression of another gene which is involved in enhanced wound healing. This method is described in detail in Examples 3–7, below.

Certain quantitative trait loci identified by this method can be observed to segregate with either male or female healer mice. For example, the quantitative trait loci identified on chromosome 7 segregate with male mice, as do some of the quantitative trait loci on chromosome 13. In addition, quantitative trait loci identified on chromosomes 4 and 18 segregate with male mice. On the other hand, the quantitative trait loci identified on chromosomes 12 and 15 segregate with female mice.

Congenic mouse strains, created by successive backcrossings of the $F_1$ generation of a healer×non-healer cross with its non-healer parent strain and selected for a healer phenotype, are especially useful for identifying chromosomal loci which segregate with the healer phenotype. The healer phenotype of such congenic healer mice ranges from mice with the ability to heal a 2 mm ear hole at least 75% to mice which heal such ear holes completely. For example, after six successive back-crossings, a healer mouse strain was identified which retains approximately 2% of the markers of the healer mouse genome, including the quantitative trait loci shown in Tables 2, 9, and 16, and which exhibits a healer phenotype (Example 19 and Table 16). By repeated back-crossings, strains of healer mice can be created which have at least one of the quantitative trait loci shown in Tables 2, 9, and 16. One locus of particular interest is marker 39, located at 29 cM on chromosome 16. This locus coincides with the location of a wound healing gene termed p63, located between 14 and 29 cM on chromosome 16.

A number of genes involved in enhanced wound healing or tissue regeneration have been identified using these methods. Genes which are differentially expressed between healer and non-healer mouse dendritic cells are shown in Table 15. Genes whose expression is differentially increased or decreased in healer mice after wounding, such as ear punching, are shown in Tables 5, 6, 7, 8, 10, 11, and 15. Levels of some gene products, such as ezrin, c-Jun, and c-myc, are increased in both males and females. Levels of other gene products, such as PI-K p58, and glutathione s-transferase, are decreased in both males and females after wounding.

Still other gene products show more complex changes after wounding, being altered only in males or females, at early or late stages after wounding, or a combination of both. For example, the hox8 (msx2) gene is over-expressed in healer mice at 0, 1, and 5 days after ear punch, but its expression decreases at about 20 days after ear punch, when the ear begins to heal.

Therapeutic Methods for Treating Wounds

Manipulation of the expression of wound healing genes in non-healer mammals, including altering effective levels of their expression products, in non-healer mammals can be used to treat wounds and to enhance or promote wound healing, particularly in humans.

Wounds can be treated at early or late stages after wounding by selectively manipulating expression of particular wound healing genes. Certain of these genes are identified in Tables 5, 6, 7, 8, 10, 11, and 15. Optionally, expression of one or more wound healing genes can be manipulated simultaneously or sequentially. Furthermore, wounds in males or females can be treated most effectively by selecting the appropriate wound healing genes for manipulation.

Expression of genes of Tables 5, 6, 7, 8, 10, 11, and 15 whose expression is selectively decreased and/or increased in healer mice at particular times after wounding can be manipulated in order to enhance wound healing. Particularly preferred genes are msx2 and RARg. Any method known in the art can be used to decrease or increase expression of a wound healing gene. Methods of decreasing effective expression of a wound healing gene include, but are not limited to, use of ribozyme, antisense, or antibody technologies. Methods of increasing effective expression of a wound healing gene include, but are not limited to, providing polynucleotide sequences encoding expression products of the gene such as protein or mRNA, as well as providing the expression products themselves.

In one embodiment of the invention, expression of a wound healing gene is altered using an antisense oligonucleotide sequence. The antisense sequence is complementary to at least a portion of the coding sequence of the gene. The coding sequences of preferred wound healing genes can be obtained from databases such as Genbank; accession numbers for some of thtese genes are provided in Table 14. Preferably, the antisense oligonucleotide sequence is at least 11 nucleotides in length, but can be at least 12, 15, 20, 25, 30, 35, 40, 45, or 50 or more nucleotides long. Longer sequences can also be used. Antisense oligonucleotide molecules can be provided in a construct and introduced into cells using standard methodologies to decrease expression of one or more wound healing genes.

Antibodies which specifically bind to a wound healing protein can also be used to alter the effective expression levels of a wound healing gene. Wound healing-specific antibodies bind to a wound healing protein and prevent the protein from functioning in the cell. Preparations of polyclonal and monoclonal antibodies can be made using standard methods. Antibody fragments such as Fab, single-chain Fv, or F(ab')$_2$ fragments can also be prepared. If desired, antibodies and antibody fragments can also be "humanized" in order to prevent a patient from mounting an immune response against the antibody when it is used therapeutically, as is known in the art. Other types of antibodies, such as chimeric antibodies, can be constructed as disclosed, for example, in WO 93/03151. Binding proteins which are derived from immunoglobulins and which are multivalent and multispecific, such as the "diabodies" described in WO 94/13804, can be prepared and used in methods of the invention. Anti-idiotype antibodies, directed against unique sequence variants in wound healing gene products, can also be used in therapeutic methods of the invention.

Useful antibodies specifically bind to epitopes present in proteins encoded by a wound healing gene. The amino acid sequences of these proteins are available from Genbank (see, e.g., Table 14 for accession numbers). Antibodies which specifically bind to wound healing proteins provide a detection signal at least 5-, 10-, or 20-fold higher than a detection signal provided with other proteins when used in Western blots or other immunochemical assays. Preferably, antibodies which specifically bind to a wound healing protein do not detect other proteins in immunochemical assays and can immunoprecipitate the wound healing protein from solution.

Antibodies can be purified by methods well known in the art. For example, the antibodies are affinity purified, by passing the antibodies over a column to which a wound healing protein is bound. The bound antibodies can then be eluted from the column, for example, using a buffer with a high salt concentration.

Ribozymes can be used to inhibit gene function by hybridizing to and cleaving an RNA sequence of a wound healing mRNA, as is known in the art (e.g., Haseloff et al., U.S. Pat. No. 5,641,673). The nucleotide sequences of wound healing genes, available from databases such as Genbank (see Table 14), are sources of suitable hybridization region sequences.

Preferably, the mechanism used to decrease the effective expression of the involved gene decreases levels of gene expression products, such as mRNA or protein, by 50%, 60%, 70%, or 80%. Most preferably, effective expression of the gene is decreased by 90%, 95%, 99%, or 100%. Effective expression of the involved gene can be assessed using methods well known in the art, such as hybridization of nucleotide probes to mRNA of a wound healing gene, quantitative RT-PCR, or detection of wound healing protein using specific antibodies.

Expression of wound healing genes whose expression is increased in healer mice after wounding can be effectively increased in a non-healer mammal in order to enhance wound healing. Any method known in the art for enhancing gene expression can be used for this purpose. For example, the coding sequence of one or more wound healing genes can be delivered to cells in the vicinity of a wound. Mechanical methods, such as microinjection, liposome-mediated transfection, electroporation, or calcium phosphate precipitation, can be used to introduce the coding sequence into cells in which it is desired to increase wound healing gene expression. Alternatively, if it is desired that the cells stably retain the construct, it can be supplied on a plasmid and maintained as a separate element or integrated into the genome of the cells, as is known in the art. The construct can include transcriptional regulatory elements, such as a promoter element, an enhancer or UAS element, and a transcriptional terminator signal, for controlling transcription of the coding sequence in the cells.

Vectors, such as retroviral- or adenoviral-based vectors, can be used for this purpose. Recombinant retroviruses are described in numerous references, including Mann et al., *Cell* 33:153, 1983, Cane and Mulligan, *Proc. Nat'l. Acad. Sci. USA* 81:6349, 1984, Miller et al., *Human Gene Therapy* 1:5–14, 1990, and U.S. Pat. Nos. 4,405,712, 4,861,719, and 4,980,289.

Advenoviral vectors are preferred. The use of adenoviral vectors in vitro is described in Chatterjee et al., *Science* 258: 1485–1488 (1992), Walsh et al., *Proc. Nat'l. Acad. Sci.* 89: 7257–7261 (1992), Walsh et al., *J. Clin. Invest.* 94: 1440–1448 (1994), Flotte et al., *J. Biol. Chem.* 268: 3781–3790 (1993), Ponnazhagan et al., *J. Exp. Med.* 179: 733–738 (1994), Miller et al., *Proc. Nat'l Acad. Sci.* 91: 10183–10187 (1994), Einerhand et al., *Gene Ther.* 2: 336–343 (1995), Luo et al., *Exp. Hematol.* 23: 1261–1267 (1995), and Zhou et al., *Gene Therapy* 3: 223–229 (1996). In vivo use of adenoviral vectors is described in Flotte et al., *Proc. Nat'l Acad. Sci.* 90: 10613–10617 (1993), and Kaplitt et al., *Nature Genet.* 8:148–153 (1994). Other viral vectors, such as those based on togaviruses or alpha viruses, can also be used.

A wound healing coding sequence can also be combined with a condensing agent, such as polylysine, polyarginine, polyornithine, protamine, spermine, spermidine, or putrescine, to form a gene delivery vehicle. Many suitable methods for making such linkages are known in the art. Alternatively, a wound healing coding sequence can be associated with a liposome to deliver the coding sequence to cells at the site of the wound. Other suitable methods of providing wound healing coding sequences include DNA-ligand combinations, such as those disclosed in Wu et al., *J. Biol. Chem.* 264:16985–16987 (1989). Wound healing coding sequences can also be delivered to the site of an internal wound, for example, using receptor-mediated targeted delivery. Receptor-mediated DNA delivery techniques are taught in, for example, Findeis et al. *Trends in Biotechnol.* 11, 202–05 (1993); Chiou et al., Gene Therapeutics: Methods and Applications of Direct Gene Transfer (J. A. Wolff, ed.) (1994); Wu & Wu, *J. Biol. Chem.* 263, 621–24 (1988); Wu et al.,*J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991). Expression of a wound healing gene can be monitored by detecting production of mRNA which hybridizes to a delivered coding sequence or by detecting the protein product of the gene using, for example, immunological techniques.

Expression of an endogenous wound healing gene in a cell can also be altered by introducing in frame with the endogenous gene a DNA construct comprising a targeting sequence, a regulatory sequence, an exon, and an unpaired splice donor site by homologous recombination, such that a homologously recombinant cell comprising a new transcription unit is formed. The new transcription unit can be used to turn the wound healing gene on or off as desired. This method of affecting endogenous gene expression is taught in U.S. Pat. No. 5,641,670, which is incorporated herein by reference.

The targeting sequence is a segment of at least 10, 15, 20, or 50 contiguous nucleotides selected from the nucleotide sequence of a wound healing gene. The nucleotide sequences of the wound healing genes disclosed herein are available, for example, from Genbank, using the accession numbers provided in Table 14. The transcription unit is located upstream of a coding sequence of the endogenous wound healing gene. The exogenous regulatory sequence directs transcription of the coding sequence of the wound healing gene.

Optionally, effective expression of one or more wound healing genes can be altered in cells which have been removed from a mammal, such as dermal fibroblasts or peripheral blood leukocytes. The cells can then be replaced into the same or another mammal with a wound, preferably to or within the vicinity of the wound to enhance healing of the wound. Alternatively, cells obtained from healer mice can be used to treat a wound in a mammal. Preferred cells include macrophages, stem cells, fetal liver cells, peripheral blood leukocytes, and bone marrow cells. Extracts from these cells can be prepared using standard methodologies and used for wound treatment. The cells or cellular extracts can be placed directly at the site of the wound to promote its healing.

In another embodiment, protein products of wound healing genes whose expression is increased after wounding in healer mice can be applied directly to the area of the wound. Protein products of wound healing genes can be used in a pharmaceutically acceptable composition and can be applied topically, as is well known in the art and described below.

The lowered capacity for wound healing which occurs in aged mammals, including humans, can be enhanced by suppressing T cell function, for example using an antibody which specifically binds to a T cell receptor (TCR) or, in experimental mammals, by genetically eliminating functional T cell receptors. Anti-TCR antibodies are available in the art or can be prepared using established methodologies. Optionally, a polynucleotide encoding a single chain anti-TCR antibody can be used. Anti-TCR antibodies can be administered to mammals, including humans, to reduce levels of functional TCRs. Sub-populations of TCRs can also be targeted.

Wounds which can be treated using methods of the invention include, but are not limited to, cuts, stretches, tears, pulls, abrasions, burns, bone breaks, crushes, scrapes, contusions, bruises, and the like. Particularly, peripheral or central nerve injuries, such as crushed or severed nerves, including the spinal cord, can be treated. Methods and compositions of the invention can be used to treat and thus enhance healing of a wound by promoting processes such as angiogenesis, chondrogenesis, return of hair follicles and/or sebaceous glands, reepithelialization, rapid connective tissue proliferation, deposition of organized extracellular matrix, and restoration of normal tissue architecture and function. Surgical adhesions can be prevented by prophylactic treatment of surgical incisions using compositions and methods of the invention. These methods and compositions are useful in any situation in which regeneration or healing of a wound without formation of scar tissue is desired.

Wound healing compositions of the invention can comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles.

Pharmaceutically acceptable salts can also be used in wound healing compositions, for example, mineral salts such as hydrochlorides, hydrobromides, phosphates, or sulfates, as well as salts of organic acids such as acetates, proprionates, malonates, or benzoates. Wound healing compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for a wound healing composition.

Administration of wound healing compositions of the invention can include local or systemic administration, including injection, oral administration, particle gun, or catheterized administration, and topical administration. For treatment of wounds on the surface of the body, a wound healing composition is typically prepared in a topical form, either as a liquid solution, suspension, gel, or cream. However, solid forms suitable for solution or suspension in liquid vehicles prior to injection can also be prepared, for local treatment of internal wounds. Both the dose of a particular wound healing composition and the means of administering the composition can be determined based on specific qualities of the wound healing composition, the condition, age, and weight of the patient, the type and extent of the wound being treated, and other relevant factors.

The above disclosure generally describes the present invention. All references cited in this disclosure are expressly incorporated herein by reference. A more complete understanding can be obtained by reference to the following specific examples which are provided herein for purposes of illustration only, and are not intended to limit the scope of the invention.

Materials and Methods

The following materials and methods were used in the examples described below.

Mice. The MRL/MpJ-Fas$^{lpr}$ (hereafter referred to as MRL/lpr) mice were obtained from the Jackson Laboratory (Bar Harbor, Me.). C57BL/6 mice were acquired from the Taconic Laboratory (Germantown, N.Y.). Mice were bred and maintained under standard conditions at The Wistar Institute (Philadelphia, Pa.).

$F_1$, $F_2$ and MRL/lpr backcross populations were generated to conduct the genetic studies. The female parent used for generating the $F_2$ and backcross animals was MRL/lpr. In the examples below, alleles derived from the C57BL/6 parent are designated B and the MRL/lpr-derived alleles are designated S.

Phenotyping A 2.1 millimeter through-and-through hole was made in the center of the cartilagenous part of both ears of six week old mice using a metal ear punch (Fisher Scientific, Pittsburgh, cat #01-337B). The holes were measured at the time of wounding and followed for wound closure using a grid-etched reticle (Bausch and Lomb, 7×).

Histology. Ears were removed with scissors by cutting at the base of the pinna. They were fixed overnight in 10% buffered formalin. To facilitate sectioning, they were held flat during fixation by inverting the lid of a processing cassette on the base and sandwiching the flattened ear by applying gentle pressure with a rubber band.

Once fixed, ears were bisected across the widest point of the hole under a dissecting microscope, using a #10 scalpel blade. The two halves were then glued together with collodion, again using the dissecting microscope to obtain perfect alignment of the cut edges and hole margins. Because the collodion would most likely dissolve in reagents used to prepare specimens for paraffin embedding, the ears were sutured together using 5.0 silk on a 1 ½ inch straight Keith Abdominal cutting needle with a triangular point.

Tissues were embedded in paraffin and sectioned so that the cut edges containing the hole margins were in the plane of the section. Sections were stained with hematoxylin and eosin or with Gomori trichrome stain.

Genetic Analysis. Genomic DNA was prepared from the liver of each animal in the (MRL/lpr X C57BL/6)×(MRL/lpr X C57BL/6) $F_2$ population. Frozen tissue was homogenized and digested overnight with 100 mg/ml proteinase K. Samples were treated with two phenol:chloroform extractions and one final chloroform extraction. Finally, genomic DNA was purified by an overnight dialysis against TE buffer.

PCR primers, purchased from Research Genetics (Huntsville, Ala.), were employed to perform a genome wide scan of the mouse. Amplification was conducted using Boehringer Mannheim reagents with the following concentrations: 1×PCR buffer, 0.375 mM dNTPs, 0.5 U/$\mu$ls of Taq polymerase, 0.165 $\mu$M of each primer, and 160 ng/20 $\mu$ls of genomic DNA. Cycling conditions include a 1 min at 95° C. denaturing, 35 to 50 cycles of 1 min at 94° C., 1 min 30 sec at 55° C., 2 min 10 sec at 72° C., and a 6 min final extension at 72° C. PCR products were resolved using 3% Metaphor agarose (FMC) and were visualized through ethidium bromide staining. This method was followed for the majority of polymorphic markers. In the case of small base pair differences, PCR amplification was carried out using $^{32}$P-ATP labeled forward primers as described (38). Radiolabelled PCR products were then fractionated by size on 6% denaturing polyacrylamide gels.

Statistics. Genotype data was organized and analyzed through the use of Map Manager QT (39). For quantitative trait analysis, critical threshold values for significance of linkage were determined by the permutation test, based on a regression model developed by Churchill and Doerge (40, 41). The values for the additive model of inheritance were calculated in terms of a likelihood ratio statistic (LRS).

The threshold in the $F_2$ under assumptions of the additive model for suggestive linkage is LRS$\geq$3.3 and for significant linkage is LRS$\geq$10.7. The dominant, free and recessive models were also tested and did not show a significant difference (i.e., they were less than 18-fold different) in resultant p values. The additive regression model was used because it is the simplest model and because it is consistent with the mode of inheritance of the quantitative trait loci (QTL) determined in this study. It should also be noted that the use of the additive regression model does not assume the pattern of inheritance to be strictly additive and at present the degree of additivity and dominance has not been determined. The threshold values in the backcross are 3.7 and 11.8, respectively. Loci were named as healing quantitative QTL if they independently attained significance in either cross or a suggestive level of significance in one cross, confirmed in the other (p<0.05). Microsatellite markers were evaluated individually for linkage to the healing phenotype, based on the threshold values. In addition, a mean healing score for markers closely linked to each healing QTL was calculated independently of other loci using ANOVA, using a Bonferroni/Dunn post-hoc test for making the three possible pairwise comparisons in the $F_2$, resulting in single-locus genotypic values (Table 3) (45).

EXAMPLE 1

Kinetics and Gross Aspects of the Wound Healing Phenotype

C57BL/6 and MRL mice were ear punched using a standard metal ear punch to create a well circumscribed circular surgical wound of about 2 mm in diameter at a site at which the thickness of the ear is considerably less than a millimeter. The animals used initially were within the 8–12 week young adult age range so that early developmental considerations would not be an issue. As can be seen in FIG. 1, by day 15 maximal closure was achieved in the C57BL/6 with a 30% reduction in the original hole diameter, which remains stable. In contrast, the MRL achieves an 85% reduction in hole diameter by day 15 with complete closure by day 25. Re-examination of the ears on day 81 showed no further changes.

Figures 1, 12A:
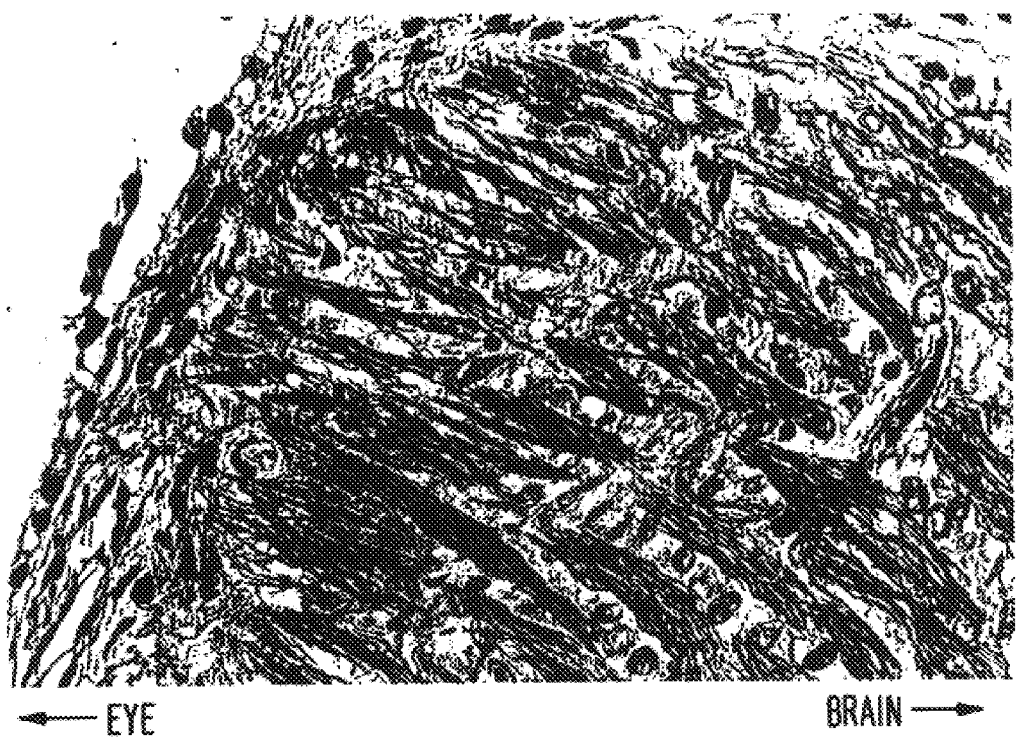
FIG. 12A is an image depicting a histological longitudinal section of the healer (MRL) mouse normal uncut right eye-specific tissue. This section was stained with Bodian's silver stain specific for axons.
Figures 2, 12A:
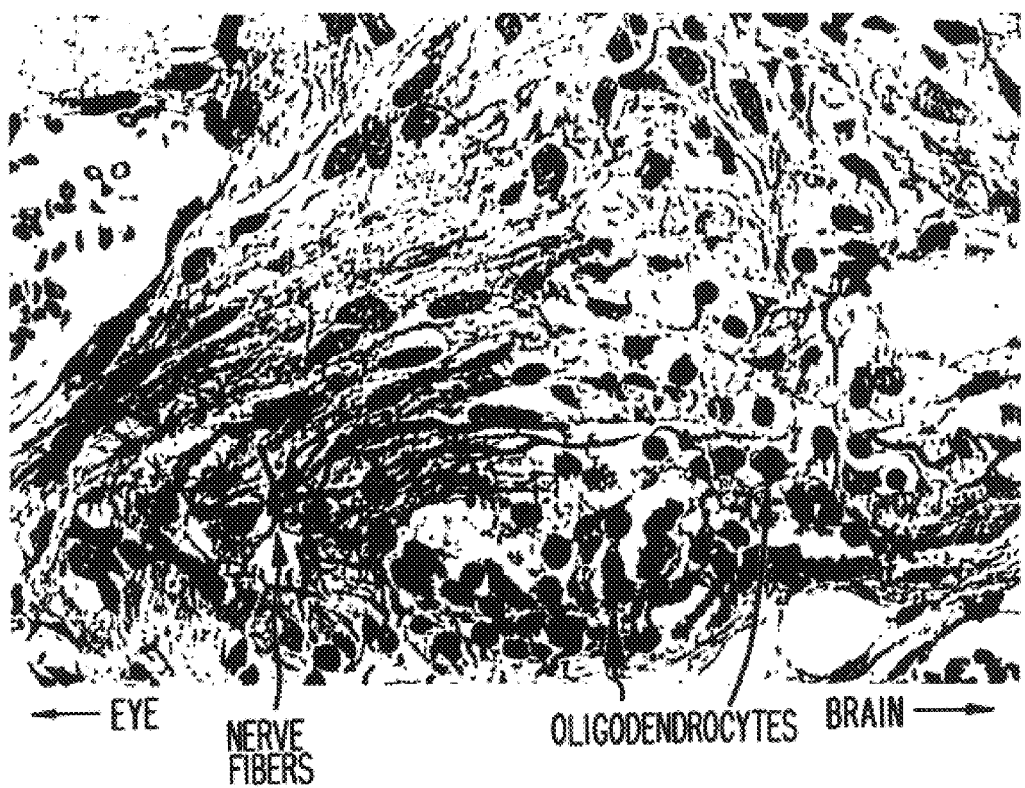

In FIG. 2, the closed MRL wound is evident and it is difficult to identify the original site of the hole since there is no fibrosis or scarring.

EXAMPLE 2

Histological Aspects of the Wound Healing Phenotype

Figure 4A:
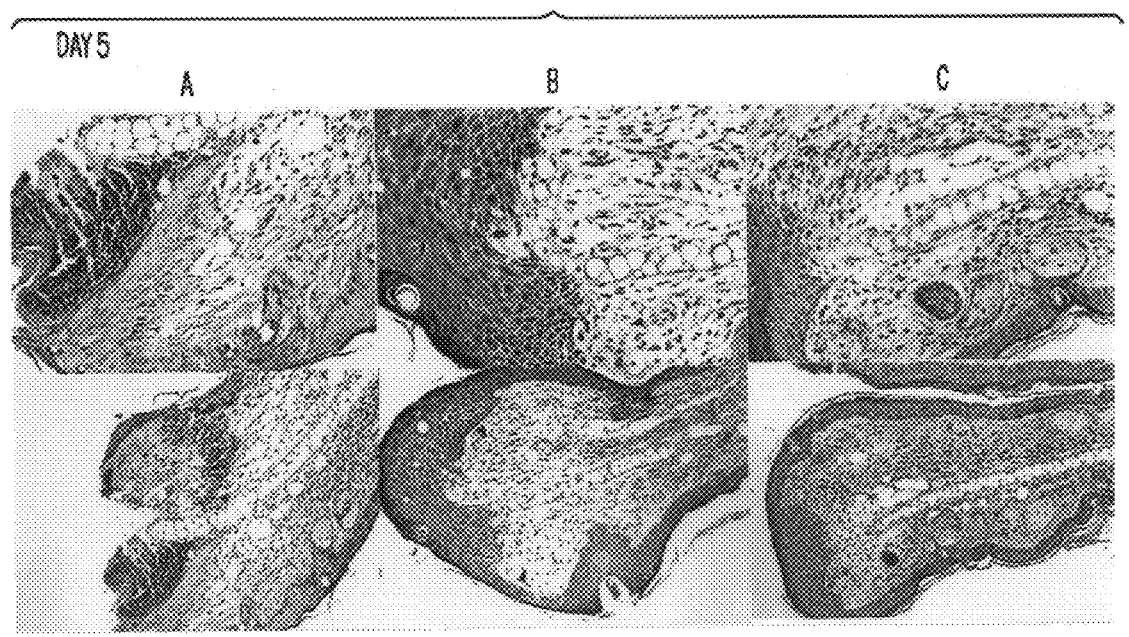
FIG. 4A, Panels A–C. Day 5 (A, B, C: 40x-upper panels and 20x-lower panels): Swelling at the MRL wound site is extensive with neovascularization (40x-arrows) and marked dermal fibroblast proliferation (20x-large arrows). Adnexae in the new epithelium can be seen here (20x-small arrows). A C57BL/6 wound that has failed to epithelialize is shown here, although this is not typical (20x- *).

Histologic sections of healing ear punch holes were examined during the first two days after injury to determine if there was a defect in the ability of their epithelium to migrate across the cut edge of the dermis and cartilage, thereby allowing uninhibited connective tissue proliferation (FIG. 3). However, not only did epithelium promptly migrate across the MRL wounds, but this change occurred one day earlier for MRL mice (day 2) than for C57BL/6 mice (day 3). Indeed, for MRL mice epithelium completely covered virtually all wounds examined after day 1. Epithelium covered all C57BL/6 wounds examined after and including day 3, except for one wound from day 5 (FIG. 4A) which showed continued presence of eschar with migrating epithelium failing to bridge the cut edge.

As ears were prepared for histology, two grossly observable differences were noted between C57BL/6 and MRL. First, for all time points, the tissue surrounding the wounds in the MRL ears was severely hyperemic when compared to that of the C57BL/6 wounds. Second, starting on day 4, and continuing on each succeeding day, a prominent annular swelling was observed around the MRL wounds that was absent for C57BL/6 wounds.

Figure 4B:
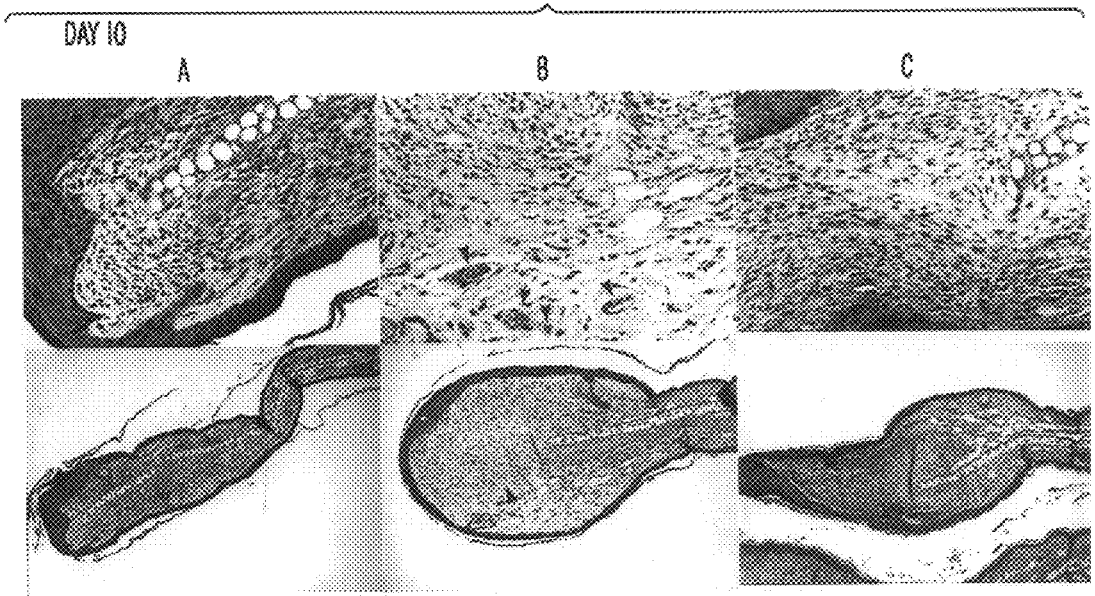
FIG. 4B, Panels A–C. Day 10 (A, B, C: 40x-upper panels and 10x-lower panels): There is marked neovascularization (40x-arrows) and fibroblast proliferation (10x-arrows) seen in the MRL wound extending out beyond the borders of the wound where the cut cartilage edges are seen. Note the extent to which dermal cells have migrated out beyond the wound margin marked by the cartilage edge for the two MRL ears compared to the C57BL/6 ear.

Consistent with the grossly observable differences between the wounds, histological examination at each time-point (5 days, FIG. 4A; 10 days, FIG. 4B; 20 days, FIG. 4C) showed a marked difference in the degree of angiogenesis, cell proliferation, connective tissue matrix formation, fibroblast migration, and ECM deposition which occurred in the two strains. Also, the presence of hair follicles with accompanying sebaceous glands within the healing wounds was noted for both MRL and C57BL/6 wounds but appeared more prominent and numerous in MRL than in C57BL/6 wounds.

At all of these time points, C57BL/6 wounds have shown limited progression beyond the cut cartilage margins and have a distinct paucity of epidermal hair follicles and sebaceous glands. In contrast, the MRL wounds show marked progress towards full closure due to extensive dermal proliferation and are well supplied with hair follicles and sebaceous glands in the new growth zone. ECM is laid down so as to preserve normal architecture, underlying connective tissue is hyperplastic, and the epidermis is rich and thick. The ear cartilage layer has not significantly extended into the wound site beyond the initial cut margin.

Figure 5:
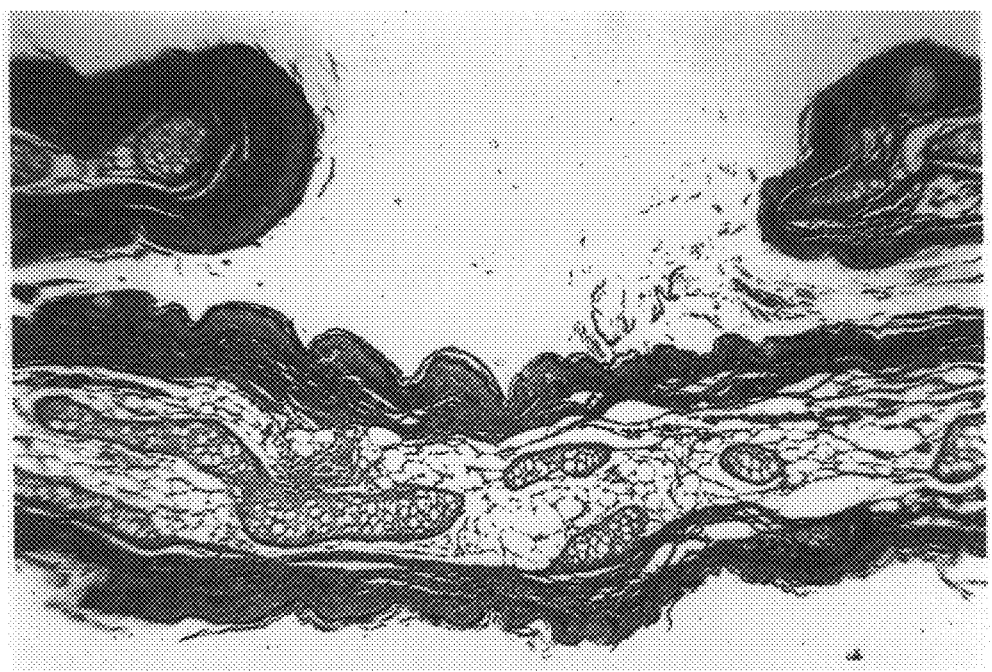
FIG. 5. Late-stage ear wound closure. Wound sites (n=3) 81 days after wounding for C57BL/6 (top) and MRL/lpr (bottom) mice were aligned using a dissection microscope and sutured together to assure sectioning through the former wound for MRL/lpr tissue. Cartilagenous islands (small arrow) present throughout the MRL/lpr section are surrounded by prominent adipocytes (large arrow). These features are absent from the C57BL/6 tissue. The tissue sections are stained with Gomori trichrome. Magnification=10x.

C57BL/6 and MRL ears are shown on day 81 after wounding in FIG. 5. Numerous ingrowths of cartilage can be seen in the MRL ear that are absent from the C57BL/6 ear. The cartilage ingrowths are surrounded by numerous adipocytes which normally make up the minor subcutaneous or hypodermal layer connecting ear cartilage to dermis. It is not clear why fat cells have come to be such a prominent cell type by this time point.

EXAMPLE 3
The Pattern of Inheritance of the Wound Healing Trait is Quantitative Our initial findings on the hereditary nature of the wound healing trait can be seen in FIG. 6 (upper panel). In these studies, mice were ear punched at 6 weeks of age and were examined at 2 weeks and 4 weeks after ear punching. The 4 week ear hole size of the MRL mice ranged from 0 to 0.4 mm, while the ear hole size of the C57BL/6 mice ranged from 1.2 to 1.6 mm. These two healing phenotypes were non-overlapping. Fifteen $F_1$ mice bred from MRL×C57BL/6 had ear holes intermediate between the two parents (ranging from 0.4 to 1.1 mm).

In an initial experiment, two backcross populations were created by using (MRL female×C57BL/6 male) $F_1$ females and mating them to the parental males (FIG. 6, lower panel). The backcross population to MRL displayed a curve skewed to MRL-type healing. In the backcross population to C57BL/6, the progeny showed a curve with its mean displaced to C57BL/6-type (i.e. poor) healing. The healing thus appears to be a quantitative trait.

EXAMPLE 4
The Pattern of Inheritance of the Wound Healing Trait

Figure 7:
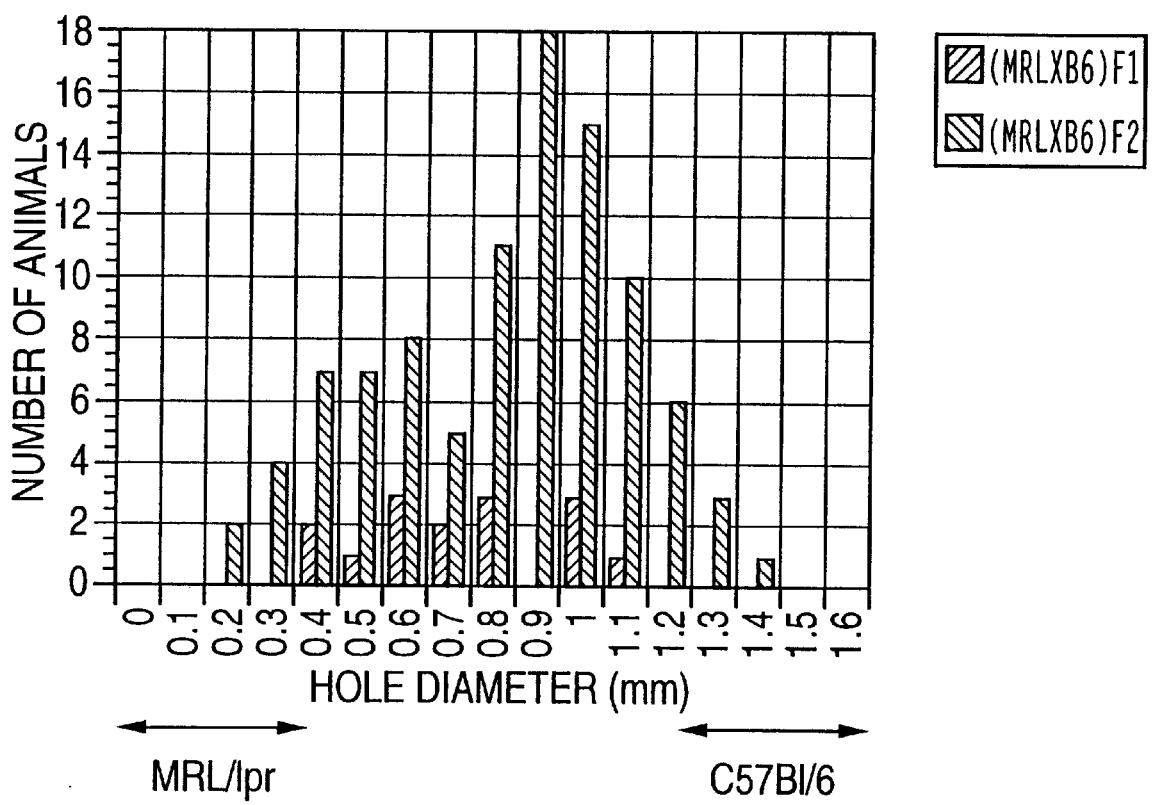
FIG. 7. Histogram of wound closure in (MRL/lpr× C57BL/6)$F_1$ and $F_2$ intercross populations.

All MRL mice quickly and effectively close the wounds in their ears; C57BL/6 (B6) mice are unable to completely close their wounds (36). The $F_1$ has an intermediate phenotype, with considerable variability (FIG. 7). Like the $F_1$, the (MRL/lpr×B6)$F_2$ population demonstrates a bell-shaped curve of healing diameters (FIG. 7). The backcross (BC1) population to MRL/lpr ((MRL/lpr×B6)$F_1$×MRL/lpr) displays a curve skewed to MRL/lpr -type healing, whereas in the backcross population to B6 [(MRL/lpr×B6)$F_1$×B6], the progeny show a mean displaced to B6-type (i.e. poor) healing (36).

The healing profiles of each of the populations used in this study are given in Table 1. The distribution of the variance in each of these populations compared to those of the parental and $F_1$ mice were used to give a rough estimate of the number of unlinked genes that contribute to this quantitative trait (42, 43). From this calculation, it is likely that at minimum three to four unlinked loci (QTLs) have an impact on the healing trait in this strain combination.

EXAMPLE 5
Mapping of SSLP Markers and Significant Threshold Values

A total of 436 SSLP markers were tested for potential polymorphisms between the two strains of mice. Ninety two markers detected allelic variants in the parental strains and therefore were used for genotyping of the segregating populations. Markers were chosen based on their location in the genome, in an attempt to make a linkage map with an even spacing of 20 centimorgans between markers to generate a complete genome-wide scan (44). In regions where linkage to the healing trait was detected, the density of markers was increased to obtain a more accurate genetic dissection in the area of interest. Overall, genomic coverage reached ~97.7 percent across the nineteen autosomes. Surprisingly, despite the distant genetic relationship between these two inbred strains (13, 37), no polymorphisms were found on the X chromosome (0/18 primers tested, data not shown).

The 92 polymorphic microsatellite markers were then used to map the wound healing/regeneration trait in 101 mice from the (MRL/lpr×C57BL/6 )$F_2$ intercross. For assessment of the probability of genetic linkage, critical values were calculated from this database using the permutation test (40; see Materials and Methods). The order of all makers in this linkage analysis was consistent with the order predicted by the available genomic maps (Whitehead Institute/MIT, and Mouse Genome Database, The Jackson Laboratory, Bar Harbor, Me., available at the URL address: http file type, www host server, domain name informatics-.jax.org.

EXAMPLE 6
Mapping of Quantitative Trait Loci Linked to the Healing Phenotype in the $F_2$ Population Table 2 shows all of the microsatellite markers that were positive for linking to the healing phenotype in two crasses and Table 3 lists the healing scores for markers associated with wound closure. Table 9 shows microsatellite markers that were positive for linking to the healing phenotype analyzed seperated for male and female mice.

In the $F_2$ cross, QTLs that contribute to the healing phenotype and are derived from MRL/lpr exist in three primary support intervals. Two of these QTLs are located on individual sites on chromosome 13, and are designed heal2 and heal3. These QTLa are located as follows (with their corresponding microsatellite marker): heal2, on promimal chromosome 13, near D13Mit115 (p=0.0019) and heal3, at a more distal location near D13Mit129 (p=0.0010). One of the two QTLs on chromosome 13 (heal13) has achieved significant likelihood of linkage to the healing trait while the other (heal2) is suggestive, though confirmed in a second cross (see below).

Multiple markers near these loci show a suggestive level of significance, including for heal2:D13Mit135 and D13Mit116 and for heal3:D13Mit53, D13Mit151, D13Mit144, and D13Mit107 (Table 2). D13Nds1 and D13Mit191 both achieved highly suggestive LRS values but the assignment of a QTL in this region is provisional at the present time because the 95% confidence intervals for these markers and the two flanking QTLs overlap (not shown). Nevertheless, there are distinct breaks between these QTLs in the level of significance for their linkage to healing with no deviation from the predicted order of these markers. A second region that contains a QTL with significant linkage to the healing phenotype was detected on chromosome 15, in the region of marker D15Mit244 (p=0.0011). Other microsatellite markers mapping to this location which meet the criteria for suggestive linkage to wound healing include D15Mit172 and D15Mit14. We have designated this QTL heal4.

In addition to the QTL on chromosome 13 and chromosome 15, which have MRL/lpr-derived healing alleles, a B6-derived healing QTL was mapped to chromosome eight, near the marker D8Mit211, with a significant LRS value (10.7, p=0.0011). Other markers in this location which showed linkage were D8Mit132, D8Mit166, and D8Mit249. This locus was the first QTL identified and was designated heal1.

The contribution of each heal locus to the process of wound closure, as expressed by the single-locus genotypic values (45) (Table 3), generally fit an additive mode of inheritance, with the heterozygote healing score approximately halfway between the scores of the two homozygotes. One exception is the heal3 QTL, which may be recessive (i.e., heal3$^{s/s}$ homozygotes show significantly better wound closure than either heterozygotes or heal3$^{b/b}$ homozygotes). In addition, the heal3 QTL appears to interact with heal1 to give the most completely healed ear holes (ANOVA, p=0.017). The average residual wound in heal1$^{b/b}$ homozygotes is 0.73+0.27; however, in animals that are both heal1$^{b/b}$ and heal3$^{s/s}$, residual wound size is 0.53+0.30 (FIG. 2). Conversely, in mice homozygous for heal1$^{s/s}$ but also homozygous for heal3$^{b/b}$, the residual wound size is 1.2+0.22. Other pairs of heal QTLs also show these largely additive interactions, but do not attain statistical significance.

EXAMPLE 7
Mapping of Quantitative Trait Loci Associated with the Healing Phenotype in the Backcross To confirm the linkage assignments seen in the F$_2$, we conducted a small backcross study (42 mice), using (MRL/lpr×B6) F$_1$ females and MRL/lpr males as parents. The F1 between MRL/lpr and B6 has an intermediate wound closure phenotype, and all progeny in this cross were expected to show intermediate to good healing. In fact, this was largely the case, although several mice in the back cross had poor wound healing. An analysis of this cross showed linkage to healing at locations that coincided with the supported intervals of association seen in the F$_2$ for both of the two QTLs on chromosome 13 (heal2 and heal3). These QTLs were near markers D13Mit115 (LRS value=5.0, p=0.0261) and D13Mit129 (LRS value=8.3, p=0.0040), respectively (Table 2). In addition, linkage to the healing phenotype was also detected on chromosome 12 (heal5) at marker D12Mit132 with a LRS value of 10.9 (p=0.0009) and at the closely-linked marker, D12Mit233 (LRS=9.4, p=0.0022). This linkage was supported by suggestive linkage in the F$_2$. The single locus genotypic value for residual wound diameter for the heal5 (D12Mit132) QTL is also given in Table 3. Finally, a locus showing a highly suggestive LRS value of 10.2 (p=0.0014) was found on chromosome 7 near marker D7Mit220.

EXAMPLE 8
Differential Gene Expression in Healer and Non-Healer Mice

Assays were carried out to analyze differential gene expression in healer versus non healer mice at different times during the healing process after ear punch.

SAGE analysis. mRNA transcripts were identified and their levels quantitated using the SAGE technique, as described in U.S. Pat. No. 5,695,937. In order to use SAGE for transcript identification and quantitation, messenger RNA (mRNA) was first prepared from the desired cell or tissue sample. Complementary DNA (cDNA) was then synthesized from the mRNA using standard techniques. The entire population of cDNA molecules was treated to create a single unique "tag" from each cDNA. These tags are listed in Tables 12 (C57BL/6) and 13 (MRL).

The sequence of the tags serves to identify each transcript. The number of times each tag occurs measures the number of copies of the mRNA originally present in the biological sample. Tags can then be identified and quantitated. Gene expression data obtained from SAGE analysis of each tissue was stored in a database to facilitate multiple comparisons with gene expression in other tissues.

Microarray analysis. Gene expression in wound tissue of healer and nonhealer mice and their progeny was analyzed using the Atlas Mouse cDNA Expression Array (Clontech). This array includes 588 genes that play key roles in a variety of biological processes. cDNA was synthesized from healing wound tissue from healer and nonhealer mice, labeled with $^{32}$P, and hybridized separately to the arrays according to the protocol provided. After a high-stringency wash step and autoradiography, expression profiles were obtained.

RT-PCR and Differential Display. The presence of known gene products in healing wound tissue was analyzed using RT-PCR and Differential Display analysis. cDNA was synthesized from RNA using reverse transcriptase. The cDNA was amplified using specific primers and displayed as fragments by gel electrophoresis for comparison. Quantitation was carried out using titrations of input material, and then samples were compared. This method is valuable for assessing the presence of known gene products and is relatively quantitative.

Expression of candidate genes identified in the genome screen described above, were separated into the following groups. Group I comprises genes which may be directly involved in wound healing based on their mapping to a chromosomal locus identified in the genome screen. Group IA comprises genes in loci whose correlation with wound healing are statistically suggestive. Group IB comprises genes in loci whose correlation with wound healing are statistically significant. Group II comprises genes which are regulated by products of the mapped genes in Group I.

The results of these assays are given in Tables 5–8. Differential expression of several candidate gene products were confirmed in two assays: MSX-2 or HOX8 (chromosome 13) and RARG (chromosome 15) were identified by both RT-PCR and microarray analyses at early time points. The gene encoding epidermal keratin (on chromosome 15) was identified by microarray at all time points and by SAGE analysis. Expression of RARG and epidermal keratin could be related, because retinoic acid (RA) causes growth of epidermal cells via the RA receptors in skin (i.e., RARG). Epidermal keratin would then be upregulated.

EXAMPLE 9
Quantitative Trait Loci Associated with Healing

Figure 8:
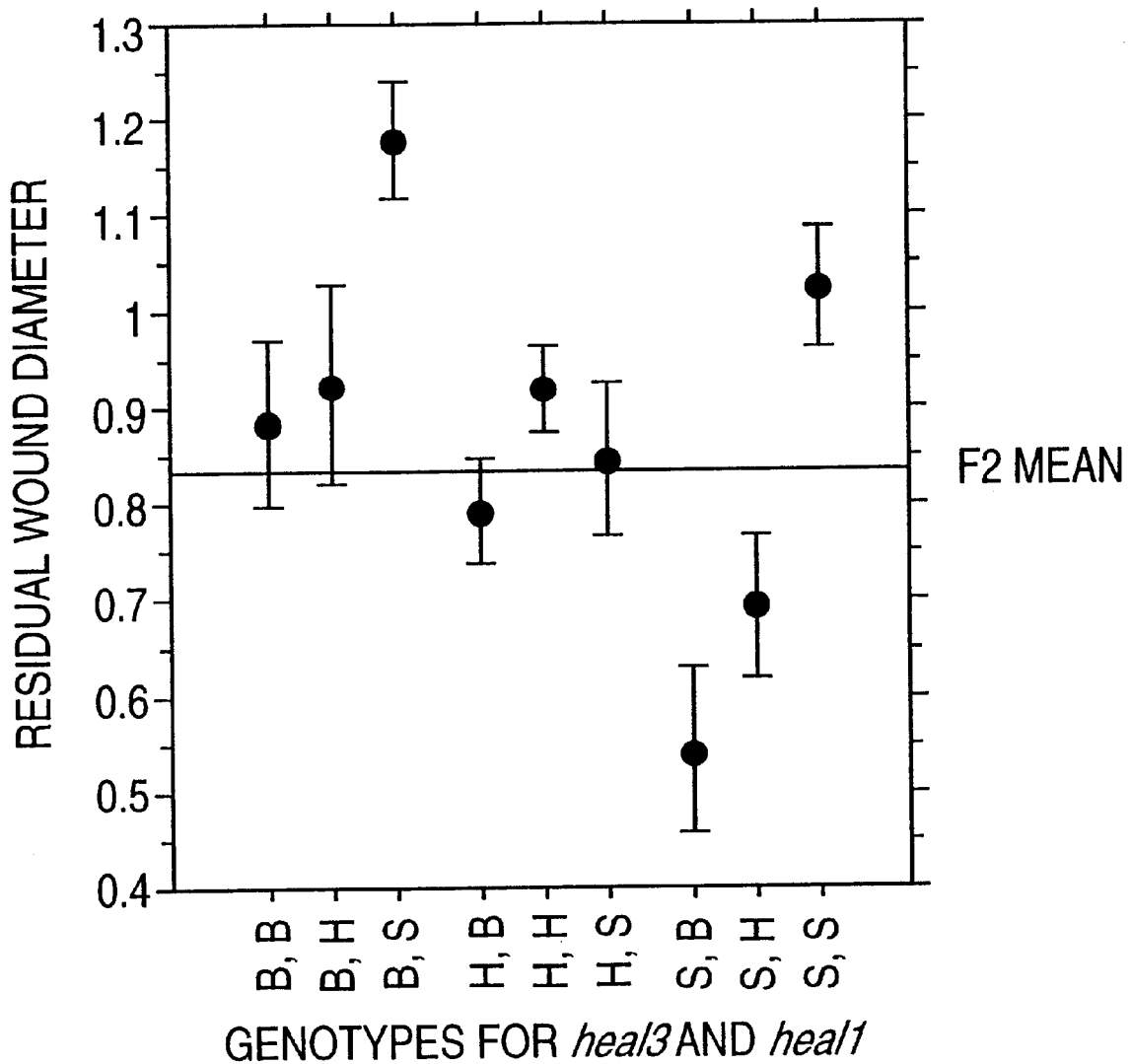
FIG. 8. Additive effects of heal1 and heal3 on wound closure. Average residual wound diameters are plotted for each genotype, with the results grouped by D13Mit129 and D8Mit211. The mean of all $F_2$ mice±1 s.e.m. is depicted as a horizontal line in this graph. B, H, and S designate mice homozygous for the heal$^{b/b}$ allele from C57BL/6 , heterozygous for the heal$^{b/s}$ alleles from C57BL/6 and MRL/lpr, or homozygous for the heal$^{s/s}$ allele from MRL/lpr, respectively.

The Mouse Genome Database and associated literature were searched for potential candidates near the heal QTL (Table 4). The first locus, heal1, located on chromosome 8, is derived from C57BL/6 and is one of the strongest QTL of the five (p=0.0011), In the absence of contributing genes from MRL, C57BL/6 mice clearly cannot accomplish complete wound closure with heal1 alone. It has been shown that alleles that contribute to a trait from a parental strain that does not display that trait are not uncommon (46). Thus, it is not surprising that heal1 shows a strong additive effect with MRL loci in the F$_2$ (see FIG. 8). Candidate genes for heal1 (Table 4) in the strongest supported interval include the guanine nucleotide binding protein alpha 0, Gnao, an alpha subunit of a heterotrimeric G-protein which interacts with an activated G protein coupled receptor (Gp-cr), preceding downstream signaling (47). It is interesting to speculate that the basis of the additive interaction of heal1 with heal3 is an interaction between the gene products encoded by Gnao and the Gp-cr 18 found in the heal3 interval.

Though the method used for determining QTL cannot separate multiple loci in the same linkage group, we have observed highly suggestive LRS values for two regions of chromosome 13 in addition to the two QTLs identified (Table 2). That these may be unique QTLs is supported by the fact that they are separable from each other in phenotype congenics that have been generated (data not shown). One of these regions is located on chromosome 13, near marker D13nds1. Msx2 (also known as Hox8) is found in this interval and is expressed in regenerating amphibian tissue (48) as well as regrowing fingertips in neonatal mice (49). In this regard, we have evidence that Msx2 expression is different in healing ear tissue between MRL and B6 mice (Samulewicz et al, manuscript in preparation). This difference could be due to a polymorphism in the Msx2 gene itself, or to the indirect effect of an FGF signaling difference (50) mediated through the FGF receptor, FGFR4 (51), which is also encoded by a candidate gene located in this interval.

Heal4 is found on chromosome 15 near marker D15Mit244. The chromosome 15 QTL is strongly associated with the wound closure trait (p=0.0011) and is located in an area rich in candidate genes, including the gene encoding retinoic acid receptor gamma (Rarg), members of the keratin family which influence differentiation in the epidermis, as well as developmental genes known as homeobox and wnt genes. The retinoic acid pathway is known for its role in regeneration in amphibians (32, 34, and 52). Furthermore, the gamma subtype of the RAR displays preferential expression over the alpha and beta subtypes in skin and cartilage tissues (53), which is the site where the MRL/lpr healing trait is evaluated in the present study.

Finally, this set of genes does not include the fas gene, H-2, or any other gene known to play a role in the autoimmune profile of MRL/lpr mice. Several lines of evidence support this. First, our previous findings showed that the MRL/MpJ mice heal similarly to MRL/MpJ-Fas$^{lpr}$ mice (36). Secondly, intervals containing wound-healing genes in our crosses showed no overlap with those from another report on the genetic analysis of MRL/lpr autoimmune phenotypes (17). Third, we tested the lymph node cell number, a parameter associated with lymphoproliferation, of each of 101 $F_2$ mice in a regression comparison with their healing phenotype, and no association was found with the healing trait ($r^2$=0.0002, p=0.89) (Blankenhorn, et al., in preparation).

The MRL/lpr mouse strain was originally selected for its large size (13, 37); it was subsequently found to have a major defect in immune regulation, due to a retrotransposon insertion into the second intron of the fas gene (16, 54). This mouse exhibits immunological defects closely mimicking those of the human disease, systemic lupus erythematosus (SLE) and other lymphoproliferative disorders (14, 15). In the present study, however, none of the five healing QTLs nor the highly suggestive regions identified displays linkage to the fas gene or other genes proposed thus far to control the other autoimmune phenotypes seen in this strain of mouse.

EXAMPLE 10

Optic Nerve Regeneration in MRL Mice

Healer (MRL/+) and non-healer (C57Bl/6) mice were anesthetized and the optic nerve was cut using a microdissecting spring scissors from behind the left eye socket. The optic nerve was visually inspected to identify a cut end. The right eye was not touched. The mice were examined after 1.5 months.

Tissue from both the control right eye and the left eye where the optic nerve had been transected was removed, fixed in formalin, and embedded in paraffin. Serial sections were made and stained with hematoxylin and eosin. Several tissue sections were destained and restained with Bodian's silver stain to visualize axons.

Figure 9A:
FIG. 9A. The non-healer (B6) mouse exhibits complete atrophy of the left eye with marked sinking of the left eye socket compared to the normal untreated right eye.
Figure 9B:
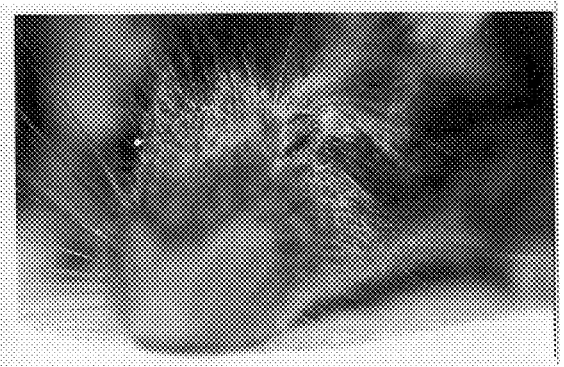
FIG. 9B. The healer (MRL) mouse exhibits only slight sinking of the left eye compared to the normal, untreated right eye.

In the all three non-healer mice the left eye had completely atrophied and had sunken into the eye socket while the control, right eye appeared normal (FIG. 9B). There was no evidence of eye-specific tissue in the left socket, although lacrimal gland tissue was present. The optic nerve near the eye and the chiasm had disappeared. Thus, there was no evidence of the presence of any part of the left eye or the associated optic nerve remaining in these animals.

In contrast, in all four healer mice the left eye had either only slightly sunken or was of normal size when compared to the right (control, non-treated) eye which was normal (FIG. 9A). The optic nerve could be found in both eyes of all four healer mice and the chiasm appeared normal. The right (control, non-treated) optic nerve appeared normal in each case.

Figure 10:
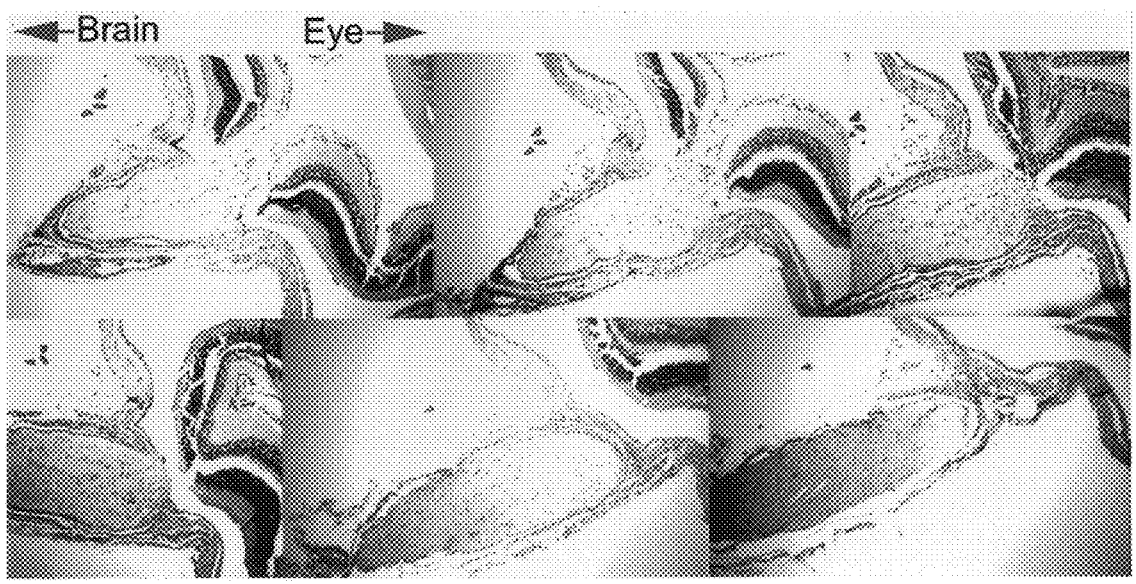
FIG. 10. Images depicting histological longitudinal sections of the healer (MRL) mouse uncut right eye-specific tissue. These serial sections were stained with hematoxylin and eosin.
Figure 11:
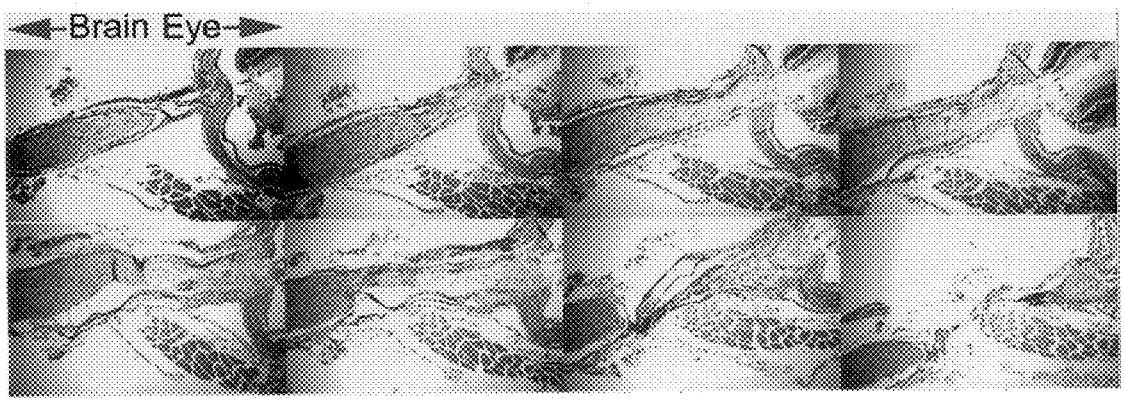
FIG. 11. A series of images depicting histological longitudinal sections of the healer (MRL) mouse cut left eye-specific tissue. These serial sections were stained with hematoxylin and eosin.

Histologic sections of eye-specific tissue from both healer and non-healer mice were examined 1.5 months after the optic nerve of each mouse's left eye had been surgically transected. In the healer mice, longitudinal serial sections of the right (control) eye tissue exhibited a normal, uncut optic nerve (FIG. 10). However, histologic sections of tissue from the left eye of healer mice demonstrated, in the first and last sections, a cut optic nerve (FIG. 11). More importantly, the middle histologic sections exhibited an increasing neural connection between the cut regions of the optic nerve. FIG. 11 shows an example of a restored optic nerve region as being thinner and irregular when compared with the uncut optic nerve of the (control, non-treated) right eye shown in FIG. 10.

Further, there appeared to be connective tissue and infiltrating macrophages filled with melanin as well as a proliferation of glial cells, especially oligodendrocytes, in the left eye-specific tissue of healer mice. Additionally, a blood vessel can be seen running along side the restored optic nerve in FIG. 11. This observation is important because cross-sections of uncut normal and healer optic nerves have blood vessels which run along side and are embedded into the optic nerve. These blood vessels would have been unavoidably cut upon transection of the optic nerve. Thus, it appears that the healer mice demonstrated regrowth of the blood vessels running along the restored optic nerve in addition to regeneration of the optic nerve itself.

Figure 12B:
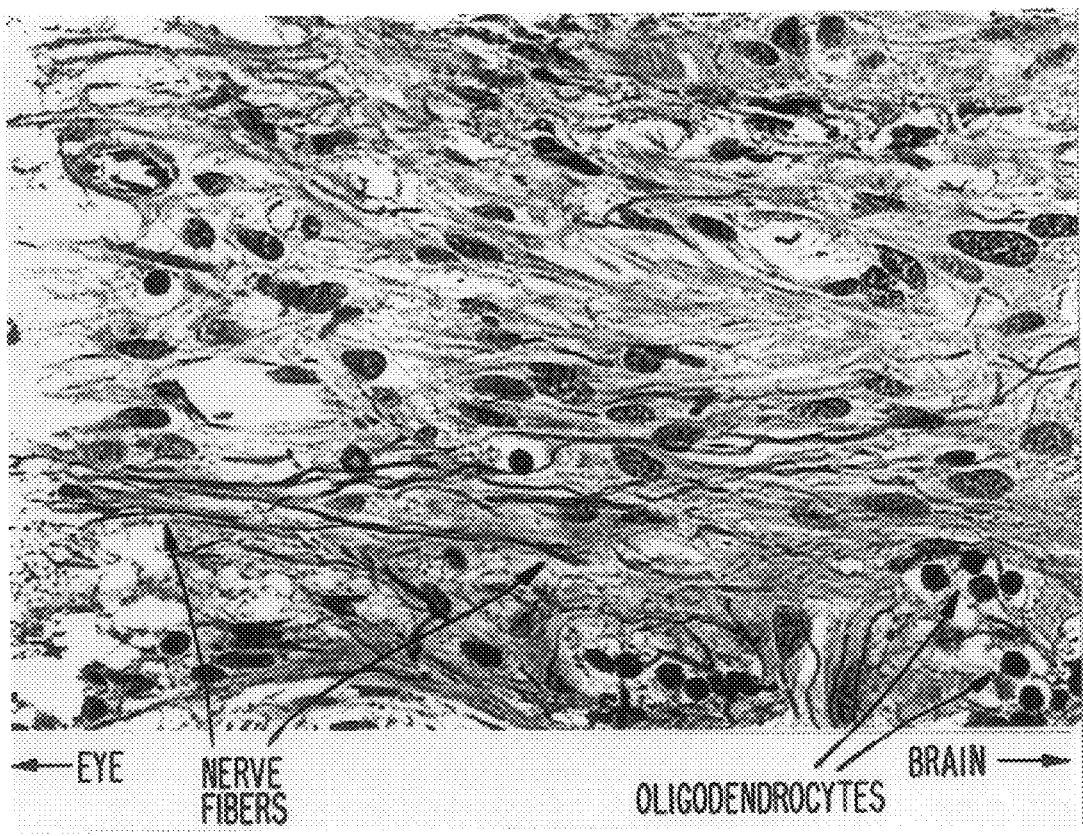
FIG. 12B is an image depicting a histological longitudinal section of the healer (MRL) mouse cut left eye-specific tissue. This section was stained with Bodian's silver stain specific for axons. The blue arrows indicate nerve fibers and the red arrows point to oligodendrocytes.

Several sections were then destained and restained to visualize axons with Bodian's silver stain. As can be seen in FIG. 12A, the healer uncut (right) eye has bundles of nerves woven through the optic nerve. On the other hand, the cut (left) healer optic nerve (shown in FIG. 12B) has a left optic nerve which appears to be generally depleted of nerve fibers. On the side of the healed optic nerve nearest to the eye, nerve fibers can be seen growing towards the brain. These fibers can be seen leaving a nerve cell body and having directionality (FIG. 12B). Near the newly grown nerve fibers are an abundance of oligodendrocytes.

Thus, healer MRL mice can regenerate nerve tissue. More specifically, all four MRL mice in which the left optic nerve was transected exhibited regrowth of the optic nerve within 1.5 months after transection. In these mice, the left optic nerve has clearly been cut but a neural connection was reestablished, with marked cellular proliferation including infiltrating macrophages filled with melanin and oligodendrocytes. Further, vascular connections had also been reestablished in the left healer eye as demonstrated by the presence of a blood vessel running along the side of the restored optic nerve. By comparison, the non-healer mice had no eye-specific tissue in the left eye socket and no nerve regeneration was detected.

Nerves which have been examined using the above-described procedures are the peripheral nerve, including the sciatic nerve, and central nervous system nerves including the optic nerve, brain stem and spinal cord.

EXAMPLE 11
Restoration of Function in MRL Mice Following Sciatic Nerve Crush Three strains of mice, C57BL/6, MRL and A/J, were examined after sciatic nerve crush. The percent of sensory function index (SFI), which is related to sciatic nerve function, is the comparison of the gait of the mouse having a normal left and a cut right sciatic nerve. To measure the SFI, the footpads of the animals were inked, and the animals were allowed to walk on a paper pad in a housing which forces them to walk forward. The pattern of ink deposition is directly related to the SFI, which was then calculated for each mouse.

The results of these experiments are shown in FIG. 13. Significant recovery of sciatic nerve function was observed in MRL mice (50% of 2/3 mice) at day 30. In contrast, C57BL/6 and A/J mice exhibited an average negative SFI value, indicating that the sciatic nerves in these animals did not recover.

EXAMPLE 12
Involvement of T Cells in Healing in Aged Healer Mice

Figure 17:
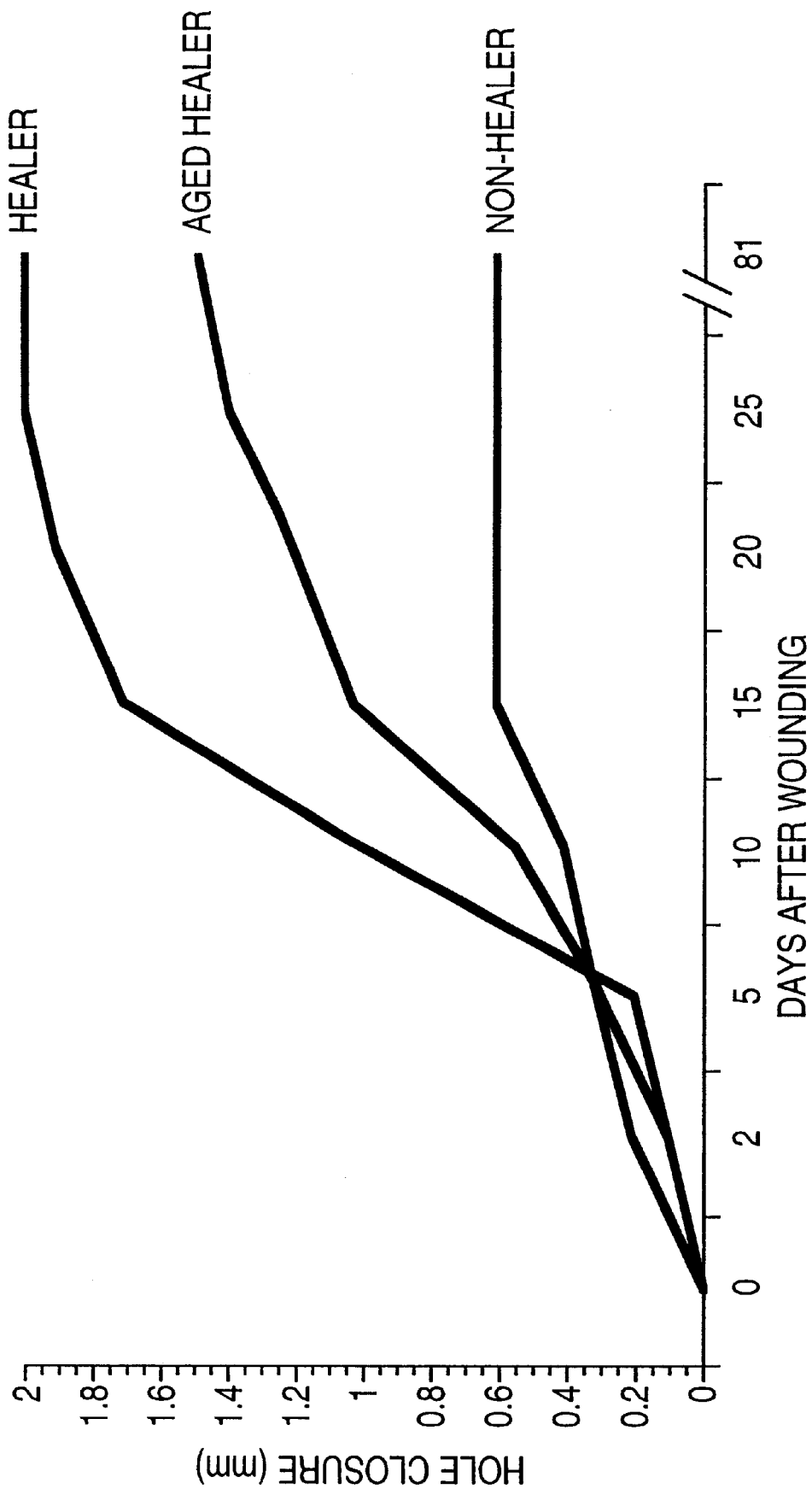
FIG. 17. Graph showing the effect of age on the time course of ear hole closure in healer mice.

Several facts indicated that T cells might play a role in wound healing in aged healer mice. First, scarless healing occurs in fetal mice until embryonic day 16, when T cells develop in the thymus. Second, in MRL/lpr mice, the number of lymphocytes increases with age. Third, aged healer mice do not heal as well as younger healer mice (FIG. 17). We therefore examined the role of T cells in the enhanced healing response of these mice in two ways.

Figure 18:
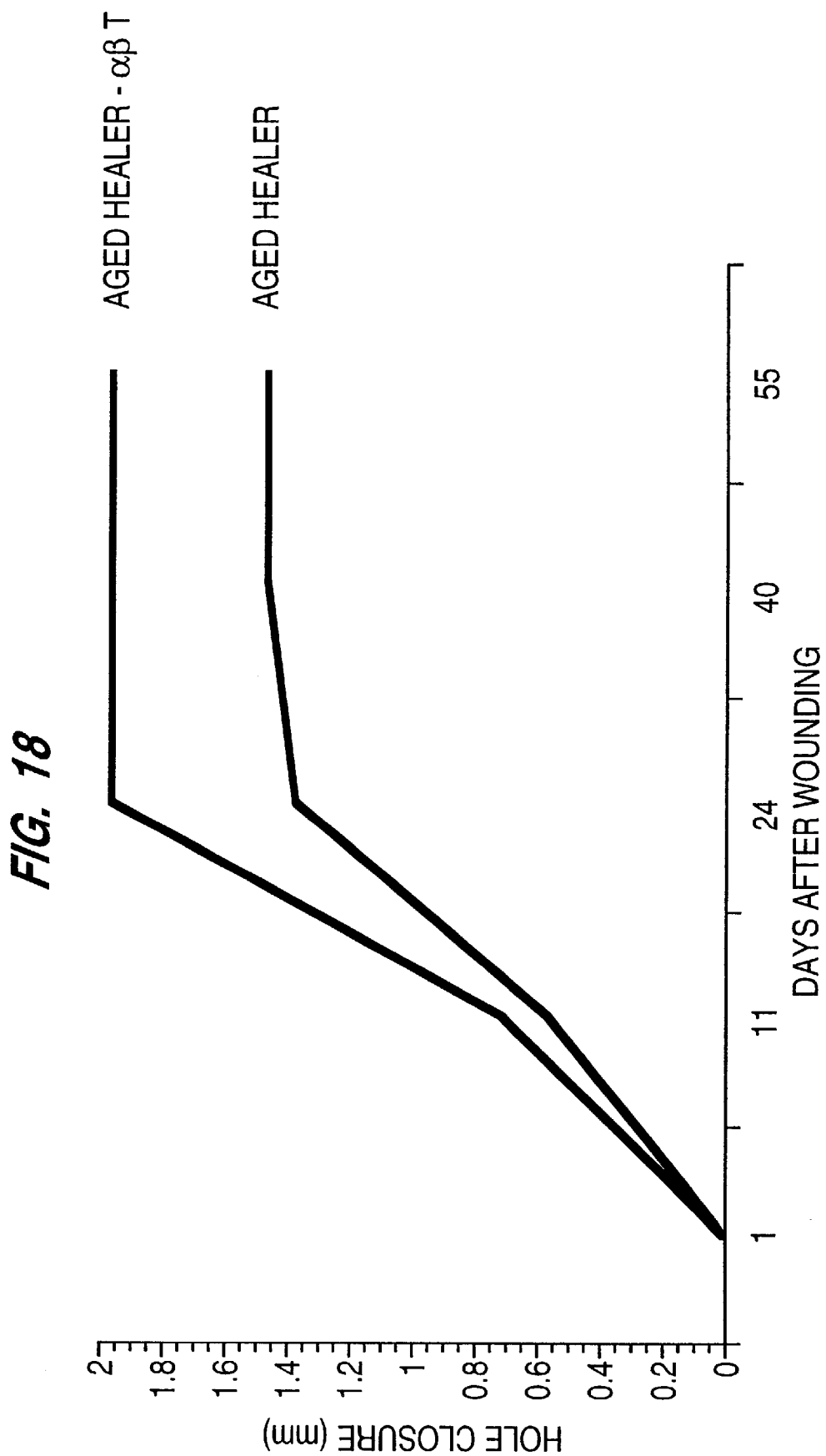
FIG. 18. Graph demonstrating that T cell depletion leads to complete healing in aged healer mice.

First, we treated aged (5 month-old) healer mice with antibodies against T cell receptors and punched a 2 mm ear hole in the treated aged mice. As measured by this assay, aged mice which were treated with anti-TCR antibodies became complete healers, similar to their younger counterparts (FIG. 18).

Figure 19:
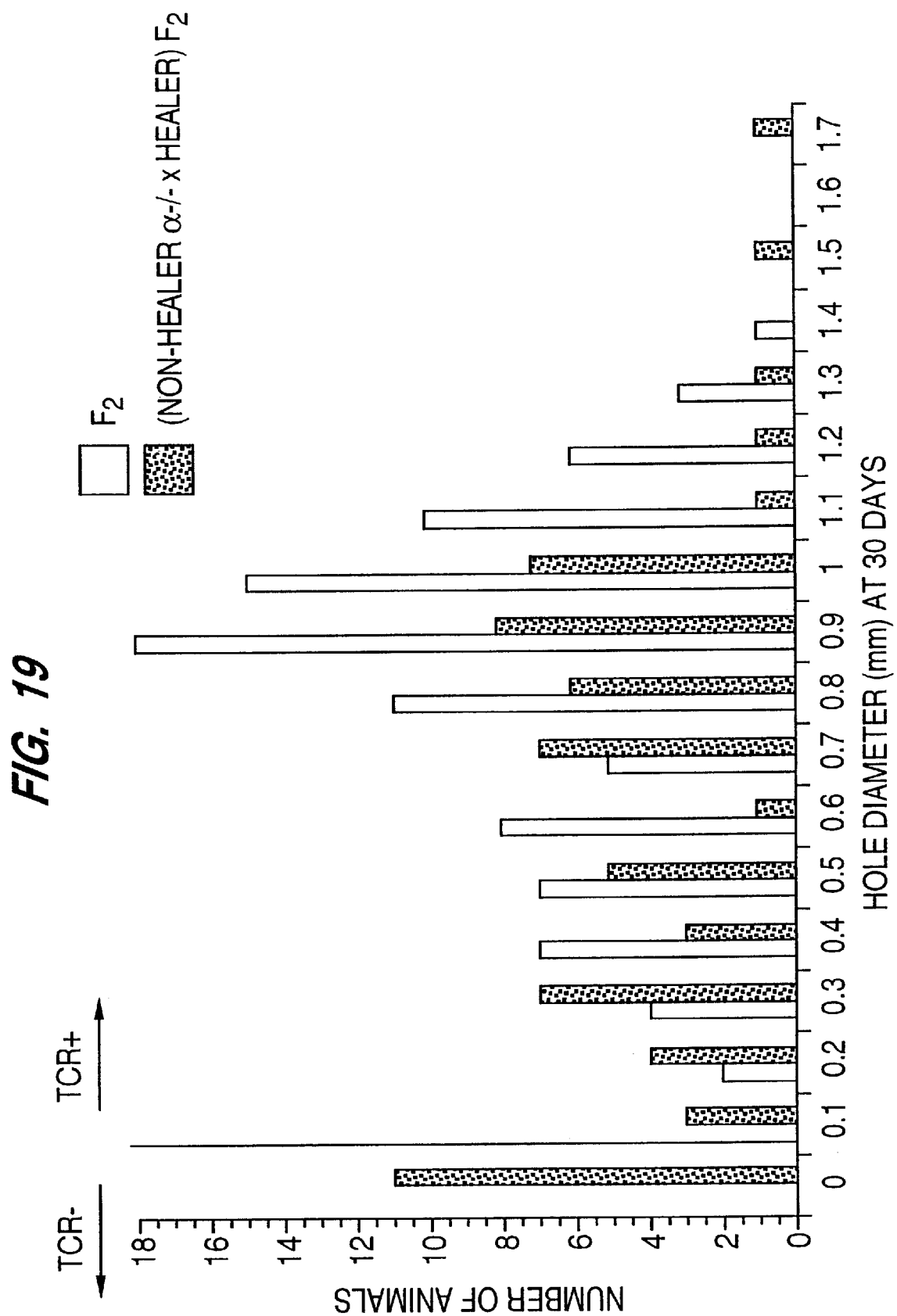
FIG. 19. Bar graph demonstrating that T cell receptor knock-outs show enhanced healing.
Figure 21A:
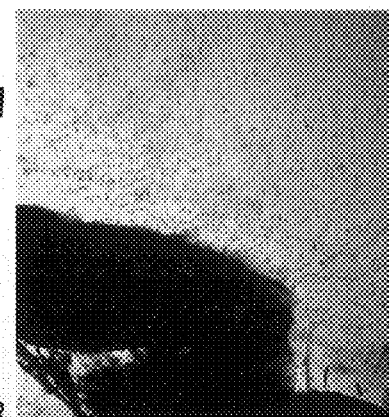
FIG. 21A, explant of a healer mouse ear punch.
Figure 21B:
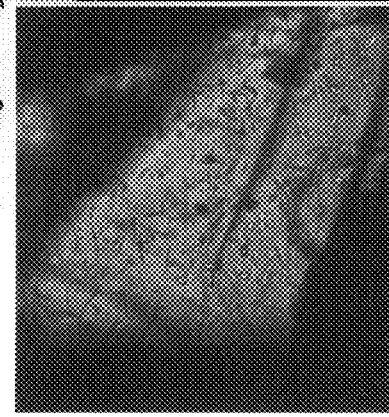
FIG. 21B, magnified view of the healer mouse ear punch explant.
Figure 21C:
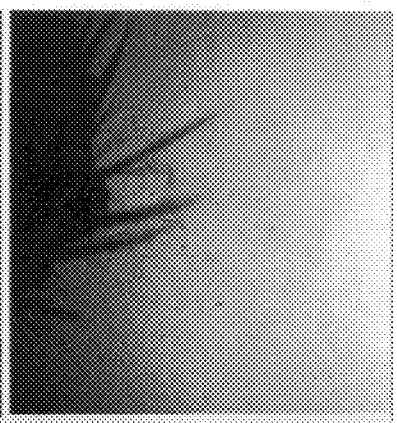
FIG. 21C, explant of a non-healer mouse ear punch.
Figure 21D:
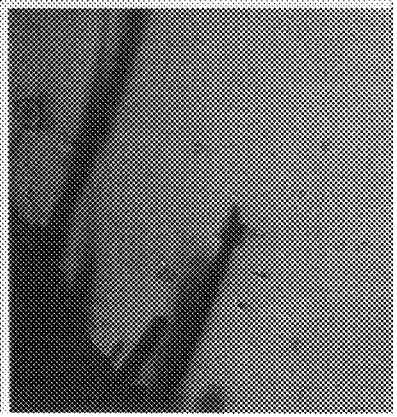
FIG. 21D, magnified view of the non-healer ear punch explant.

Second, we crossed a member of the $F_1$ generation from a cross between a healer and a non-healer mouse whose T cell receptors had been genetically eliminated, or "knocked out." Members of the resulting $F_2$ generation were then examined for a healer phenotype using an ear punch assay and for the presence of T cells by flow cytometry. Approximately 12% of the $F_2$ generation had no T cells and were complete healers. (FIG. 19).

These results suggest that T cells somehow suppress the healing response in aged healer mice and that elimination of functional T cells restored the healing capacity of the mice. T cells obtained from non-healer mice can now be transferred into healer mice to determine whether the T cells, or a particular population of the T cells, have an effect on the enhanced wound healing of healer mice.

EXAMPLE 13
Adoptive Transfer of Fetal Liver Cells from Healer Mice into X-irradiated Non-healer Recipients Enhances Wound Healing C57BL/6 mice were lethally irradiated. After 24 hours, each mouse received an injection of fetal MRL liver cells into the tail vein. Ear punches were performed at 2, 4, and 6 months after injection of the liver cells.

No healing was observed in the ears of mice after 2 or 4 months. After 6 months, however, ear holes of the C57BL/6 (non-healer) mice exhibited a healing response. This response was correlated with the detection of chimeric cells in the thymus and/or lymph node of the mice, as shown in FIG. 20.

Thus, it is possible to transfer the ability to heal ear holes to adult non-healer mice using adoptive transfer of fetal liver cells from a healer mouse strain.

Figure 14:
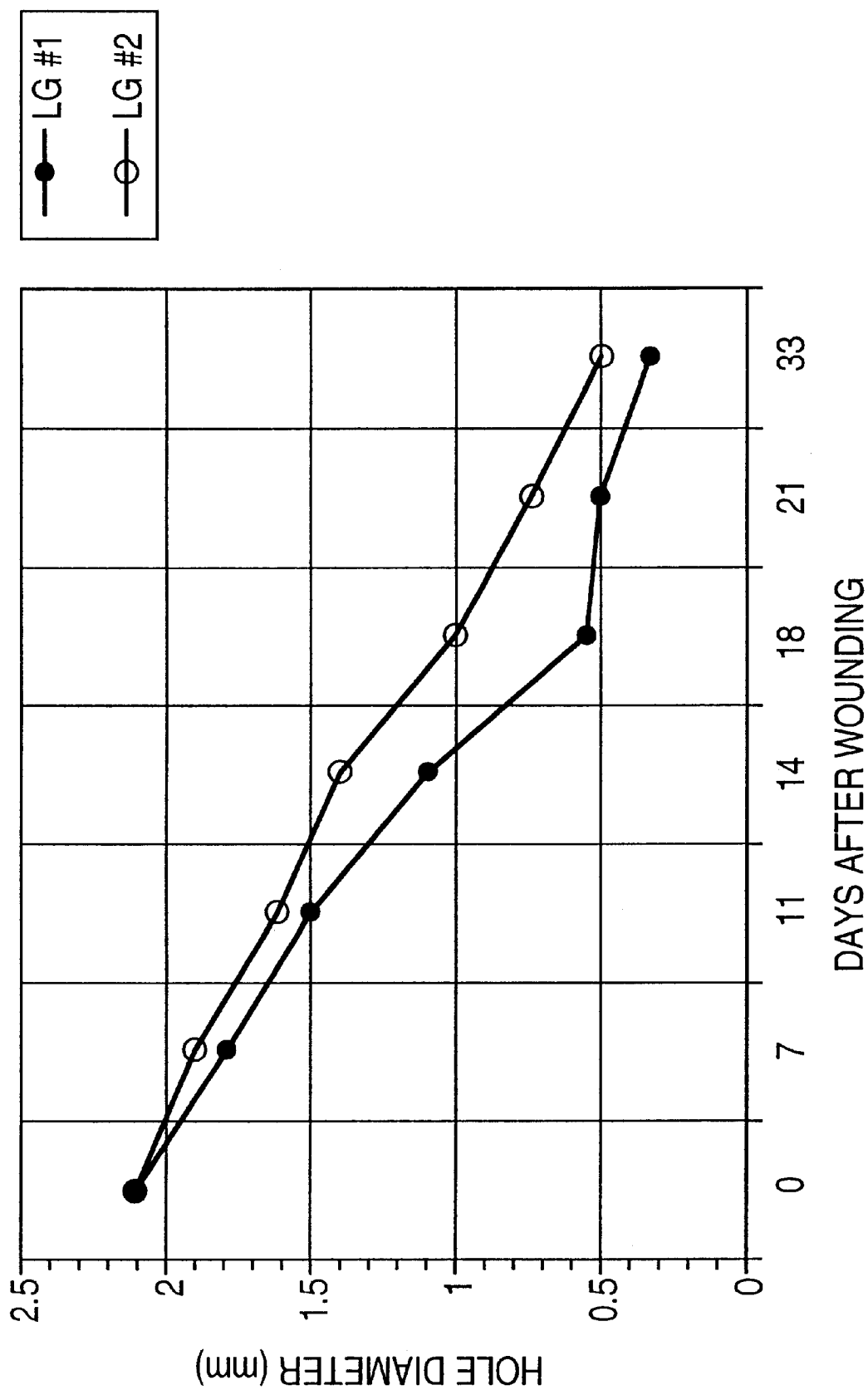
FIG. 14. Graph depicting healing of ear holes in LG mice.

EXAMPLE 14
Adoptive Transfer of Macrophages Obtained from Healer Mice to Non-healer Mice Recipients Enhances Wound Healing The MRL mouse is derived from crossbreeding of LG (75%), AKR (12%), C3H (12%) and C57BL (0.3%) mice. Wild type strains of these mice were tested for their ability to heal or to partially heal 2 mm ear hole wounds. The only mouse which exhibited partial healing was the LG mouse (FIG. 14). The experiment was conducted as described herein for the MRL mouse.

Normal C57BL/6 mice were injected intraperitoneally with macrophages obtained from healer mice at the time of ear punching of the non-healer mice. The macrophages which were transferred were five day thioglycollate induced peritoneal cells obtained from an (MRL×B6)$F_2$ T cell receptor alpha chain knockout mouse. This mouse was used because the $\alpha\beta$+T cells were absent and the cells were only partially allogeneic.

Figure 15:
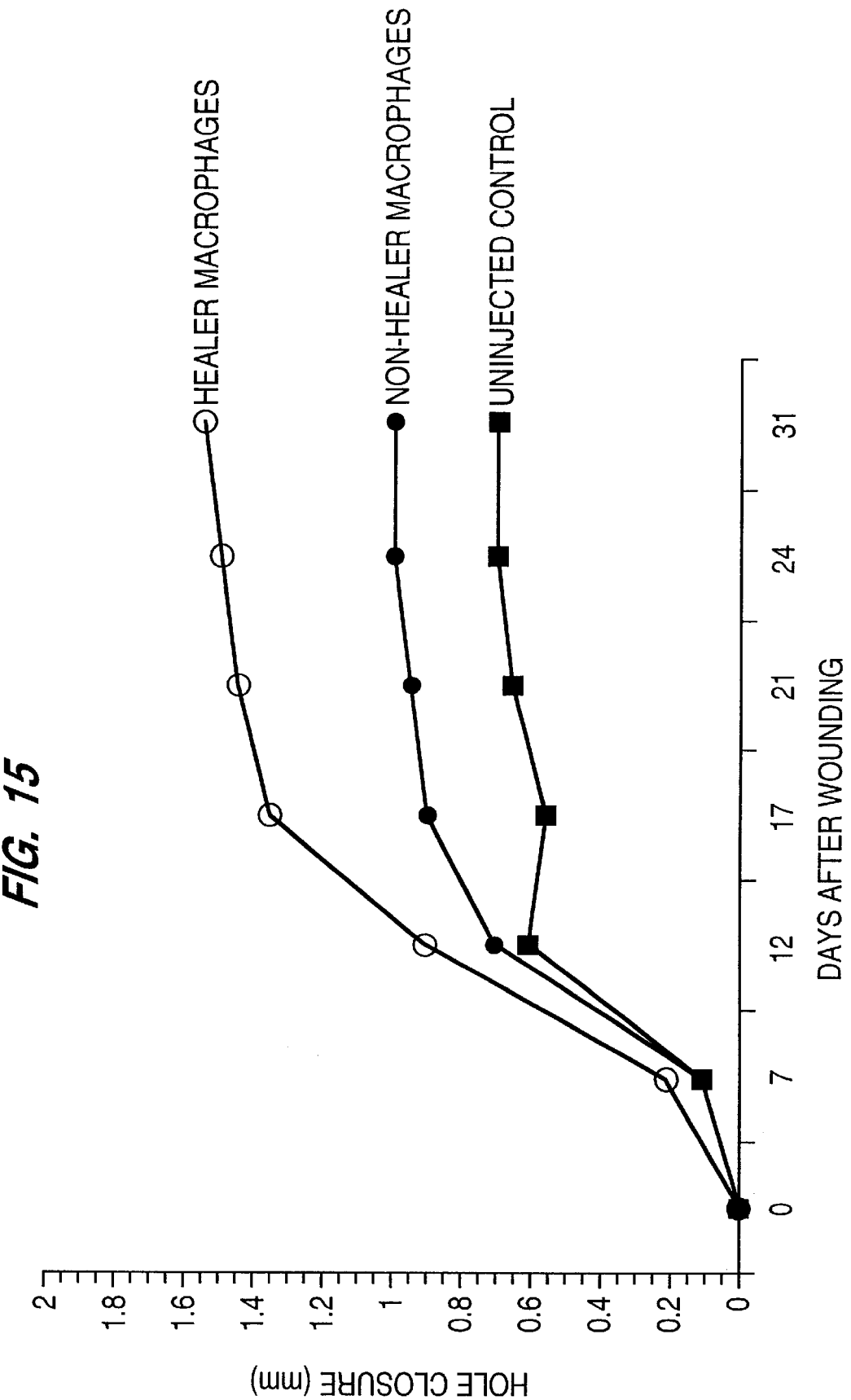
FIG. 15. Graph depicting adoptive transfer of the healing ability of MRL mice, wherein macrophages obtained from healer mice were transferred to non-healer mice.
Figure 16A:
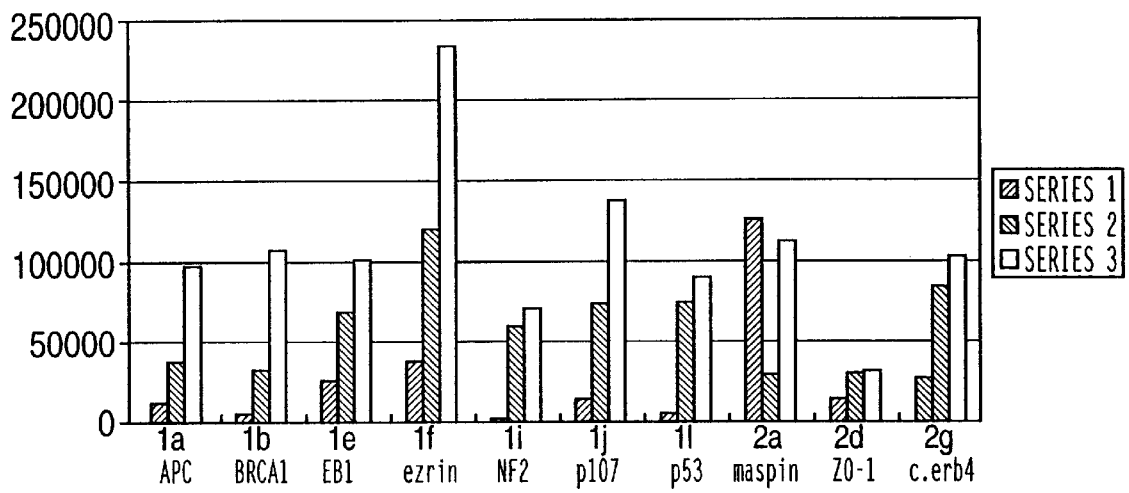
FIG. 16. Results from microarray analysis of gene expression in MRL mice after ear punch. Series 1, no ear punch; Series 2, 24 hours after ear punch; Series 3, 40 hours after ear punch. Names of genes are given in Table 11.
Figure 16B:
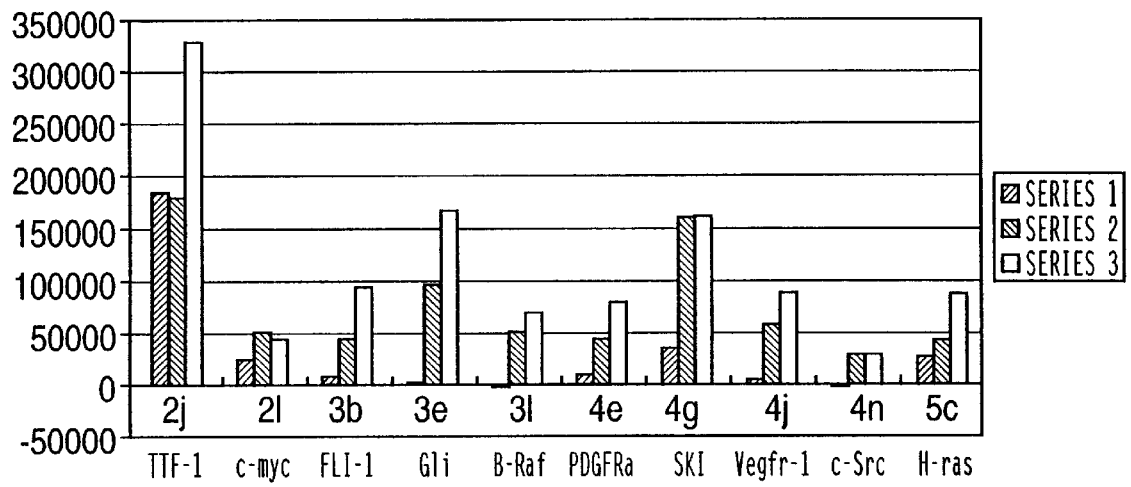
Figure 16C:
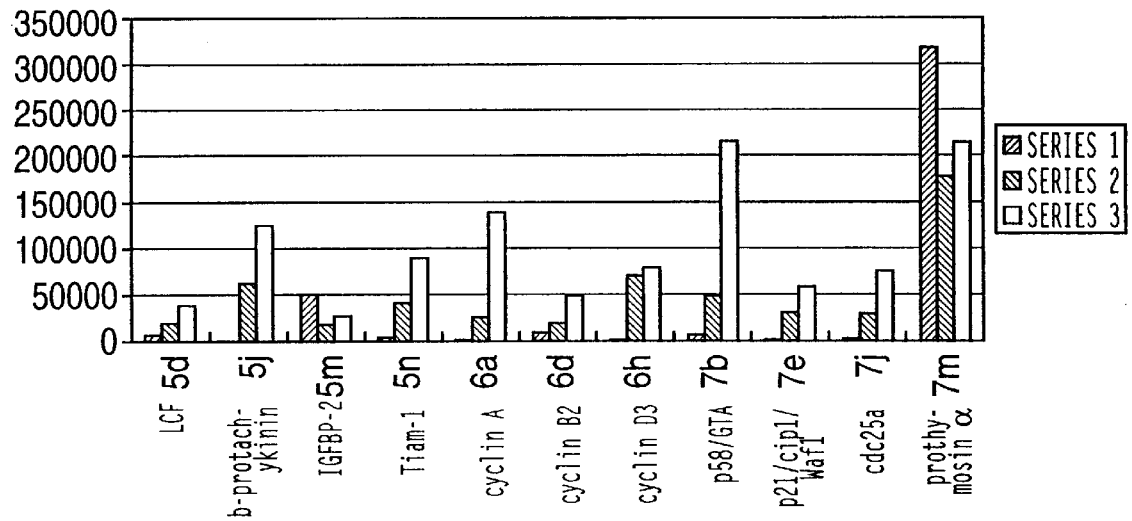
Figure 16D:
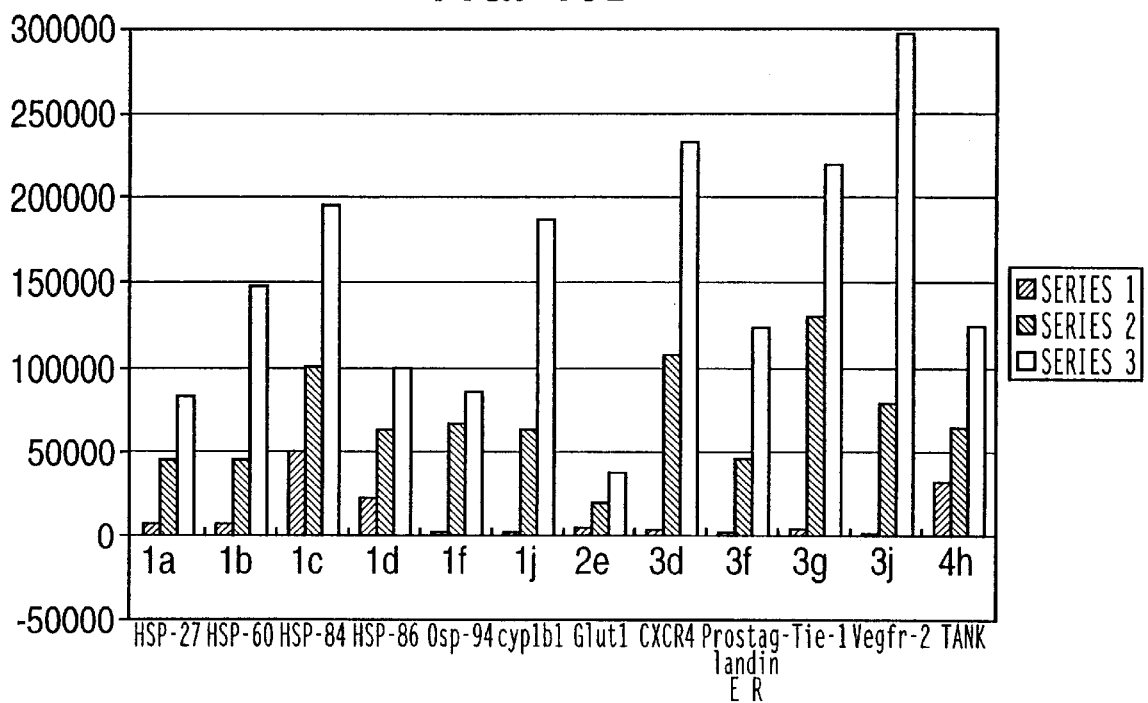
Figure 16E:
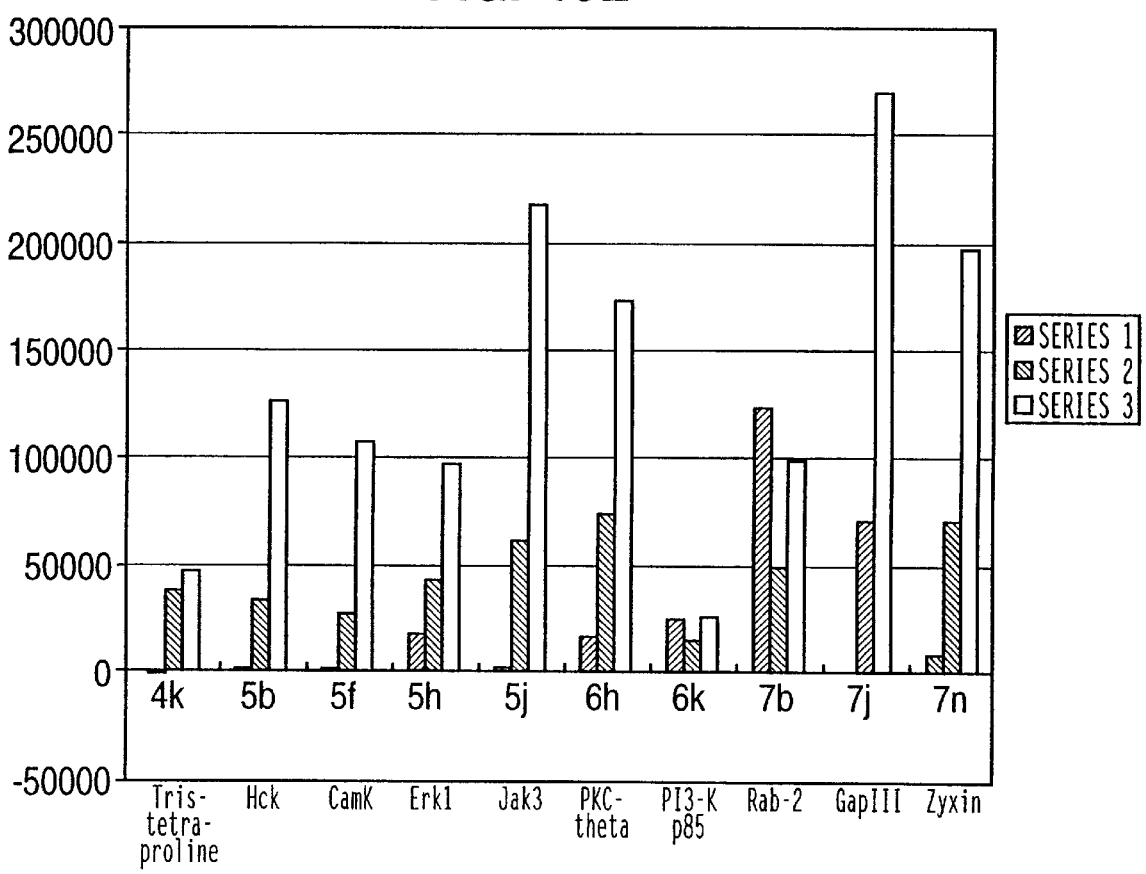
Figure 16F:
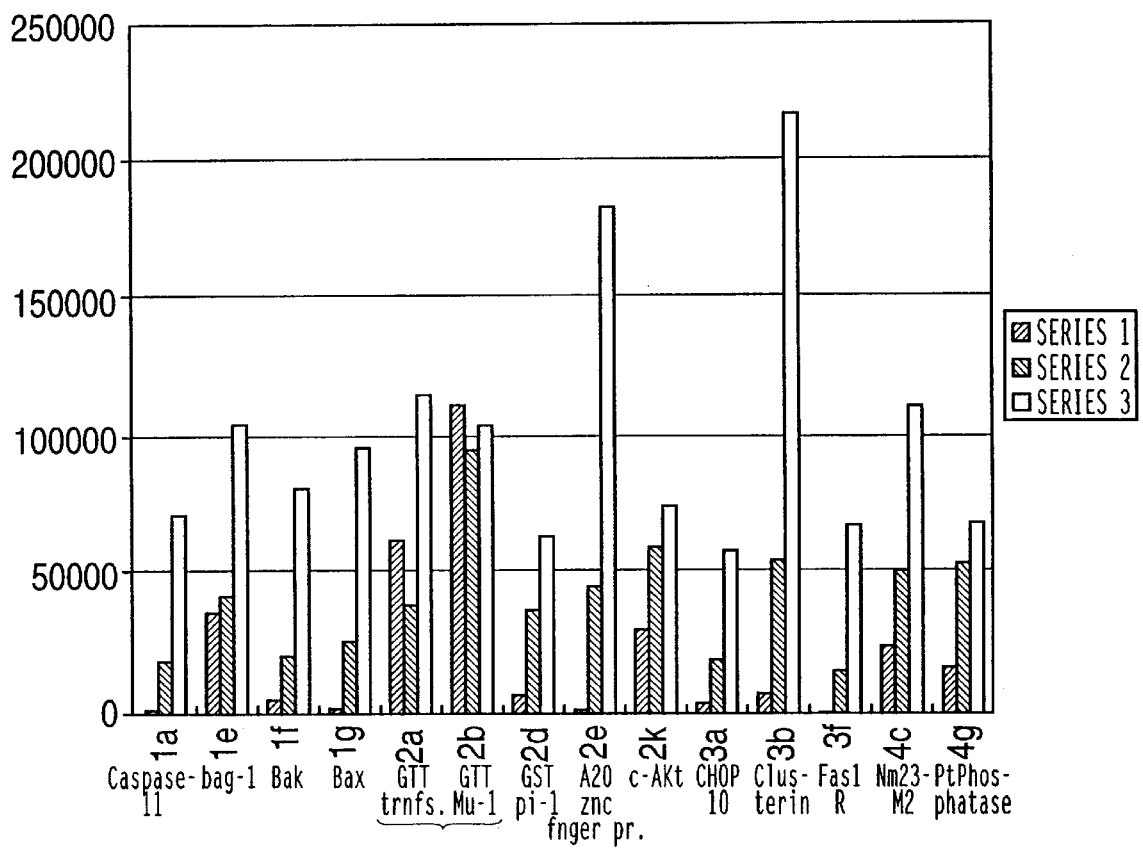
Figure 16G:
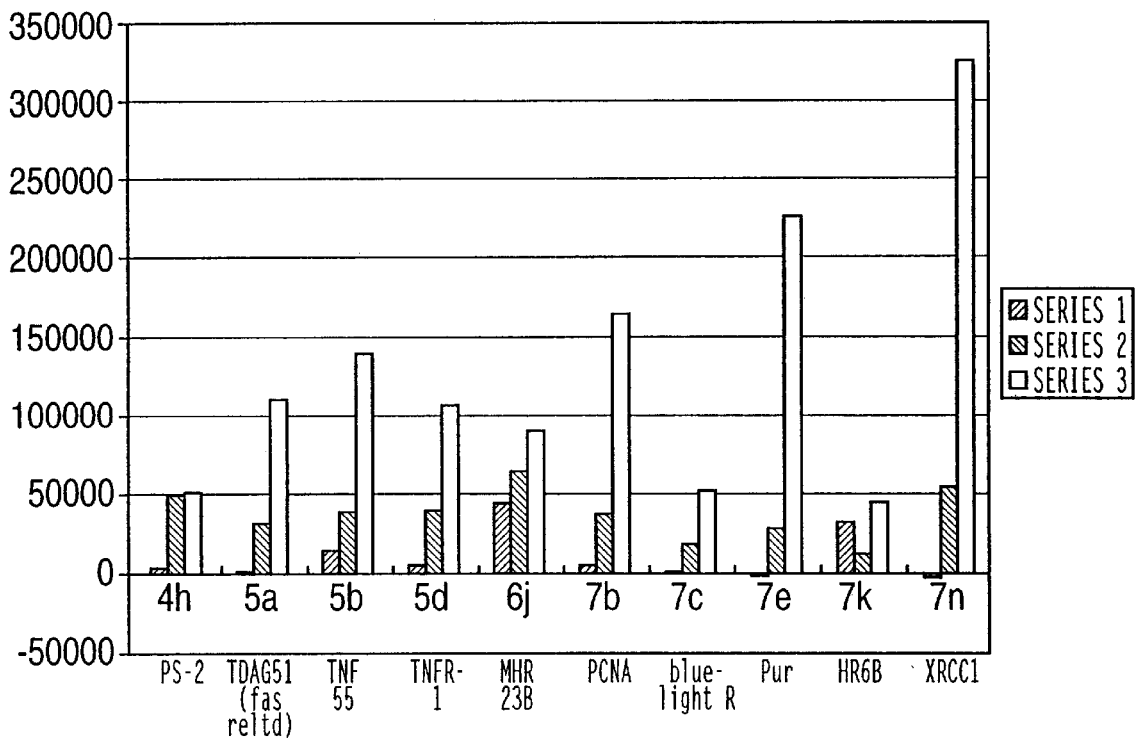
Figure 16H:
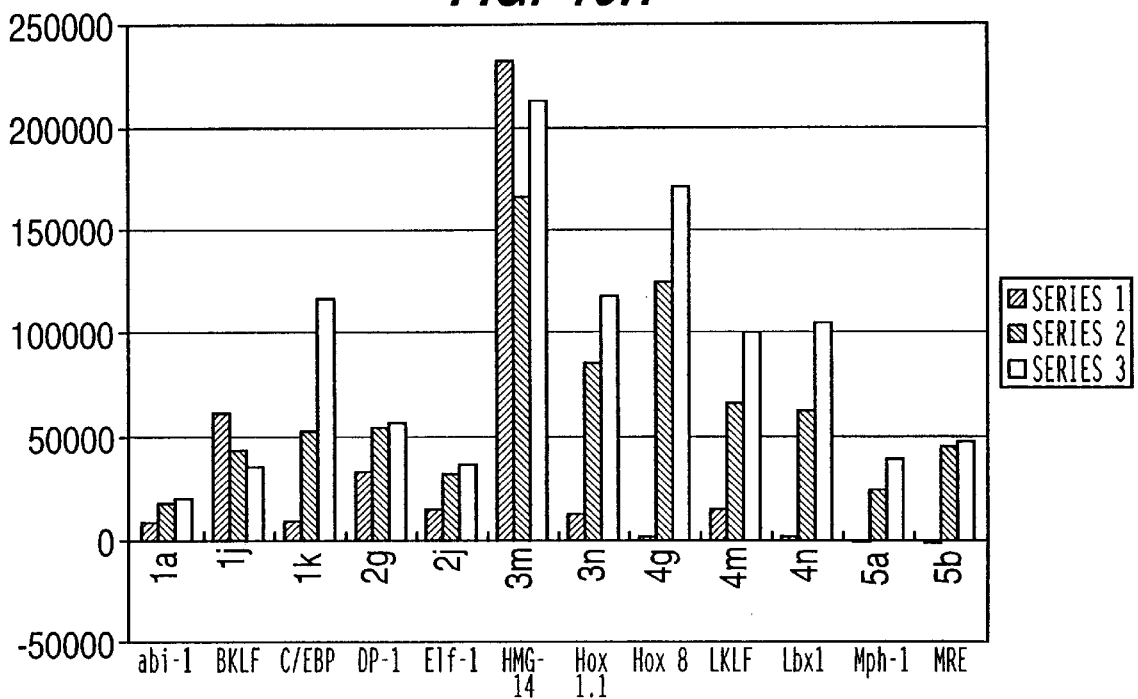
Figure 16I:
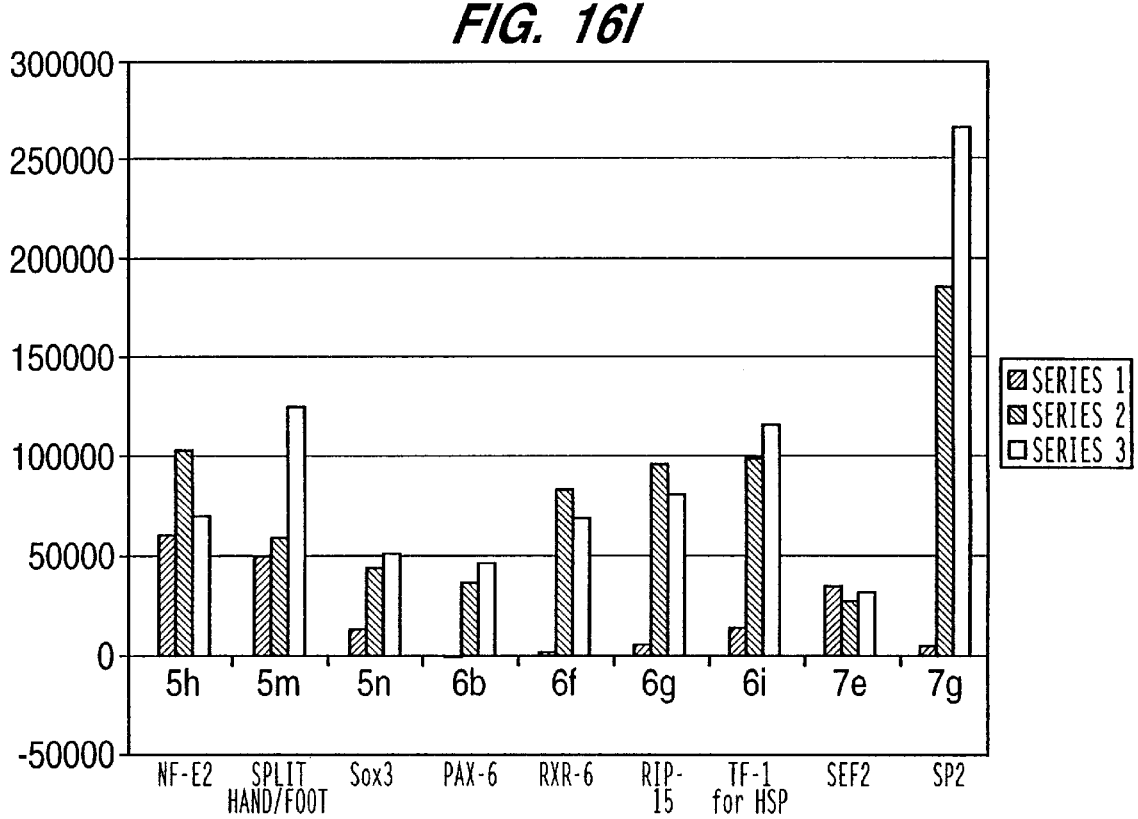
Figure 16J:
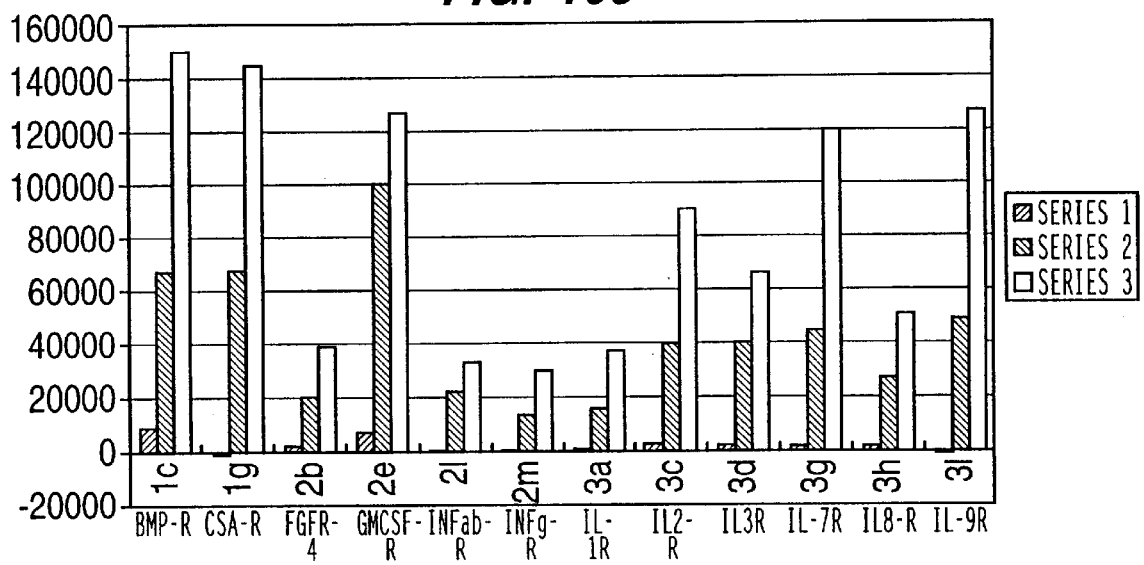
Figure 16K:
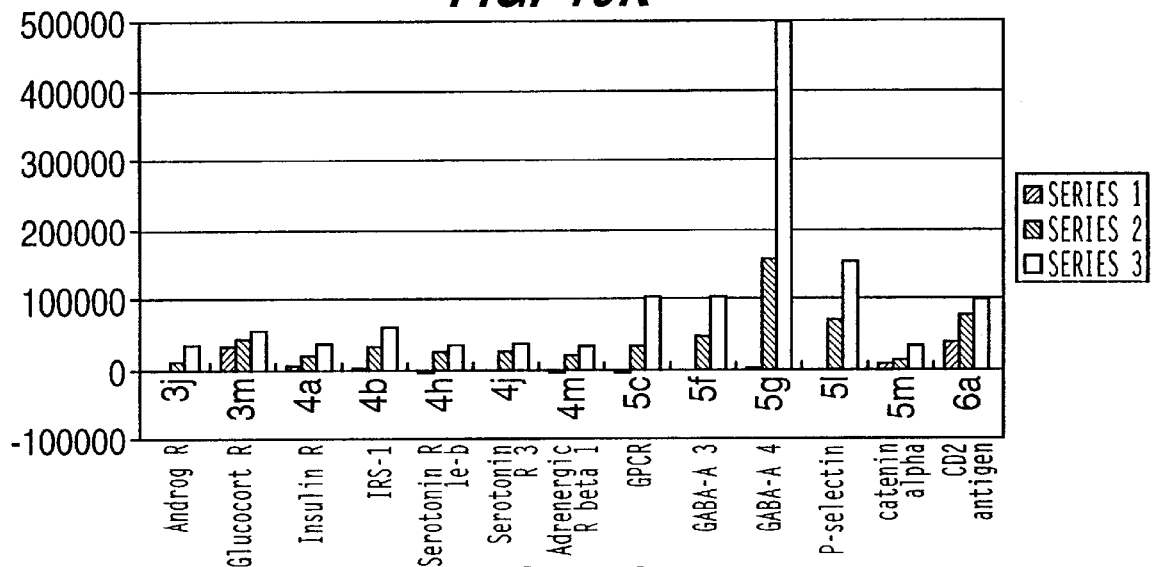
Figure 16L:
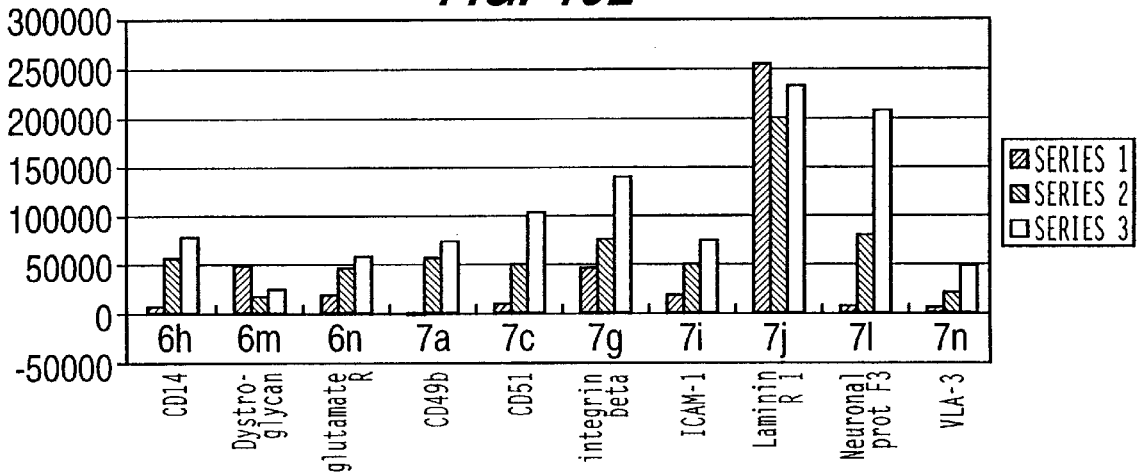
Figure 16P:
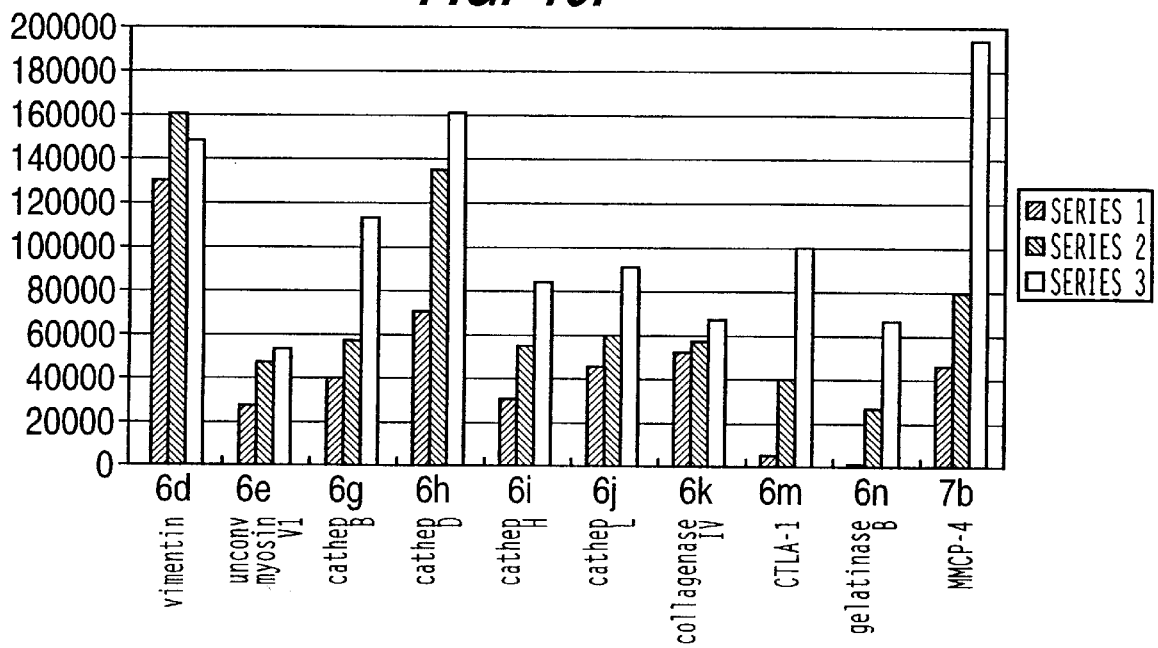
Figure 16Q:
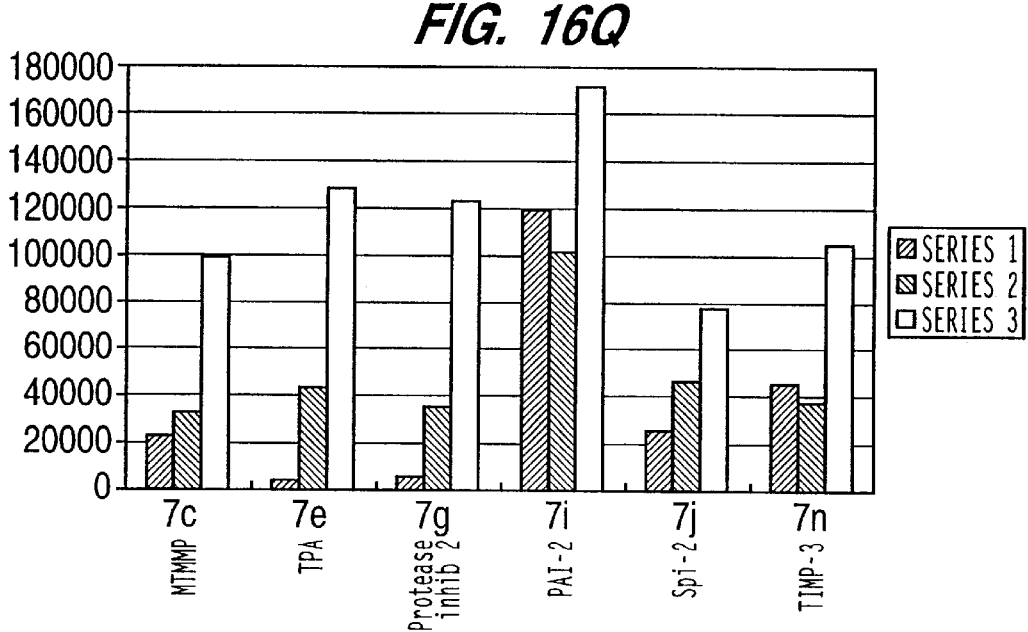

Macrophages were obtained from healer mice using standard procedures, selected by adherence to plastic, and transferred to non-healer mice. Uninjected non-healer mice and non-healer mice injected with non-healer macrophages served as controls in the experiment. Ear hole closure was measured during the 30 days after wounding. The results of the experiment are shown in FIG. 15.

Healer macrophages induced the best ear closure (greater than 75%) in non-healer mice. (FIG. 21). Macrophages which were obtained from non-healer mice and which were transferred into non-healer mice were unable to confer healing on non-healer mice. These results establish that tissues and cells obtained from healer mice can be used to confer healing ability on non-healer mice.

EXAMPLE 15
Functional Recovery of Healer Mice Following Complete Transection of the Spinal Cord A complete transection of the spinal cord at thoracic level (TH9-TH11) was made in MRL and in C57BL/6 mice anesthetized with ketamine/xylazine (100/15 mg/kg, i.p.). A dorsal median incision was made over the lower thoracic vertebra. Retractors were placed in the wound to allow surgical manipulation. After exposing the vertebral arch and the spinous processes by retracting the medial part of the autochtone musculature, the osseous parts of one vertebral bone were removed with a milling cutter, leaving the dura mater intact. After continuous cooling of the spinal cord with ice cold isotonic saline to minimize bleeding, transection was performed with a scalpel. In some mice, a portion of the spinal cord was removed, rather than simply cut. In these mice, more of the spinal cord is exposed, by removing only the caudal part of the more cranial vertebral arch. The cranial part of the more caudal vertebral arch was also be removed to minimize vertebral instability. Two transections were performed, and the tissue between the transections was removed with a fine forceps.

Ice cold isotonic saline was then applied in pulses until no bleeding occurred. The muscles of both sides were repositioned and gently opposed by single 8-0 resorbable sutures. The skin was closed in the usual manner with single sutures using 8-0 Dexon (Polyglycolic Acid).

Animals were weighed daily to ensure proper water and nutritional intake. Food and water was made available at ground level through a special device. In the first postoperative days, each mouse was watched carefully for its ability to eat and drink, unless it was fed manually. The bladder was emptied 3 times a day by applying gentle pressure to the abdomen. The mice were also carefully watched for potential injury and self mutilation due to loss of innervation of the hind limbs.

After 2 days of postoperative recovery, the mice were examined for loss of lower limb innervation. Both strains showed no innervation of the hind limbs, which were dragged behind. After 2 weeks, neither strain of mice showed signs of innervation of the hind limbs. Between seven and nine weeks, however, MRL mice regained partial proximal innervation of the tail and lower limbs, exhibiting the ability to flex and then extend their hind legs. C57BL/6 mice continued to show no movement of the hind limbs or tail and to show degeneration of the limb musculature and fixed flexion of the joints. In contrast, fixed flexion of the joints of the MRL mice never occurred, and only minor muscle degeneration was in the observed first month.

Histological examination revealed that MRL mice produced only a minor scar between the two ends of the transected spinal cord (2–5 cell layers), whereas C57BL/6 mice produced a conventional glial scar (10–15 cell layers), thereby preventing the spinal cord to reconnect on an axonal level.

The partial functional recovery in MRL mice, as well as the underlying histomorphology, suggests that regeneration and reconnection on the axonal level of the spinal cord of MRL mice can occur after complete transection of the spinal cord.

EXAMPLE 16

Differential Expression of Genes in Dendritic Cells of Healer and Non-healer Mice Dendritic cells (immature macrophages) were isolated from the bone marrow of adult C57BL/6 and MRL$^+$ mice using standard procedures. Total RNA was isolated from the dendritic cells and subjected to microarray analysis, as described above in the Materials and Methods section.

Table 15 shows genes whose expression was increased more than 50% in either MRL$^+$ or C57BL/6 mice. The gene names and array locations are from the Clontech web site, available at the URL address: http file type, www host server, domain name clontech.com, chlontech/JAN98UPD/Atlaslist directory.

EXAMPLE 17

An in vitro assay of wound healing.

A hole was punched in the ear of a healer and a non-healer mouse. Two days later, an explant of the ear tissue, including the punched hole, was excised, embedded in a collagen gel, and maintained in vitro.

Figure 22:
FIG. 22. Magnified view of the area around a healer mouse ear punch explant, demonstrating migration of cells away from the explant.
Figure 23:
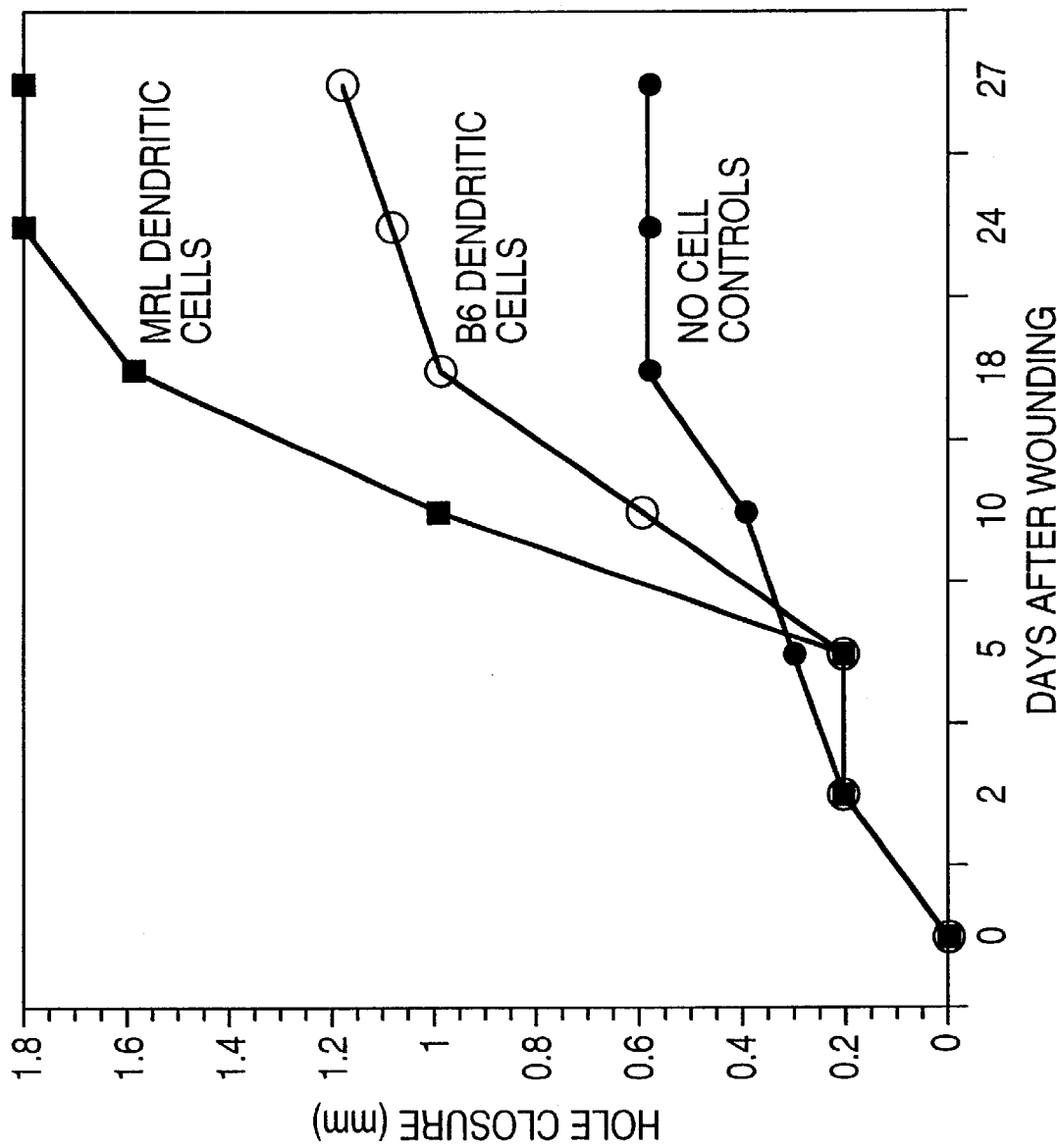
FIG. 23. Graph demonstrating that adoptive transfer of bone marrow-derived dendritic cells into ear-punched C57BL/6 Rag$^{-/-}$ immunodeficient mice enhances wound healing.

FIG. 22 shows explants of healer (FIGS. 22A, B) and non-healer (FIGS. 22C, D) ear punch explants in vitro. FIG. 23 shows cells migrating away from the explant of the healer ear punch, possibly in response to factors which are produced by the wounded ear.

EXAMPLE 18

Adoptive Transfer of Bone Marrow-derived Dendritic Cells from Healer Mice into Non-healer Immunodeficient Mice Enhances Healing Dendritic cells were isolated from healer (MRL$^+$) and non-healer (C57BL/6) mice as described in Example 16. C57BL/6Rag$^{-/-}$ mice, which are immunodeficient and unable to reject the dendritic cells, were ear-punched to make a 2 mm hole and immediately injected intraperitoneally with dendritic cells of either MRL$^+$ or C57BL/6 mice. Ear hole closure was measured at 0, 2, 5, 10, 18, 24, and 27 days after wounding. The results of this experiment are shown in FIG. 23.

Healer dendritic cells induced the best ear closure (approximately 90%) in the non-healer mice, demonstrating that the healer dendritic cells can be used to transfer enhanced healing ability to non-healer mice.

EXAMPLE 19

Segregation of Quantitative Trait Loci in Phenotype Congenic Mice.

Congenic mice were generated by six successive backcrossings of the $F_1$ generation of a healer (MRL) x non-healer (C57BL/6) cross with its non-healer parent strain. Segregation of quantitative trait loci was examined in healer phenotype congenic mice (see Examples 5–8, above). Each of the 17 phenotype congenic mice examined healed a 2 mm ear hole from at least 75% to 100% 30 days after punching.

Table 16 shows that only certain markers segregate with the healer phenotype in these phenotype congenic mice. These mice are therefore useful for dissecting out the minimum number of chromosomal loci and genes involved in enhanced wound healing.

TABLE 1

Residual wound size

| Parental Strains and hybrid | | Backcross and intercross progeny | |
|---|---|---|---|
| C57BL/6 | 1.10 ± 0.27 | F1 x MRL/lpr | 0.35 ± 0.27 |
| MRL/lpr | 0.04 ± 0.06 | F1 x B6 | 0.95 ± 0.25 |
| (MRL x B6)F1 | 0.73 ± 0.22 | (MRL x B6)F2 | 0.83 ± 0.28 |

Numbers are the diameter of holes in mm ± standard deviation (SD) on day 28–30. F1 = (MRL x C57BL/6)F1 hybrid.

TABLE 2

Location of heal QTL as determined in the intercross (F2) and the backcross (BC1) progeny.

| MGD cM | Primers | F2 LRS[1]- | F2 p value | BC1 LRS[2]- | BC1 p value | QTL |
|---|---|---|---|---|---|---|
| 71.5 | D1Mit288 | 6.1 | 0.0130 | | ns | |
| 105 | D2Mit148 | | nd | 4.8 | 0.0279 | |
| 55.6 | D4Nds2 4.2 | 4.2 | 0.0400 | | ns | |
| 77.5 | D7Mit127 | 5.5 | 0.0190 | | ns | |
| 52.4 | D7Mit220 | | ns | 10.2* | 0.0014 | |
| 21 | D8Mit191 | | ns | 6.4 | 0.0115 | |
| 33 | D8Mit132 | 5.5 | 0.0188 | | ns | |
| 37 | D8Mit249 | 7.3 | 0.0069 | | ns | |
| 49 | D8Mit211 | 10.7 | 0.0011 | | ns | heal1* |
| 56 | D8Mit166 | 7.3 | 0.0068 | | nd | |
| 34 | D12Mit4 | | ns | 7.1 | 0.0077 | |
| 52 | D12Mit233 | 6.1 | 0.0137 | 9.4 | 0.0022 | |
| 52 | D12Mit132 | | nd | 10.9 | 0.0009 | heal5*# |
| 9 | D13Mit135 | 9.4 | 0.0022 | 4.8 | 0.0290 | |
| 11 | D13Mit115 | 9.7 | 0.0019 | 5.0 | 0.0261 | heal2*# |
| 13 | D13Mit116 | 8.7 | 0.0030 | 5.1 | 0.0230 | |
| 30 | D13Mit245 | 7.5 | 0.0335 | | nd | |
| 32 | D13Nds1 | 10.2* | 0.0014 | | ns | |
| 44 | D13Mit126 | 7.4 | 0.0065 | | ns | |
| 44 | D13Mit191 | 10.2* | 0.0014 | | ns | |
| 47 | D13Mit29 | 6.5 | 0.0101 | | nd | |
| 48 | D13Mit107 | 7.4 | 0.0064 | | ns | |
| 49 | D13Mit144 | 6.9 | 0.0088 | | nd | |
| 60 | D13Mit129 | 10.8 | 0.0010 | 8.3 | 0.0040 | heal3*# |
| 62 | D13Mit53 | 10.5 | 0.0012 | 7.1 | 0.0077 | |
| 71 | D13Mit151 | 8.2 | 0.0042 | 4.6 | 0.0318 | |
| 54.5 | D15Mit171 | 6.6 | 0.0104 | | nd | |
| 55.6 | D15Mit242 | 7.1 | 0.0079 | | nd | |
| 57.8 | D15Mit172 | 7.3 | 0.0070 | | nd | |
| 56.8 | D15Mit244 | 10.7 | 0.0011 | | nd | heal4* |

TABLE 2-continued

Location of heal QTL as determined in the intercross (F2) and the backcross (BC1) progeny.

| MGD cM | Primers | F2 LRS[1]- | F2 p value | BC1 LRS[2]- | BC1 p value | QTL |
|---|---|---|---|---|---|---|
| 56.8 | D15Mit14 | 8.5 | 0.0035 | | ns | |

Underlining indicates the LRS values that were used for assigning heal QTL.
Footnotes:
[1]Threshold LRS for significant linkage = 10.7, and for suggestive linkage, 3.3
[2]Threshold LRS for significant linkage = 11.8, and for suggestive linkage, 3.7
*see text for discussion
confirmed in second cross

TABLE 3

Single locus genotypic values for heal1 to heal5.

Genotype

| | D8Mit211 (heal1) | | | D13Mit115 (heal2) | | |
|---|---|---|---|---|---|---|
| | avg | stdev | p* | avg | stdev | p |
| b/b | 0.73 | 0.27 | 0.0319 | 0.96 | 0.25 | 0.0904 |
| b/s | 0.84 | 0.27 | 0.1214 | 0.84 | 0.29 | 0.0567 |
| s/s | 0.95 | 0.28 | 0.0013*** | 0.72 | 0.26 | 0.0024*** |

| | D13Mit129 (heal3) | | | D15Mit244 (heal4) | | |
|---|---|---|---|---|---|---|
| | avg | stdev | p | avg | stdev | p |
| b/b | 0.96 | 0.28 | 0.2156 | 0.95 | 0.19 | 0.0485 |
| b/s | 0.84 | 0.22 | 0.0141** | 0.86 | 0.30 | 0.0677 |
| s/s | 0.74 | 0.34 | 0.0022*** | 0.70 | 0.27 | 0.0013*** |

| | D12Mit132 (heal5) | | |
|---|---|---|---|
| | avg | stdev | p |
| b/s | 0.51 | 0.40 | 0.0005*** |
| s/s | 0.15 | 0.32 | |

Averages and standard deviations for wound diameters at day 30 are given for mice sorted by the genotype of markers near each healing QTL.
*p values in the F2 are listed vertically for b/b vs. b/s, s/s vs. b/s, or b/b vs. s/s; in the backcross.
p values are for die heterozygote b/s vs. the homozygote s/s.
Genotype values are significant at $\alpha = 0.05$ () or $\alpha = 0.01$ (*) in post-hoc analyses.

TABLE 4

Candidate genes in genomic intervals coniaining QTLs

| QTL | MGD cM | Candidate genes in interval |
|---|---|---|
| heal1 | 33 | Comp, cartilage oligomeric matrix protein |
| | 39 | pdw, proportional dwarf |
| | 42 | Os, oligosyndactylism |
| | 46 | Gna0 |
| | 51.5to67 | Cadherin family |
| heal2 | 7 | Nid, nidogen |
| | 8 | Gli3, GLI-Kruppel family member GL13 |
| | 10 | Amph, amphiphysin |
| | 10 | Inhba, inhibin beta-A |
| | 10 | Rasl1, Ras-like, family 1 |
| heal3 | 32 | Msx2, box8 |
| | 32.5 | Fgfr4, fibroblast growth factor receptor |
| | 33 | mes, mesenchymal dysplasia |
| | 36 | Tgfbi, transforming growth factor induced |
| | 44 | Cspg2, chondroitin sulfate proteoglycan |
| | 45 | Rasa, ras p21 GTPase activating protein |
| | 56 | Gpcr 18, G-protein coupled receptor 18 |
| | 62 | Itga 1,2, integrin alpha 2 (Cd49b) |
| heal4 | 51.6 | Pdgfec, platelet derived growth factor |
| | 56.8 | Col2a1, procollagen, type II, alpha 1 |
| | 56.8 | Ela1, elastase 1 |
| | 57 | Emb, embigin |
| | 57.1 | Hoxc, homeo box C cluster |
| | 57.1 | Rarg, retinoic acid receptor, gamma |
| | 57.5 | Dhh, desert hedgehog homolog |
| | 58.7 | Krt2, keratin gene complex 2 |
| | 60 | Itga5, integrin alpha 5 |
| | 61.1 | Itgb7, integrin beta 7 |
| | 63 | Glycam1 adhesion molecule |
| heal5 | 40 | Fos, FBJ osteosarcoma oncogene |
| | 41 | Tgfb3, transforming growth factor, beta |
| | 44.6 | Chx10, C elegans ceh-10 homeo domain con |
| | 45 | Pgf, placental growth factor |

TABLE 5

Differentially expressed or regulated genes identified using microarray analysis of mRNA obtained from healing tissue on days 5 and 20 after ear punch compared to tissue obtained on day 0.

| Gene Group* | Chromosome # | Gene |
|---|---|---|
| IA | 1 | Stat 1 |
| | 1 | PAI-2 |
| | 2 | ABI-2 |
| | 2 | Integrin alpha |
| | 2 | Basic domain transcription factor |
| | 2 | SEF-2 |
| | 4 | TNFR-1 |
| | 4 | SKI |
| | 7 | H-ras |
| | 7 | Cathepsin D |
| | 8 | Glutathione Reductase |
| | 10 | TIMP-3 |
| | 10 | STAT6 |
| | 11 | ACE |
| | 11 | Macrophage inflammatory Protein |
| | 11 | c-erb |
| | 14 | BMP-1 |
| | 14 | Cathepsin B |
| | 16 | HMG |
| | 16 | ETS |
| | 18 | c-FMS |
| IB | 2 | CRAPBII (RA binding protein) |
| | 2 | CD44 |
| | 2 | SKY proto-oncogene |
| | 8 | Casein kinase |
| | 12 | YY1 |
| | 12 | c-AKT |
| | 13 | GTT |
| | 13 | SPI-3 |
| | 13 | GKLF |
| | 13 | Cathepsin L |
| | 13 | PDGF signalling molecule |
| | 13 | thrombin receptor |
| | 15 | epidermal keratin |

*Genes in Group II are listed in Tables 10 and 11. Table 10 is a list of genes which are differentially expressed on days 5 and 20 after ear punch between control mice (B6 & $F_2$ nonhealers) and experimental mice (MRL & $F_2$ healers). Table 11 is a list of genes which are regulated in MRL tissue from 0, 24, and 40 hrs after wounding or ear punching (see FIG. 16).

TABLE 6

Differentially expressed or regulated genes identified using RT-PCR analysis of mRNA from healing tissue.

| Gene Group | Chromosome # | Gene |
|---|---|---|
| IB | 13 | MSX-2 |
|  | 15 | RAR-gamma |

TABLE 7

Differentially expressed genes in Groups I and II identified using differential display analysis of mRNA from healing tissue.*

| Gene Group | Chromosome # | Gene |
|---|---|---|
| IB | 8 | ecadherin |
| II |  | PMG-1 |
|  |  | TR 2-11 |
|  |  | tropomyosin |

*RNA from healer and nonhealer ears on days 0, 5 and 20 after ear punching were analyzed by RT-PCR. Random primers obtained from "Gene Hunter Corp" were used to amplify bands. Since these are random primers, the products are unknown but can be sequenced. It is a useful way of examining what amplifies in one population and not another. Thus, one has to compare what is present or not in B6 and MRL for each time point and then subtract out the differences seen in day 0.

TABLE 8

Differentially expressed genes from Groups I and II identified using SAGE analysis of mRNA from healing tissue.

| Gene Group | Chromosome # | Gene |
|---|---|---|
| IB | 15 | epidermal keratin |
| II |  | macrophage ferritin heavy subunit |
|  |  | est (1758377) and see Table 13. |

TABLE 9

Microsatellite Markers Linked to Male and Female Healer Mice

| CHROM # | MARKER | LOCATION (CM) | LRS | CROSS |
|---|---|---|---|---|
| 1 | D1MIT64 | 21 | 5.1 | F2-Male |
| 1 | D1MIT123 | 36.9 | 4 | F2-Male |
| 1 | D1MIT288 | 71.5 | 7.5 | F2 |
| 1 | D1MIT356 | 95.8 | 4.3 | F2-Female |
| 2 | D2MIT329 | 45 | 5.6 | F2-Female |
| 2 | D2MIT37 | 45 | 6.3 | F2-Female |
| 2 | D2MIT14 | 49 | 8 | F2-Female |
| ##2 | D2MIT207 | 60 | 10.5 | F2-Male; F2 |
| 2 | D2MIT107 | 75.6 | 7.9 | F2-Male |
| 2 | D2MIT223 | 76.7 | 9.3 | F2-Male |
| 2 | D2MIT148 | 105 | 4.8 | Backcross |
| 3 | D3MIT60 | 0 | 6.3 | F2 |
| 3 | D3MIT203 | 11.2 | 4.3 | F2 |
| 3 | D3MIT310 | 38.3 | 5.4 | F2; F2-Male |
| ##4 | D4MIT149 | 0 | 13.4 | F2-Male |
| 4 | D4MIT235 | 2 | 9.8 | F2-Male |
| 4 | D4MIT236 | 12 | 5 | F2-Male |
| 4 | D4MIT241 | 25 | 5.5 | F2-Male |
| 4 | D4MIT127 | 78 | 8.8 | F2-Male |
| 5 | D5MIT148 | 18 | 5.8 | F2-Female |
| 6 | NONE |  |  |  |
| ##7 | D7MIT220 | 52 | 10.2 | Backcross |
| 7 | D7MIT237 | 66 | 6.6 | Backcross |
| 8 | D8MIT191 | 21 | 6.4 | Backcross |
| #8 | D8MIT211 | 49 | 9.9 | B6 |
| 9 | NONE |  |  |  |
| 10 | D10MIT42 | 44 | 3.5 | F2-Female |
| 10 | D10MIT233 | 62 | 4.2 | F2-Male |
| 11 | D11MIT124 | 61 | 8.1 | F2-Male; F2 |
| 12 | D12MIT4 | 34 | 7.1 | Backcross |
| 12 | D12MIT233 | 52 | 9.4 | Backcross |
| ##12 | D12MIT132 | 52 | 10.9 | Backcross |
| 13 | D13MIT135 | 10 | 9.4 | F2 |
| 13 | D13MIT115 | 11 | 9.7 | F2 |
| 13 | D13MIT116 | 13 | 9 | F2 |
| 13 | D13MIT245 | 30 | 8.8 | F2 |
| ##13 | D13NDS1 | 32 | 15.9 | F2 |
| 13 | D13MIT126 | 45 | 6.6 | F2 |
| 13 | D13MIT191 | 45 | 9.4 | F2 |
| ##13 | D13MIT159 | 45 | 12.7 | F2 |
| 13 | D13MIT29 | 47 | 6.5 | F2 |
| 13 | D13MIT107 | 48 | 7 | F2 |
| 13 | D13MIT144 | 48 | 6 | F2 |
| ##13 | D13MIT148 | 59 | 11.9 | F2 |
| ##13 | D13MIT129 | 60 | 11.2 | F2 |
| 13 | D13MIT53 | 62 | 9.1 | F2 |
| 13 | D13MIT151 | 71 | 8.2 | F2 |
| 14 | D14MIT193 | 40 | 5 | F2-Male |
| 14 | D14MIT131 | 58 | 4 | F2-Male |
| 15 | D15MIT189 | 48.5 | 6.6 | F2; F2-Female |
| 15 | D15MIT171 | 54.5 | 6.7 | " |
| 15 | D15MIT242 | 55.6 | 6.7 | " |
| 15 | D15MIT172 | 57.8 | 6.9 | " |
| ##15 | D15MIT242 | 55.6 | 10.7 | " |
| 15 | D15MIT14 | 56.8 | 9.3 | " |
| 15 | D15MIT43 | 60.4 | 4.6 | " |
| 15 | D15MIT79 | 66.2 | 7.9 | " |
| 15 | D15MIT16 | 61.7 | 5.9 | " |
| 16 | D16MIT122 | 3.85 | 6.2 | F2 |
| 16 | D18MIT32 | 48.2 | 6.6 | F2 |
| 17 | D17MIT68 | 24.5 | 5.7 | F2 |
| 18 | D18MIT123 | 31 | 4.8 | F2 |
| 18 | D1BMIT49 | 49 | 4.1 | F2 |
| 19 | D19MIT59 | 0.5 | 7.2 | F2-Female |

The suggestive loci have an LRS value of 3.5 or greater

The significant loci have an LRS value of 10.5 or greater (except when confirmed in a second cross (##))

TABLE 10

Wound Healing Gene Products Identified by Microarray Analysis

Chrom.

| Day 5 Express. | Day 20 Exp. | Locat. (cM) | Gene Products identified by microarray analysis (day 5 and 20 healer and nonhealer ear holes compared to day 0) |
|---|---|---|---|
| up | up | ? | Ezrin; Villin 2; NF-2 (merlin) related filament/plasma membrane associated protein |
| no change | DOWN | 14 (41) | Rb; pp105; Retinoblastoma suseptibility-associated protein (tumor suppressor gene; cell cycle regulator) |
| up (female) | | 7 (syntenic) | TSG101 tumor suseptibility protein |
| down (female) | down (female) | ? | Tumor suppressor maspin |
| down (male) | down (male) | 7 (28.5) | ZO-1; Tight junction protein; discs-large family member, partially homologous to a dig-A tumor suppressor in Drosophila |
| down (male) | down (male) | 11 (57) | c-ErbA oncogene; thyroid hormone receptor |
| up | up | 4 (44.6) | c-Jun proto-oncogene (transcription factor AP-1 component) |
| no change | down | ? | RNA polymercase I termination factor TTF-1 |
| up | up | 15 (32) | c-myc proto-oncogene protein |
| down (female) | up (female) | 8 (49.5) | Casein kinase II (alpha subunit) |
| down (male) | down (male) | 17 (16.4) | Plm-1 proto-oncogene |
| up (female) | | 18 (30) | c-Fms proto-oncogene (macrophage colony stimulating factor 1 (CSF-1) receptor) |
| up (female) | up (female) | 5 (42) | PDGFRa; platelet-derived growth factor alpha-receptor |
| down (male) | down (male) | 4 (78.9) | Sid proto-oncogene |
| up | | 2 (67) | Sky proto-oncogene (Tyro3; Rse; Dtk) |
| up (female) | | 7 (72.2) | H-ras proto-oncogene: transforming G-protein |
| | down (male) | 3 (48.5) | N-ras proto-oncogene; transforming G-protein |
| | up (male) | 1 (36.1) | IGFBP-2; insulin-like growth factor binding protein 2; autocrine and/or paracrine |
| up (female) | | ? | Cyclin B2 (G2/M-specific) |
| down | up | ? | Cyclin D2 (G1/S-specific) |
| up (male) | down (male) | ? | Cyclin G (G2/M-specific) |
| up | down | ? | p18lnk4; cdk4 and cdk6 inhibitor |
| down | up | ? | Prothymosin alpha |
| up | | ? | HSP84; heat shock 84kD protein |
| up | | ? | HSP86; heat shock 86kD protein |
| up | | 2 (22.5) | Glucose regulated protein, 78kD; Grp78 |
| up (male) | | 3 (66.2) | Golgi 4-transmembrane spanning transporter; MTP |
| up | | 13 (47) | Cf2r; coagulation factor II (thrombin) receptor |
| up (female) | | ? | Interleukin-6 receptor beta chain; membrane glycoprotein gp130 |
| up | | 19 (0.5) | I-kappa B alpha chain |
| up (male) | down (male) | 1 (28) | Stat1; signal transducer and activator of transcription |
| up (male) | down (male) | 10 (70) | Stat6; signal transducer and activator of transcription 6: IL-4 Stat; STA6 |
| up | | 11 (syntenic) | Crk adaptor protein |
| up | down | 17 (40) | Inhibitor of the RNA-activated protein kinase, 58-kDa |
| up | | ? | MAPK; MAP kinase; p38 |
| UP | DOWN | 9 (36) | MAPKK1; MAP kinase kinase 3 (dual specificity) (MKK1) |
| up | down | 2 (2) | PKC-theta |
| down | down | 13 (50) | PI-K p58, PDGF signaling pathway member |
| up (male) | down (male) | ? | Rab2 ras-related protein |
| up (male) | down (male) | ? | 14-3-3 protein eta |
| up | | 11 (29) | IRF1: Interferon regulatory factor 1 |
| UP | DOWN | ? | Zyxin; LIM domain protein; alpha-actinin binding protein |
| up (male) | down (male) | ? | BAG-1: bcl-2 binding protein with anti-cell death activity |
| up | up | 13 (8) | Glutathione peroxidase (plasma protein); selenoprotein |
| up | | 8 (16) | Glutathione reductase |
| DOWN | DOWN | ? | Glutathione S-transferase (microsomal) |
| down (male) | | ? | Glutathione S-transferase Mu 1 |
| up | down | 12 (58) | c-Akt proto-oncogene, Rac-alpha: proteine kinase B (PKB) |
| up | down | ? | FLIP-L; apoptosis inhibitor: FLICE-like inhibitory protein |
| up (female) | down (female) | 3 (70.5) | Gadd45; growth arrest and DNA-damage-inducible protein |
| up | | ? | Nm23-M2: nucleoside diphosphate kinase B; metastasis-reducing protein; c-myc-related transcription factor |
| up (male) | down (male) | ? | Protein tyrosine phosphatase |
| up (male) | down (female) | 19 (23) | RIP cell death protein; Fas/APO-1 (CD95) interactor, contains death domain |
| UP | DOWN | 13 (16) | SP13; serpin; similar to human proteinase inhibitor 6 (placental thrombin inhibitor) serine proteinase inhibitor |
| UP | DOWN | 4 (75.5) | Tumor necrosis factor receptor 1; TNFR-1 |
| up (female) | UP (female) | ? | PA6 stromal protein; RAG1 gene activator |
| up | | ? | MHR238; Rad23 UV excision repair protein homologue; xeroderma pigmentosum group C (XPC) repair complementing protein |
| up | | 2 (45) | Abiphilin-1 (abi-1) similar to HOXD3 |
| | UP | x-14 | Adipocyte differentiation-associated protein |
| H>>NH | H>>NH | 2 (91) | Basic domain/leucine zipper transcription factor |
| up | | ? | Butyrate response factor 1 |
| NH>>H | NH>>H | ? | CACCC Box- binding protein BKLF |
| up | | ? | DP-1 (DRTF-polipeptide 1) cell cycle regulatory transcription factor |
| down (female) | up (female) | 16 (68.5) | Ets-2 transcription factor |
| down (female) | up (female) | 2 (7) | GATA-3 transcription factor |
| down (female) | up (female) | 13 (16) | Gut-specific Kruppel-like factor GKLF |
| down (female) | up (female) | 16 (69) | HMG-14 non histone chromosomal protein |
| up NH>H | | ? | Interferon regulatory factor 2 (IRF 2) |
| up NH>H | | ? | NF-1B protein (transcription factor) |
| up | down | 15 (61.7) | Nuclear factor related to P45 NF-E2 |
| up (male) | down (male) | 9 (36) | Nuclear hormone receptor ROR-ALPHA-1 |
| up | down | 6 (syntenic) | Split hand/foot gene |
| down (female) | up (female) | 2 (54) | Retinoic acid binding protein II cellular (CRABP-II) |

| | | | |
|---|---|---|---|
| down (female) | up (female) | ? | Retinoid X receptor interacting protein (RIP 15) |
| up | down | ? | Transcription factor 1 for heat shock gene |
| up | | 7 | Transcription factor CTCF (11 zinc fingers) |
| NH>>H | up (female) | 2 (94) | Transcription factor SEF2 |
| down (female) | up (female) | ? | YB1 DNA binding protein |
| up (female) | up (female) | 12 (53) | YY1 (UCRBP) transcriptional factor |
| NH>>H down (f) | up (female) | ? | Activin type I receptor |
| up (male) | down (male) | ? | C-C chemokine receptor (Monocyte chemoattractant protein 1 receptor (MCP-1RA) |
| down (female) | down (female) | ? | Growth factor receptor |
| NH>>>H up | up | 18 (20) | Glucocorticoid receptor form A |
| up | | 6 (31.5) | CD31 (Platelet endothelial cell adhesion molecule 1) |
| up | up | 2 (56) | CD44 antigen |
| up | | 9 (56) | Dystroglycan 1 |
| up | down | ? | Glutamate receptor channel subunit gamma |
| up | | 2 (38) | Integrin alpha 6 |
| UP (female) | up (female) | ? | Integrin beta |
| UP (female) | up (female) | ? | Laminin receptor 1 |
| up (male) | UP (female) | 14 (32.5) | Bone morphogenetic protein 1 |
| NH>>H up | | ? | Insulin-like growth factor binding protein-6 (IGFBP 6) |
| | up | 11 (2) | Insulin-like growth factor binding protein-3 (IGFBP-3) |
| | UP | ? | Insulin-like growth factor binding protein-4 (IGFBP-4) |
| | UP | 1 (36) | Insulin-like growth factor binding protein-5 (IGFBP-5) |
| UP (female) | UP (female) | 10 (48) | Insulin-like growth factor-1A |
| up | | 11 (47.8) | Macrophage inflammatory protein |
| | down (male) | 18 (48) | Mad related protein 2 (MADR2) |
| up | | 7 (11) | Neuroleukin |
| | UP (female) | 14 (20) | Placental ribonuclease inhibitor (Angiogenin) |
| up | down | 7 (6.5) | Transforming growth factor beta |
| up | down | 7 (6.5) | Transforming growth factor beta 2 |
| up (female) | | x (1.7) | Cytoskeletal epidermal keratin (14 human) |
| H>>>NH UP | UP | 15 (58.7) | Epidermal keratin (1 human) |
| up (male) | down (male) | 9 (81) | Non-muscle myosin light chain 3 |
| up (female) | | 2 (7) | Vimentin |
| up | down | 11 (65) | Angiotensin-converting enzyme (ACE) (clone ACE 5.) |
| | up | 14 (28.5) | Cathepsin B |
| | down | 7 (72.5) | Cathepsin D |
| | up | 13 (30) | Cathepsin L |
| H>>NH up (f) | down (male) | ? | Cytotoxic T lymphocyte-specific serine protease CCP I gene (CTLA-1) |
| NH>>H | UP | 14 (20) | Mast cell protease (MMCP)-4 |
| | UP (female) | ? | Membrane type matrix metalloproteinase |
| | DOWN | 1 (61) | Plasminogen activator inhibitor-2 |
| | UP | ? | Serine protease inhibitor homolog J6 |
| NH>>>H up | | 10 (47) | TIMP-3 tissue inhibitor of metalloproteinases-3 |

TABLE 11

Genes whose expression is altered in MRL mice 0 hrs., 24 hrs., and 40 hrs. after ear punch.

| Block A | Block B | Block C | Block D | Block E | Block F |
|---|---|---|---|---|---|
| 1a. APC | 1a. HSP-27 | 1a. Caspase-11 | 1a. abi-1 | 1c. BMP-R | 1b. BMP-1 |
| 1b. BRCA1 | 1b. HSP-60 | 1e. bag-1 | 1j. BKLF | 1g. CSA-R | 1d. BMP-4 |
| 1e. EB1 | 1c. HSP-84 | 1f. Bak | 1k. C/EBP | 2b. FGFR-4 | 1g. Cek 5 |
| 1f. ezrin | 1d. HSP-86 | 1g. Bax | 2g. DP-1 | 2e. GMCSF-R | 1h. Cek 7 |
| 1i. NF2 | 1f. Osp-94 | 2a. GTT trnfs. | 2j. Elf-1 | 2l. INFab-R | 1j. EGF |
| 1j. p107 | 1j. cyp1b1 | 2b. GTT Mu-1 | 3m. HMG-14 | 2m. INFg-R | 2a. G-CSF |
| 1l. p53 | 2e. Glut1 | 2d. GST pi-1 | 3n. Hox1.1 | 3a. IL-1R | 2i. IGFBP-6 |
| 2a. maspin | 3d. CXCR4 | 2e. A20 znc fnger pr. | 4g. Hox 8 | 3c. IL2-R | 2k. IGFBP-3 |
| 2d. VHL | 3f. Prostaglandin E R | 2k. c-Akt | 4m. LKLF | 3d. IL3R | 2l. IGFBP-4 |
| 2g. c-erb | 3g. Tie-1 | 3a. CHOP 10 | 4n. Lbx1 | 3g. IL-7R | 2m. IGFBP-5 |
| 2j. TTF-1 | 3j. Vegfr-2 | 3b. Clusterin | 5a. Mph-1 | 3h. IL8-R | 3a. ILGF-14 |
| 2l. c-myc | 4h. TANK | 3f. Fas1 R | 5b. MRE | 3i. Estrog R | 3c. K-FGF |
| 3b. FLI-1 | 4k. Tristetraproline | 4c. Nm23-M2 | 5h. NF-E2 | 3j. Androg R | 3g. MIP2 |
| 3e. Gli | 5b. Hck | 4g. PtPhosphatase | 5m. DSS-1 | 3m. Glucocort R | 3h. MADR2 |
| 3l. B-Raf | 5f. CamK | 4h. PS-2 | 5n. Sox3 | 4a. Insulin R | 3j. Smad 1 |
| 4e. PDGFRa | 5h. Erk1 | 5a. TDAG51(fas reltd) | 6b. PAX-6 | 4b. IRS-1 | 3k. NGF |
| 4g. SKI | 5j. Jak3 | 5b. TNF 55 | 6f. RXR-6 | 4h. Serotonin R 1e-b | 3m. neuroleukin |
| 4j. Vegfr-1 | 6h. PKC-theta | 5d. TNFR-1 | 6g. RIP-15 | 4j. Serotonln R 3 | 3n. oncostatin |
| 4n. C-Src | 6k. PI3-K | 6j. MHR23B | 6i. TF-1 for HSP | 4m. Adrenergic R beta 1 | 4d. thrombomod. |
| 5c. H-ras | 7b. Rab-2 | 7b. PCNA | 7e. SEF2 | 5c. GPCR | 4g. TGFb2 |
| 5d. LFC | 7j. GapIII | 7c. bluelight R | 7g. SP2 | 5f. GABA-A 3 | 5b. IL-4 |
| 5j. b-protachykinin | 7n. Zyxin | 7e. Pur | | 5g. GABA-A 4 | 5c. IL-6 |
| 5m. IGFBP-2 | | 7k. HR6B | | 5l. P-selectin | 5d. IL-7 |
| 6a. cyclin A | | 7n. XRCC1 | | 5m. catenin alpha | 5e. cardiac myosin |
| 6d. cyclin B2 | | | | 6a. CD2 | 5g. CDC42 bind. prot. |
| 6h. cyclin D3 | | | | 6h. CD14 | 5h. epidermal keratin-14 |
| 7b. p58/GTA | | | | 6m. dystroglycan | 5i. epid.k-18 |
| 7e. cdk inhibit prot. | | | | 6n. glutamale R | 5k. epiderm keratin |
| 7j. cdc25a | | | | 7a. CD49b | 5n. kinesin |

TABLE 12

SAGE Analysis of C57BL/6 Mice Five Days After Wounding

```
SearchName = B5BANK
FileName = c:\sage\data\b5data~1\b5bank.bag
Anchoring Enzyme = NIaIII - CATG
TagLength = 11
DiTag Length = 24
Total Files = 56
Total Tags = 1508
Total Duplicate Dimers = 0
Tag Abundance Report
Total tags after excluding tags = 1508
```

| Count | Percent | Tag Sequence | Tag Base Four Number |
|---|---|---|---|
| 16 | 1.061 | GGCTTCGGTCT | 2750136 |
| 13 | .862 | AGAGCGAAGTG | 563247 |
| 12 | .7957 | AGCAGTCCCCT | 601432 |
| 12 | .7957 | GTGGCTCACAA | 3054865 |
| 10 | .6631 | AGGCAGACAGT | 673868 |
| 9 | .5968 | GCTGGCCCTTC | 2598270 |
| 8 | .5305 | AGGTCGGGTGG | 711355 |
| 8 | .5305 | CGCCGCCGGCT | 1664424 |
| 7 | .4641 | CTGCTCAGGCT | 1995944 |
| 7 | .4641 | TGGGCATCCAC | 3838802 |
| 6 | .3978 | AAGGAAATGGG | 164075 |
| 6 | .3978 | ATACTGACATT | 817232 |
| 6 | .3978 | CCTTTGTGACT | 1571720 |
| 6 | .3978 | GAACATTGCAC | 2117522 |
| 6 | .3978 | GGGAAGGCGGC | 2755178 |
| 5 | .3315 | ATGACTGATAG | 925235 |
| 5 | .3315 | CACAAACGGTA | 1114541 |
| 5 | .3315 | CACCACCGTTG | 1131967 |
| 5 | .3315 | CAGAACCCACG | 1180999 |
| 5 | .3315 | CCCTGAGTCCA | 1434325 |
| 5 | .3315 | CCCTGGGTTCT | 1436408 |
| 5 | .3315 | GCCCGGGAATA | 2451981 |
| 5 | .3315 | GCGGCGGATGG | 2529851 |
| 5 | .3315 | GGAAGCCACTT | 2630944 |
| 5 | .3315 | TAAAGAGGCCG | 3154583 |
| 5 | .3315 | TATGTCAAGCT | 3388456 |
| 5 | .3315 | TGGGTTGTCTA | 3849949 |
| 5 | .3315 | TGTAGTGTAAT | 3878596 |
| 5 | .3315 | TTCAGTGGACC | 4009606 |
| 5 | .3315 | TTGGTGAAGGA | 4110377 |
| 4 | .2652 | AGAAACCAATA | 525581 |
| 4 | .2652 | AGTGAGGAAGA | 756233 |
| 4 | .2652 | ATAATACATAA | 799025 |
| 4 | .2652 | ATACTGAAGCC | 817190 |
| 4 | .2652 | ATTCTCCAGTG | 1013039 |
| 4 | .2652 | CAAACTCTCAC | 1056210 |
| 4 | .2652 | CAGTCACCAAC | 1233218 |
| 4 | .2652 | CCCACAAGGTA | 1380525 |
| 4 | .2652 | CCTTGCTCAAT | 1566532 |
| 4 | .2652 | CCTTTGAGATC | 1570958 |
| 4 | .2652 | CTAGTCTTTGT | 1882108 |
| 4 | .2652 | CTGAACATCTC | 1967326 |
| 4 | .2652 | GGCAAGCCCCA | 2689365 |
| 4 | .2652 | GGCCTGGCTTA | 2718333 |
| 4 | .2652 | TCCCCGTACAT | 3496724 |
| 4 | .2652 | TCCCTATTAAG | 3503043 |
| 4 | .2652 | TCTTCTCACAA | 3661073 |
| 4 | .2652 | TGGCCCAAATT | 3822608 |
| 3 | .1989 | AAGGTGGAAGA | 178697 |
| 3 | .1989 | ACATCATAGAT | 316196 |
| 3 | .1989 | AGGAAGGCGGC | 658026 |
| 3 | .1989 | CAAGTGGAAAA | 1096193 |
| 3 | .1989 | CACGCTCCCGG | 1154395 |
| 3 | .1989 | CAGGCCACACA | 1217605 |
| 3 | .1989 | CCAGAACAGAC | 1343778 |
| 3 | .1989 | CCCAGAGCACT | 1385032 |
| 3 | .1989 | CCCTAAACTGA | 1425529 |
| 3 | .1989 | CCTGATCTTTA | 1543677 |
| 3 | .1989 | CCTTTAATCCC | 1568982 |
| 3 | .1989 | CTCAACAGCAA | 1901713 |
| 3 | .1989 | CTCCTGGACAC | 1931794 |
| 3 | .1989 | CTGGCTTTCAG | 2006995 |
| 3 | .1989 | GACTTTGGAAA | 2227841 |
| 3 | .1989 | GAGCGTTTTGG | 2256891 |
| 3 | .1989 | GATGACACCAG | 2327635 |

TABLE 12-continued
SAGE Analysis of C57BL/6 Mice Five Days After Wounding

```
SearchName = B5BANK
FileName = c:\sage\data\b5data~1\b5bank.bag
Anchoring Enzyme = NIaIII - CATG
TagLength = 11
DiTag Length = 24
Total Files = 56
Total Tags = 1508
Total Duplicate Dimers = 0
Tag Abundance Report
Total tags after excluding tags = 1508
```

| Count | Percent | Tag Sequence | Tag Base Four Number |
|---|---|---|---|
| 3 | .1989 | GCTGCAGTTGA | 2593529 |
| 3 | .1989 | GCTGCCCTCCA | 2594261 |
| 3 | .1989 | GTCTGCTGATG | 3008399 |
| 3 | .1989 | GTGGAGGCGCC | 3050086 |
| 3 | .1989 | GTGGGCGTGTA | 3057389 |
| 3 | .1989 | TAAACCTGCTA | 3151773 |
| 3 | .1989 | TATCCCACGCC | 3363942 |
| 3 | .1989 | TCGGTTTCTGC | 3587962 |
| 3 | .1989 | TCTCACCACCC | 3622166 |
| 3 | .1989 | TGACCCCGGGA | 3691945 |
| 3 | .1989 | TGCACAGTGCT | 3740392 |
| 3 | .1989 | TGGTCTGGTCC | 3858102 |
| 3 | .1989 | TGTAACAGGAC | 3867810 |
| 3 | .1989 | TTCAGGTGGTT | 4008880 |
| 3 | .1989 | TTGGCTGCCCA | 4103765 |
| 2 | .1326 | AAAACAGTGGC | 4842 |
| 2 | .1326 | AAAGCAGTGCT | 37608 |
| 2 | .1326 | AAGAGGCAAGA | 141577 |
| 2 | .1326 | AAGCAACAGGT | 147756 |
| 2 | .1326 | AAGGTCGAGCT | 177704 |
| 2 | .1326 | ACAGAACTCTT | 295392 |
| 2 | .1326 | ACCTTGGAAGG | 391691 |
| 2 | .1326 | ACTCTTTGTTT | 491456 |
| 2 | .1326 | ACTGGCTGGGC | 501674 |
| 2 | .1326 | ACTTATTATGC | 511802 |
| 2 | .1326 | AGAACCATTAA | 529649 |
| 2 | .1326 | AGACCCTCTCA | 546677 |
| 2 | .1326 | AGCAATTCAAA | 593729 |
| 2 | .1326 | ATCAACACCGC | 853082 |
| 2 | .1326 | ATCCGAAAGAT | 876580 |
| 2 | .1326 | CACCACCACAG | 1131795 |
| 2 | .1326 | CACCTTGGTGC | 1146554 |
| 2 | .1326 | CACGGGACCAC | 1157202 |
| 2 | .1326 | CACTGACCTCC | 1171830 |
| 2 | .1326 | CATTATGGGTG | 1298095 |
| 2 | .1326 | CCCAATGGCCC | 1379990 |
| 2 | .1326 | CCCGGACTTAC | 1417714 |
| 2 | .1326 | CCCGTAGCCCC | 1421910 |
| 2 | .1326 | CCTACAGTTGA | 1512185 |
| 2 | .1326 | CCTCGGAAAAT | 1533956 |
| 2 | .1326 | CCTGTGTGAAA | 1555329 |
| 2 | .1326 | CGCCTGCTAGC | 1669578 |
| 2 | .1326 | CGCTGGTTCCA | 1698773 |
| 2 | .1326 | CGGTTCCACCC | 1766678 |
| 2 | .1326 | CTAATAAAGCC | 1847334 |
| 2 | .1326 | CTACCAGGATA | 1856141 |
| 2 | .1326 | CTGCTATCCGA | 1995609 |
| 2 | .1326 | CTGCTTTGTGC | 1998778 |
| 2 | .1326 | CTGGGCGTGTC | 2008814 |
| 2 | .1326 | CTGTAGGTGAT | 2018020 |
| 2 | .1326 | CTGTGCCCTCC | 2024822 |
| 2 | .1326 | CTTAAGGATCC | 2034230 |
| 2 | .1326 | GAATCTGAAGT | 2153996 |
| 2 | .1326 | GAATGCAGGGA | 2155689 |
| 2 | .1326 | GAGGAGAAGAA | 2263073 |
| 2 | .1326 | GATGCATAGTG | 2331439 |
| 2 | .1326 | GATGTGACCAC | 2340946 |
| 2 | .1326 | GATTTCTGTCT | 2357176 |
| 2 | .1326 | GCACCGAACAC | 2381842 |
| 2 | .1326 | GCATACGGCGC | 2410138 |
| 2 | .1326 | GCATTGCATCT | 2423096 |
| 2 | .1326 | GCCAAGGGTCA | 2427573 |
| 2 | .1326 | GCCAAGTGGAG | 2427811 |
| 2 | .1326 | GCCTAATGTAC | 2474930 |
| 2 | .1326 | GCCTCGGGGGA | 2480809 |

TABLE 12-continued

SAGE Analysis of C57BL/6 Mice Five Days After Wounding

```
SearchName = B5BANK
FileName = c:\sage\data\b5data~1\b5bank.bag
Anchoring Enzyme = NlaIII - CATG
TagLength = 11
DiTag Length = 24
Total Files = 56
Total Tags = 1508
Total Duplicate Dimers = 0
Tag Abundance Report
Total tags after excluding tags = 1508
```

| Count | Percent | Tag Sequence | Tag Base Four Number |
|---|---|---|---|
| 2 | .1326 | GCGACGCGGGC | 2496938 |
| 2 | .1326 | GCGGCGGGATG | 2529935 |
| 2 | .1326 | GCTCAGGATTC | 2574910 |
| 2 | .1326 | GCTGGCAGACG | 2598023 |
| 2 | .1326 | GCTTGCTTCCT | 2615256 |
| 2 | .1326 | GGAAGGTGTCT | 2632632 |
| 2 | .1326 | GGATTTGGCTT | 2686624 |
| 2 | .1326 | GGGAGCTGTGC | 2762682 |
| 2 | .1326 | GGGGAAATCGC | 2785498 |
| 2 | .1326 | GGGGCTCAGCC | 2792742 |
| 2 | .1326 | GGTGAGCCTGA | 2853241 |
| 2 | .1326 | GGTGGGACACA | 2861125 |
| 2 | .1326 | GTAAGCATAAA | 2892993 |
| 2 | .1326 | GTCTGGGGGA | 3009193 |
| 2 | .1326 | GTGGTAGGCTA | 3060381 |
| 2 | .1326 | GTTGCTGAGAA | 3120673 |
| 2 | .1326 | GTTGGGGGGGG | 3123883 |
| 2 | .1326 | TAACTGACAAT | 3176516 |
| 2 | .1326 | TATACAATACA | 3346629 |
| 2 | .1326 | TCCACTGTGCA | 3481317 |
| 2 | .1326 | TCTGGACGCGG | 3645851 |
| 2 | .1326 | TGAAACACTGT | 3671164 |
| 2 | .1326 | TGACCCCGGGT | 3691948 |
| 2 | .1326 | TGCCTGTGATA | 3767181 |
| 2 | .1326 | TGGATCCTGAG | 3814883 |
| 2 | .1326 | TGGGCAAAGCC | 3837990 |
| 2 | .1326 | TGGTGACAAAA | 3858689 |
| 2 | .1326 | TGTGCCAAGTG | 3904559 |
| 2 | .1326 | TGTTCATCTTG | 3920767 |
| 2 | .1326 | TTCAGCTCGAG | 4007779 |
| 2 | .1326 | TTGCTGCAGTG | 4094255 |

```
Tags included in this report = 161
DataBase Link
Database = c:
        16         1.061%  GGCTTCGGTCT              2750136
  Noted Tags = 0          Collected Tags = 0
        13          .862%  AGAGCGAAGTG               563247
  Noted Tags = 1          Collected Tags = 1
GCGGAA, Class A, U93862, Mus musculus ribosomal protein L41 mRNA,
complete
        12          .7957% AGCAGTCCCCT               601432
  Noted Tags = 4          Collected Tags = 0
        12          .7957% GTGGCTCACAA              3054865
  Noted Tags = 207        Collected Tags = 56
CCATCC, Class A, AB0045, Mus musculus mRNA for Rab33B,
complete cds.
CCATCT, Class C, L29190, Mouse MHC class I H2-D
transplantation antigen gen
CCATCT, Class A, U20225, Mus musculus adenylosuccinate
lyase (adl) mRNA, co
CCATCT, Class A, X93168, M.musculus mRNA for cannabinoid
receptor 2.
CCATCT, Class A, X56974, M.musculus mRNA for external
transcribed spacer (p
CCATCT, Class C, X52915, M.musculus gene for H-2D(q) antigen,
partial 3'c
CCATCT, Class C, V00751, Mouse gene H-2Ld coding for
a transplantation anti
CCATCT, Class C, X52916, M.musculus H-2L(q) gene for
H-2L(q) antigen. 3'p
CCATCT, Class C, U06244, Mus musculus interferon
alpha/beta receptor (IFNAR
CCATCC, Class C, X64716, M.musculus NKR-P1 2 gene for
natural killer cell r
        10          .6631% AGGCAGACAGT               673868
```

TABLE 12-continued

SAGE Analysis of C57BL/6 Mice Five Days After Wounding

```
SearchName = B5BANK
FileName = c:\sage\data\b5data~1\b5bank.bag
Anchoring Enzyme = NIaIII - CATG
TagLength = 11
DiTag Length = 24
Total Files = 56
Total Tags = 1508
Total Duplicate Dimers = 0
Tag Abundance Report
Total tags after excluding tags = 1508
     Count       Percent  Tag Sequence        Tag Base Four Number Noted Tags = 2          Collected Tags = 2
TGCTGT, Class A, X13661, Mouse mRNA for elongation
factor 1-alpha (EF 1-alp
TGCTGT, Class A, M22432, Mus musculus protein synthesis
elongation factor T
     9           .5968%   GCTGGCCCTTC                2598270
  Noted Tags = 0          Collected Tags = 0
     8           .5305%   AGGTCGGGTGG                 711355
  Noted Tags = 1          Collected Tags = 0
     8           .5305%   CGCCGCCGGCT                 164424
  Noted Tags = 1          Collected Tags = 0
     7           .4641%   CTGCTCAGGCT                1995944
  Noted Tags = 1          Collected Tags = 1
TAGGAG, Class A, M13806, Mouse keratin (epidermal)
type I mRNA, clone pkScc
     7           .4641%   TGGGCATCCAC                3838802
  Noted Tags = 0          Collected Tags = 0
     6           .3978%   AAGGAAATGGG                 164075
  Noted Tags = 0          Collected Tags = 0
     6           .3978%   ATACTGACATT                 817232
  Noted Tags = 4          Collected Tags = 0
     6           .3978%   CCTTTGTGACT                1571720
  Noted Tags = 0          Collected Tags = 0
     6           .3978%   GAACATTGCAC                2117522
  Noted Tags = 3          Collected Tags = 2
CACACG, Class A, X12697, Mouse p2-4 mRNA for
SPARC/osteonectin (SPARC = sec
CACACG, Class C, M20691, Mouse osteonectin
(Sparc) gene, exon 9.
     6           .3978%   GGGAAGGCGGC                2755178
  Noted Tags = 2          Collected Tags = 1
ACGTCT, Class A, M88335, M.musculus mRNA sequence.
     5           .3315%   ATGACTGATAG                 925235
  Noted Tags = 4          Collected Tags = 0
     5           .3315%   CACAAACGGTA                1114541
  Noted Tags = 0          Collected Tags = 0
     5           .3315%   CACCACCGTTG                1131967
  Noted Tags = 1          Collected Tags = 1
CCTTCA, Class C, M21460, Mouse surfeit locus
surfeit 3 protein gene, exon 6
     5           .3315%   CAGAACCCACG                1180999
  Noted Tags = 2          Collected Tags = 2
ACAGTA, Class C, M76762, Mus musculus ribosomal
protein (Ke-3) gene, exons
ACAGTA, Class A, M76763, Mus musculus ribosomal
protein (Ke-3) mRNA, comple
     5           .3315 %  CCCTGAGTCC                 1434325
  Noted Tags = 2          Collected Tags = 2
CCCCGG, Class A, X03672, Mouse cytoskeletal mRNA
for beta-actin.
CCCCGG, Class A, J04181, Mouse A-X actin mRNA, complete cds.
     5           .3315%   CCCTGGGTTCT                1436408
  Noted Tags = 2          Collected Tags = 1
GCCCGC, Class A, J04716, Mouse ferritin light chain,
complete cds.
     5           .3315%   GCCCGGGAATA                2451981
  Noted Tags = 1          Collected Tags = 1
AATTCA, Class A, J05277, Mouse hexokinase mRNA, complete cds.
     5           .3315%   GCGGCGGATGG                2529851
  Noted Tags = 6          Collected Tags = 5
AGACTT, Class C, A27894, Coding sequence for GBP.
AGACTT, Class A, X53067, Mouse mRNA for 14KDa lectin.
AGACTT, Class A, X15986, Mouse 3' mRNA for
beta-galactoside specific lectin
AGACTT, Class A, X66532, M.musculus mRNA for L14 lectin.
```

TABLE 12-continued

SAGE Analysis of C57BL/6 Mice Five Days After Wounding

```
SearchName = B5BANK
FileName = c:\sage\data\b5data~1\b5bank.bag
Anchoring Enzyme = NIaIII - CATG
TagLength = 11
DiTag Length = 24
Total Files = 56
Total Tags = 1508
Total Duplicate Dimers = 0
Tag Abundance Report
Total tags after excluding tags = 1508
       Count      Percent Tag Sequence         Tag Base Four Number
```

AGACTT, Class A, M57470, Murine beta-galactoside binding
protein mRNA, comp
         5          .3315%GGAAGCCACTT             2630944
  Noted Tags = 0          Collected Tags = 0
         5          .3315%TAAAGAGGCCG             3154583
  Noted Tags = 1          Collected Tags = 1
TTTTGT, Class A, U67770, Mus musculus ribosomal
protein S26 (RPS26) mRNA, c
         5          .3315%TATGTCAAGCT             3388456
  Noted Tags = 1          Collected Tags = 1
GGTGGA, class A, X15962, Mouse mRNA for ribosomal protein S12.
         5           3315%  TGGGTTGTCTA           3849949
  Noted Tags = 1          Collected Tags = 1
AAAATA, Class A, X06407, Mouse mRNA for 21 kd polypeptide
under translation
         5          .3315%TGTAGTGTAAT             3878596
  Noted Tags = 1          Collected Tags = 1
AAAGGT, Class A, X73829, M.musculus mRNA for ribosomal protein S8.
         5          .3315%TTCAGTGGACC             4009606
  Noted Tags = 0          Collected Tags = 0
         5          .3315%TTGGTGAAGGA             4110377
  Noted Tags = 2          Collected Tags = 0
         4          .2652%AGAAACCAATA              525581
  Noted Tags = 2          Collected Tags = 1
CGAACA, Class A, V00830, Mouse mRNA encoding epidermal
keratin subunit.
         4          .2652%AGTGAGGAAGA              756233
  Noted Tags = 1          Collected Tag = 0
         4          .2652%ATAATACATAA              799025
  Noted Tags = 4          Collected Tags = 0
         4          .2652%ATACTGAAGCC              817190
  Noted Tags = 1          Collected Tags = 1
CCACTT, Class A, U28917, Mus musculus 60S ribosomal
protein (A52) mRNA, com
         4          .2652%ATTCTCCAGTG             1013039
  Noted Tags = 1          Collected Tags = 0
         4          .2652%CAAACTCTCAC             1056210
  Noted Tags = 2          Collected Tags = 2
AGCGAT, Class A, X04017, Mouse mRNA for cysteine-rich
glycoprotein SPARC.
AGCGAT, Class C, M20692, Mouse osteonectin (Sparc) gene, exon 10.
         4          .2652%CAGTCACCAAC             1233218
  Noted Tags = 0          Collected Tags = 0
         4          .2652%CCCACAAGGTA             1380525
  Noted Tags = 0          Collected Tags = 0
         4          .2652%CCTTGCTCAAT             1566532
  Noted Tags = 2          Collected Tags = 1
TAAAA, Class A, M59470, Mouse cystatin C mRNA, complete cds.
         4          .2652%CCTTTGAGATC             1570958
  Noted Tags = 1          Collected Tags = 1
ATCCAC, Class A, U78085, Mus musculus ribosomal protein
S5 mRNA, complete c
         4          .2652%CTAGTCTTTGT             1882108
  Noted Tag = 1          Collected Tags = 1
ACACAA, Class A, L31609, Mus musculus (clone mcori-1ck9)
S29 ribosomal prot
         4           2652%  CTGAACATCTC           1967326
  Noted Tags = 1          Collected Tags = 1
GCCCTT, Class A, X15267, Mouse mRNA for acidic ribosomal
phosophoprotein PO
         4          .2652%GGCAAGCCCCA             2689365
  Noted Tags = 2          Collected Tags = 1
GCGTGT, Class A, U12403, Mus musculus Csa-19 mRNA, complete cds.
         4          .2652%GGCCTGGCTTA             2718333
  Noted Tags = 0          Collected Tags = 0

TABLE 12-continued

SAGE Analysis of C57BL/6 Mice Five Days After Wounding

```
SearchName = B5BANK
FileName = c:\sage\data\b5data~1\b5bank.bag
Anchoring Enzyme = NIaIII - CATG
TagLength = 11
DiTag Length = 24
Total Files = 56
Total Tags = 1508
Total Duplicate Dimers = 0
Tag Abundance Report
Total tags after excluding tags = 1508
     Count      Percent Tag Sequence      Tag Base Four Number
```

|       Count       | Percent Tag Sequence |     Tag Base Four Number     |
|-------------------|----------------------|------------------------------|
| 4                 | .2652%TCCCCGTACAT    | 3496724                      |
| Noted Tags = 0    | Collected Tags = 0   |                              |
| 4                 | .2652%TCCCTATTAAG    | 3503043                      |
| Noted Tags = 0    | Collected Tags = 0   |                              |
| 4                 | .2652%TCTTCTGACAA    | 3661073                      |
| Noted Tags = 0    | Collected Tags = 0   |                              |
| 4                 | .2652%TGGCCCAAATT    | 3822608                      |
| Noted Tags = 2    | Collected Tags = 1   |                              |

TATGCC, Class C, M11409, Mouse S16 ribosomal
protein processed pseudogene.

|       Count       | Percent Tag Sequence |     Tag Base Four Number     |
|-------------------|----------------------|------------------------------|
| 3                 | .1989%AAGGTGGAAGA    | 178697                       |
| Noted Tags = 0    | Collected Tags = 0   |                              |
| 3                 | .1989%ACATCATAGAT    | 316196                       |
| Noted Tags = 1    | Collected Tags = 1   |                              |

GACATC, Class A, L04280, Mus musculus ribosomal
protein (Rpl12) mRNA, compl

|       Count       | Percent Tag Sequence |     Tag Base Four Number     |
|-------------------|----------------------|------------------------------|
| 3                 | .1989%AGGAAGGCGGC    | 658026                       |
| Noted Tags = 0    | Collected Tags = 0   |                              |
| 3                 | .1989%CAAGTGGAAAA    | 1096193                      |
| Noted Tags = 0    | Collected Tags = 0   |                              |
| 3                 | .1989%CACGCTCCCGG    | 1154395                      |
| Noted Tags = 0    | Collected Tags = 0   |                              |
| 3                 | .1989%CAGGCCACACA    | 1217605                      |
| Noted Tags = 1    | Collected Tags = 1   |                              |

AGAGCC, Class A, AF0305, Mus musculus ATP synthase
beta-subunit (beta-F1 AT

|       Count       | Percent Tag Sequence |     Tag Base Four Number     |
|-------------------|----------------------|------------------------------|
| 3                 | .1989%CCAGAACAGAC    | 1343778                      |
| Noted Tags = 3    | Collected Tags = 0   |                              |
| 3                 | .1989%CCCAGAGCACT    | 1385032                      |
| Noted Tags = 1    | Collected Tags = 1   |                              |

GGGTTG, Class A, M10937, Mouse epidermal 67-kDa
type II keratin mRNA.

|       Count       | Percent Tag Sequence |     Tag Base Four Number     |
|-------------------|----------------------|------------------------------|
| 3                 | .1989%CCCTAAACTGA    | 1425529                      |
| Noted Tags = 0    | Collected Tags = 0   |                              |
| 3                 | .1989%CCTGATCTTTA    | 1543677                      |
| Noted Tags = 2    | Collected Tags = 2   |                              |

CTTCTA, Class A, X06406, Mouse mRNA for translational
controlled 40 kDa pol
CTTCTA, Class A, J02870, Mouse laminin receptor mRNA, complete
cds.

|       Count       | Percent Tag Sequence |     Tag Base Four Number     |
|-------------------|----------------------|------------------------------|
| 3                 | .1989%CCTTTAATCCC    | 1568982                      |
| Noted Tags = 58   | Collected Tags = 9   |                              |

AGCACT, Class A, D42051, Mus musculus mRNA for
Glutamate Decarboxylase, com
AGAGGC, Class A, X79508, M.musculus (C57BL/10) CW37 mRNA,
B1 repeat.
AGCACT, Class A, U03421, Mus musculus interleukin-11 mRNA,
complete cds.
AGTTAC, Class C, U59807, Mus musculus cystatin B (Stfb) gene.
complete cds.
AGCACT, Class A, M58288, Mus musculus granulocyte
colony-stimulating factor
AGCACC, Class C, M14361, Mouse Ig germline kappa-chain
V-region gene V-Ser,
AGCAAT, Class C, M93320, Mus musculus DNA fragment,
L1 repeat family region
AGCCCT, Class C, J00632, mouse b1 ubiquitous repeat
(copy c) mrna and flank
AGGACT, Class A, L08394, Mus musculus betacellulin
(bcn) mRNA, complete cds

|       Count       | Percent Tag Sequence |     Tag Base Four Number     |
|-------------------|----------------------|------------------------------|
| 3                 | .1989%CTCAACAGCAA    | 1901713                      |
| Noted Tags = 0    | Collected Tags = 0   |                              |
| 3                 | 1989%   CTCCTGGACAC  | 1931794                      |
| Noted Tags = 1    | Collected Tags = 1   |                              |

CTGGGA, Class A, J04953, Mouse gelsolin gene, complete cds.

TABLE 12-continued

SAGE Analysis of C57BL/6 Mice Five Days After Wounding

```
SearchName = B5BANK
FileName = c:\sage\data\b5data~1\b5bank.bag
Anchoring Enzyme = NIaIII - CATG
TagLength = 11
DiTag Length = 24
Total Files = 56
Total Tags = 1508
Total Duplicate Dimers = 0
Tag Abundance Report
Total tags after excluding tags = 1508
     Count        Percent Tag Sequence         Tag Base Four Number
```

|  |  |  |
|---|---|---|
| 3 | .1989%CTGGCTTTCAG | 2006995 |
| Noted Tags = 0 | Collected Tags = 0 | |
| 3 | .1989%GACTTTGGAAA | 2227841 |
| Noted Tags = 6 | Collected Tags = 3 | |

ACATTT, Class A, U03419, Mus musculus alpha-1
type I procollagen mRNA, part
ACATTT, Class C, X57981, Mouse gene for pro alpha1
(I) collagen chain (COL1
ACATTT, Class A, U08020, Mus musculus FVB/N collagen
pro-alpha-1 type I cha

|  |  |  |
|---|---|---|
| 3 | .1989%GAGCGTTTTGG | 2256891 |
| Noted Tags = 2 | Collected Tags = 1 | |

GTCCAG, Class A, X52803, Mouse mRNA for cyclophilin (EC 5.2.1.8).

|  |  |  |
|---|---|---|
| 3 | .1989%GATGACACCAG | 2327635 |
| Noted Tags = 1 | Collected Tags = 1 | |

CCGCTC, Class A, U11248, Mus musculus C57BL/6J
ribosomal protein S28 mRNA,

|  |  |  |
|---|---|---|
| 3 | 1989% GCTGCAGTTGA | 2593529 |
| Noted Tags = 0 | Collected Tags = 0 | |
| 3 | .1989%GCTGCCCTCCA | 2594261 |
| Noted Tags = 5 | Collected Tags = 0 | |
| 3 | 1989% GTCTGCTGATG | 3008399 |
| Noted Tags = 2 | Collected Tags = 2 | |

GCCAGA, Class A, X75313, M.musculus (C57BL/6) GB-like mRNA.
GCCAGA, Class A, D29802, Mouse mRNA for G protein beta
subunit homologue, c

|  |  |  |
|---|---|---|
| 3 | .1989%GTGGAGGCGCC | 3050086 |
| Noted Tags = 0 | Collected Tags = 0 | |
| 3 | .1989%GTGGGCGTGTA | 3057389 |
| Noted Tags = 1 | Collected Tags = 1 | |

CAACGG, Class A, M33330, Mouse insulinoma (rig) mRNA,
complete cds.

|  |  |  |
|---|---|---|
| 3 | .1989%TAAACCTGCTA | 3151773 |
| Noted Tags = 0 | Collected Tags = 0 | |
| 3 | .1989%TATCCCACGCC | 3363942 |
| Noted Tags = 0 | Collected Tags = 0 | |
| 3 | .1989%TCGGTTTCTGC | 3587962 |
| Noted Tags = 0 | Collected Tags = 0 | |
| 3 | .1989%TCTCACCACCC | 3622166 |
| Noted Tags = 0 | Collected Tags = 0 | |
| 3 | .1989%TGAGCCCGGGA | 3691945 |
| Noted Tags = 0 | Collected Tags = 0 | |
| 3 | .1989%TGCACAGTGCT | 3740392 |
| Noted Tags = 5 | Collected Tags = 4 | |

GAGCAA, Class A, X05835, Mouse mRNA for placental
calcium-binding protein.
GAGCAA, Class A, X16190, Mouse mts1 gene.
GAGCAA, Class A, Z36947, Murine retrovirus RNA
containing parts of mts1 of
GAGCAA, Class A, D00208, Mus musculus mRNA
for pEL98 protein, complete cds.

|  |  |  |
|---|---|---|
| 3 | .1989%TGGTCTGGTCC | 3858102 |
| Noted Tags = 0 | Collected Tags = 0 | |
| 3 | .1989%TGTAACAGGAC | 3867810 |
| Noted Tags = 1 | Collected Tags = 1 | |

TGCTAT, Class A, X04648, Mouse mRNA for IgG1/IgG2b
Fc receptor (FcR).

|  |  |  |
|---|---|---|
| 3 | .1989%TTCAGGTGGTT | 4008880 |
| Noted Tags = 1 | Collected Tags = 1 | |

TCTTCT, Class A, X73607, M.musculus mRNA
for tropomyosin 5(3'UTR).

|  |  |  |
|---|---|---|
| 3 | .1989%TTGGCTGCCCA | 4103765 |
| Noted Tags = 1 | Collected Tags = 1 | |

GGATCT, Class C, Y08307, M.musculus mitochondrial
mRNA for ribosomal protei

TABLE 12-continued

SAGE Analysis of C57BL/6 Mice Five Days After Wounding

```
SearchName = B5BANK
FileName = c:\sage\data\b5data~1\b5bank.bag
Anchoring Enzyme = NIaIII - CATG
TagLength = 11
DiTag Length = 24
Total Files = 56
Total Tags = 1508
Total Duplicate Dimers = 0
Tag Abundance Report
Total tags after excluding tags = 1508
     Count      Percent Tag Sequence      Tag Base Four Number
```

|       |            |                    |         |
|-------|------------|--------------------|---------|
| 2     | .1326%     | AAAACAGTGGC        | 4842    |

Noted Tags = 1          Collected Tags = 1
CGGTGG, Class A, X73331, M.musculus mRNA
for ribosomal protein L37a.

|   |        |             |       |
|---|--------|-------------|-------|
| 2 | 1326%  | AAAGCAGTGCT | 37608 |

Noted Tags = 0          Collected Tags = 0

| 2 | .1326% | AAGAGGCAAGA | 141577 |

Noted Tags = 0          Collected Tags = 0

| 2 | .1326% | AAGCAACAGGT | 147756 |

Noted Tags = 0          Collected Tags = 0

| 2 | .1326% | AAGGTCGAGCT | 177704 |

Noted Tags = 0          Collected Tags = 0

| 2 | .1326% | ACAGAACTCTT | 295392 |

Noted Tags = 1          Collected Tags = 1
CTCAAT, Class A, AJ0023, Mus musculus mRNA for annexin VIII.

| 2 | .1326% | ACCTTGGAAGG | 391691 |

Noted Tags = 1          Collected Tags = 0

| 2 | .1326% | ACTCTTTGTTT | 491456 |

Noted Tags = 0          Collected Tags = 0

| 2 | .1326% | ACTGGCTGGGC | 501674 |

Noted Tags = 0          Collected Tags = 0

| 2 | .1326% | ACTTATTATGC | 511802 |

Noted Tags = 0          Collected Tags = 0

| 2 | .1326% | AGAACCATTAA | 529649 |

Noted Tags = 0          Collected Tags = 0

| 2 | .1326% | AGACCCTCTCA | 546677 |

Noted Tags = 0          Collected Tags = 0

| 2 | .1326% | AGCAATTCAAA | 593729 |

Noted Tags = 6          Collected Tags = 2
CAATTA, Class C, U09637, Mus musculus domesticus
mitochondrion NADH dehydro
CAATTA, Class C, U09638, Mus musculus
musculus mitochondrion NADH dehydroge

| 2 | .1326% | ATCAACACCGC | 853082 |

Noted Tags = 2          Collected Tags = 2
AACCTT, Class A, Y00703, Mouse uncoupled S49 cells
mRNA for stimulatory GTP
AACCTT, Class A, M13964, Mouse stimulatory G protein
of adenylate cyclase,

| 2 | .1326% | ATCCGAAAGAT | 876580 |

Noted Tags = 2          Collected Tags = 1
GAAGCT, Class A, L04128, Mus musculus ribosomal
protein L18 (rpL18) mRNA, c

| 2 | .1326% | CACCACCACAG | 1131795 |

Noted Tags = 1          Collected Tags = 1
GATCAA, Class A, X05021, Murine mRNA with
homology to yeast L29 ribosomal p

| 2 | .1326% | CACCTTGGTGC | 1146554 |

Noted Tags = 0          Collected Tags = 0

| 2 | .1326% | CACGGGACCAC | 1157202 |

Noted Tags = 0          Collected Tags = 0

| 2 | .1326% | CACTGACCTCC | 1171830 |

Noted Tags = 1          Collected Tags = 0

| 2 | .1326% | CATTATGGGTG | 1298095 |

Noted Tags = 3          Collected Tags = 3
GCAAGA, Class A, U16818, Mus musculus UDP
glucuronosyltransferase (UGT1-06)
GCAAGA, Class A, L02333, Murine bilirubin/phenol
family UDP glucuronosyltra
GCAAGA, Class A, 127122, Mus musculus (A-1)
bilirubin/phenol UDP-glucuronos

| 2 | .1326% | CCCAATGGCCC | 1379990 |

Noted Tags = 3          Collected Tags = 3
AATAAA, Class A, X65582, M.musculus mRNA for
alpha-2 collagen VI.

TABLE 12-continued

SAGE Analysis of C57BL/6 Mice Five Days After Wounding

```
SearchName = B5BANK
FileName = c:\sage\data\b5data~1\b5bank.bag
Anchoring Enzyme = NIaIII - CATG
TagLength = 11
DiTag Length = 24
Total Files = 56
Total Tags = 1508
Total Duplicate Dimers = 0
Tag Abundance Report
Total tags after excluding tags = 1508
     Count      Percent Tag Sequence          Tag Base Four Number
```

AATAAA, Class A, X62332, M.musculus mRNA for
alpha-2 collagen type VI, subu
AATAAA, Class A, Z18272, Mus musculus collagen alpha 2 chain type
VI.
```
        2          .1326% CCCGGACTTAC               1417714
 Noted Tags = 2           Collected Tags = 0
        2          .1326% CCCGTAGCCCC               1421910
 Noted Tags = 1           Collected Tags = 1
```
TTCCGA, Class A, M22479, Mouse tropomyosin
isoform 2 mRNA, complete cds.
```
        2          .1326% CCTACAGTTGA               1512185
 Noted Tags = 3           Collected Tags = 3
```
TAATCT, Class C. K02241, Mouse alkali myosin
light chains, exons 6 and 7 co
TAATCT, Class A, K02242, Mouse alkali myosin
light chains MLC1f and MLC3f 3
TAATCT, Class C, K02243, Mouse alkali myosin
light chains MLC1f/MLC3f pseud
```
        2          .1326% CCTCGGAAAAT               1533956
 Noted Tags = 0           Collected Tags = 0
        2          .1326% CCTGTGTGAAA               1555329
 Noted Tags = 0           Collected Tags = 0
        2          .1326% CGCCTGCTAGC               1669578
 Noted Tags = 2           Collected Tags = 1
```
CAACCG, Class A, X58251, Mouse COL1A2 mRNA for
pro-alpha-2(I) collagen
```
        2          .1326% CGCTGGTTCCA               1698773
 Noted Tags = 2           Collected Tags = 0
        2          .1326% CGGTTCCACCC               1766678
 Noted Tags = 0           Collected Tags = 0
        2          .1326% CTAATAAAGCC               1847334
 Noted Tags = 3           Collected Tags = 2
```
ACTGTG, Class A, X659229, M.musculus fau mRNA.
ACTGTG, Class A, D26610, Mouse mRNA for
monoclonal nonspecific suppressor f
```
        2          .1326% CTACCAGGATA               1856141
 Noted Tags = 0           Collected Tags = 0
        2          .1326% CTGCTATCCGA               1995609
 Noted Tags = 1           Collected Tags = 1
```
GAGAAT, Class A, X83590, M.musculus mRNA for
ribosomal protein L5, 3'end.
```
        2          .1326% CTGCTTTGTGC               1998778
 Noted Tags = 2           Collected Tags = 2
```
TGTACA, Class A, M13227, Mouse enkephalin mRNA.
TGTACA, Class A, M55181, Mouse spermatogenic-specific
proenkephalin mRNA, c
```
        2          .1326% CTGGGCGTGTC               2008814
 Noted Tags = 0           Collected Tags = 0
        2          .1326% CTGTAGGTGAT               2018020
 Noted Tags = 0           Collected Tags = 0
        2          .1326% CTGTGCCCTCC               2024822
 Noted Tags = 0           Collected Tags = 0
        2          .1326% CTTAAGGATCC               2034230
 Noted Tags = 0           Collected Tags = 0
        2          .1326% GAATCTGAAGT               2153996
 Noted Tags = 0           Collected Tags = 0
        2          .1326% GAATGCAGGGA               2155689
 Noted Tags = 0           Collected Tags = 0
        2          .1326% GAGGAGAAGAA               2263073
 Noted Tags = 2           Collected Tags = 1
```
AGCATT, Class A, Y00225, Murine mRNA for
J1 protein, yeast ribosomal protei
```
        2          .1326% GATGCATAGTG               2331439
 Noted Tags = 1           Collected Tags = 0
        2          .1326% GATGTGACCAC               2340946
```

TABLE 12-continued

SAGE Analysis of C57BL/6 Mice Five Days After Wounding

```
SearchName = B5BANK
FileName = c:\sage\data\b5data~1\b5bank.bag
Anchoring Enzyme = NIaIII - CATG
TagLength = 11
DiTag Length = 24
Total Files = 56
Total Tags = 1508
Total Duplicate Dimers = 0
Tag Abundance Report
Total tags after excluding tags = 1508
     Count      Percent Tag Sequence        Tag Base Four Number
```

| | | | |
|---|---|---|---|
| Noted Tags = 0 | | Collected Tags = 0 | |
| | 2 | .1326%GATTTCTGTCT | 2357176 |
| Noted Tags = 0 | | Collected Tags = 0 | |
| | 2 | .1326%GCACCGAACAC | 2381842 |
| Noted Tags = 0 | | Collected Tags = 0 | |
| | 2 | .1326%GCATACGGCGC | 2410138 |
| Noted Tags = 1 | | Collected Tags = 0 | |
| | 2 | .1326%GCATTGCATCT | 2423096 |
| Noted Tags = 0 | | Collected Tags = 0 | |
| | 2 | .1326%GCCAAGGGTCA | 2427573 |
| Noted Tags = 1 | | Collected Tags = 1 | |

GAGGCT, Class A, L08651, Mus musculus large
ribosomal subunit protein mRNA,

| | | | |
|---|---|---|---|
| | 2 | .1326%GCCAAGTGGAG | 2427811 |
| Noted Tags = 5 | | Collected Tags = 1 | |

TTCCCA, Class A, M76131, Mouse elongation
factor 2 (ef-2) mRNA, 3' end.

| | | | |
|---|---|---|---|
| | 2 | 1326%    GCCTAATGTAC | 2474930 |
| Noted Tags = 1 | | Collected Tags = 1 | |

ACAAAG, Class A, U93863, Mus musculus
ribosomal protein L21 mRNA, complete

| | | | |
|---|---|---|---|
| | 2 | .1326%GCCTCGGGGGA | 2480809 |
| Noted Tags = 0 | | Collected Tags = 0 | |
| | 2 | .1326%GCGACGCGGGC | 2496938 |
| Noted Tags = 0 | | Collected Tags = 0 | |
| | 2 | .1326%GCGGCGGGATG | 2529935 |
| Noted Tags = 0 | | Collected Tags = 0 | |
| | 2 | .1326%GCTCAGGATTC | 2574910 |
| Noted Tags = 1 | | Collected Tags = 1 | |

ATCTGA, Class A, X91824, M.musculus mRNA for SPRR1a protein.

| | | | |
|---|---|---|---|
| | 2 | .1326%GCTGGCAGACG | 2598023 |
| Noted Tags = 0 | | Collected Tags = 0 | |
| | 2 | .1326%GCTTGCTTCCT | 2615256 |
| Noted Tags = 1 | | Collected Tags = 1 | |

GGAGCA, Class A, X89650, M.musculus mRNA for Rab7 protein.

| | | | |
|---|---|---|---|
| | 2 | .1326%GGAAGGTGTCT | 2632632 |
| Noted Tags = 1 | | Collected Tags = 1 | |
| | 2 | .1326%GGATTTGGCTT | 2686624 |
| Noted Tags = 0 | | Collected Tags = 0 | |
| | 2 | .1326%GGGAGCTGTGC | 2762682 |
| Noted Tags = 0 | | Collected Tags = 0 | |
| | 2 | .1326%GGGGAAATCGC | 2785498 |
| Noted Tags = 1 | | Collected Tags = 1 | |

CAGCTT, Class A, Z48496, M.musculus mRNA for
testis-specific thymosin beta-

| | | | |
|---|---|---|---|
| | 2 | .1326%GGGGCTCAGCC | 2792742 |
| Noted Tags = 2 | | Collected Tags = 0 | |
| | 2 | .1326%GGTGAGCCTGA | 2853241 |
| Noted Tags = 1 | | Collected Tags = 1 | |

AGCTTG, Class A, U20611, Mus musculus
thioredoxin-dependent peroxide reduct

| | | | |
|---|---|---|---|
| | 2 | .1326%GGTGGGACACA | 2861125 |
| Noted Tags = 0 | | Collected Tags = 0 | |
| | 2 | .1326%GTAAGCATAAA | 2892993 |
| Noted Tags = 0 | | Collected Tags = 0 | |
| | 2 | .1326%GTCTGGGGGGA | 3009193 |
| Noted Tags = 0 | | Collected Tags = 0 | |
| | 2 | .1326%GTGGTAGGCTA | 3060381 |
| Noted Tags = 0 | | Collected Tags = 0 | |
| | 2 | .1326%GTTGCTGAGAA | 3120673 |
| Noted Tags = 2 | | Collected Tags = 2 | |

GCGGCT, Class A, X75312, M.musculus (C57BL/6) QM mRNA.
GCGGCT, Class A, M93980, Mouse 24.6 kda protein mRNA, complete cds.

| | | | |
|---|---|---|---|
| | 2 | .1326%GTTGGGGGGGG | 3123883 |

TABLE 12-continued

SAGE Analysis of C57BL/6 Mice Five Days After Wounding

```
SearchName = B5BANK
FileName = c:\sage\data\b5data~1\b5bank.bag
Anchoring Enzyme = NIaIII - CATG
TagLength = 11
DiTag Length = 24
Total Files = 56
Total Tags = 1508
Total Duplicate Dimers = 0
Tag Abundance Report
Total tags after excluding tags = 1508
     Count      Percent Tag Sequence       Tag Base Four Number
```

|  |  |  |  |
| --- | --- | --- | --- |
| Noted Tags = 0 |  | Collected Tags = 0 |  |
| 2 | .1326% | TAACTGACAAT | 3176516 |
| Noted Tags = 1 |  | Collected Tags = 0 |  |
| 2 | .1326% | TATACAATACA | 3346629 |
| Noted Tags = 0 |  | Collected Tags = 0 |  |
| 2 | .1326% | TCCACTGTGCA | 3481317 |
| Noted Tags = 1 |  | Collected Tags = 1 |  |
| CGTGTG, Class C, L38580, Mus musculus galanin gene, | | | |
| exon 6 and complete cds | | | |
| 2 | .1326% | TCTGGACGCGG | 3645851 |
| Noted Tags = 2 |  | Collected Tags = 2 |  |
| AAAGCA, Class C, M33988, Mouse histone H2A.1 gene, complete cds. | | | |
| CAAGCA, Class C, M37736, Mouse replication-dependent histone H2A.1 | | | |
| gene. | | | |
| 2 | .1326% | TGAAACACTGT | 3671164 |
| Noted Tags = 2 |  | Collected Tags = 2 |  |
| , Class A, D86344, Mouse mRNA for | | | |
| Topoisomerase-inhibitor suppressed, | | | |
| T, Class A, D50465, Mouse MA-3 (apoptosis-related gene) | | | |
| mRNA, complete | | | |
| 2 | .1326% | TGACCCCGGGT | 3691948 |
| Noted Tags = 0 |  | Collected Tags = 0 |  |
| 2 | .1326% | TGCCTGTGATA | 3767181 |
| Noted Tags = 0 |  | Collected Tags = 0 |  |
| 2 | .1326% | TGGATCCTGAG | 3814883 |
| Noted Tags = 21 |  | Collected Tags = 4 |  |
| AACTTC, Class C, V00742, Fragment of the mouse | | | |
| gene for epsilon-globin Y3 ( | | | |
| AACTTC, Class A, M19236 Mouse beta-globin gene. | | | |
| AACTTC, Class C, J00414, Mouse beta-globin epsilon | | | |
| y3 gene, exon 2. | | | |
| AACTTC, Class C, M10688, Mouse beta-globin gene | | | |
| with intron boundary. | | | |
| 2 | .1326% | TGGGCAAAGCC | 3837990 |
| Noted Tags = 0 |  | Collected Tags = 0 |  |
| 2 | .1326% | TGGTGACAAAA | 3858689 |
| Noted Tags = 0 |  | Collected Tags = 0 |  |
| 2 | .1326% | TGTGCCAAGTG | 3904559 |
| Noted Tags = 0 |  | Collected Tags = 0 |  |
| 2 | .1326% | TGTTCATCTTG | 3920767 |
| Noted Tags = 2 |  | Collected Tags = 1 |  |
| TTTTAA, Class C, X57983, Mouse gene for | | | |
| pro alpha1 (III) collage chain (CO | | | |
| 2 | .1326% | TTCAGCTCGAG | 4007779 |
| Noted Tags = 0 |  | Collected Tags = 0 |  |
| 2 | .1326% | TTGCTGCAGTG | 4094255 |
| Noted Tags = 0 |  | Collected Tags = 0 |  |

TABLE 13

SAGE Analysis of MRL Mice Five Days After Wounding

```
SearchName = C5BANK
FileName = c:\sage\data\c5data.2\tagbank.bag
Anchoring Enzyme = NlaIII - CATG
Tag Length = 11
DiTag Length = 24
Total Files = 67
Total Tags = 1790
Total Duplicate Dimers = 0
Tag Abundance Report
Total tags after excluding tags = 1790
```

TABLE 13-continued

SAGE Analysis of MRL Mice Five Days After Wounding

| Count | Percent | Tag Sequence | Tag BaseFour Number | SEQ ID NO: |
|---|---|---|---|---|
| 23 | 1.2849 | CGGTCCAGGGA | 1758377 | 162 |
| 18 | 1.0055 | GTGGCTCACAA | 3054865 | 163 |
| 16 | .8938 | GGCTTCGGTCT | 2750136 | 164 |
| 14 | .7821 | AGGTCGGGTGG | 711355 | 165 |
| 13 | .7262 | CACAAACGGTA | 1114541 | 166 |
| 13 | .7262 | TGGGTTGTCTA | 3849949 | 167 |
| 12 | .6703 | CGCCGCCGGCT | 1664424 | 168 |
| 12 | .6703 | CTGCTCAGGCT | 1995944 | 169 |
| 12 | .6703 | GCTGGCCCTTC | 2598270 | 170 |
| 11 | .6145 | AGGCAGACAGT | 673868 | 171 |
| 11 | .6145 | TTGGCTGCCCA | 4103765 | 172 |
| 10 | .5586 | GCCCGGGAATA | 2451981 | 173 |
| 9 | .5027 | AGAGCGAAGTG | 563247 | 174 |
| 9 | .5027 | CAGAACCCACG | 1180999 | 175 |
| 9 | .5027 | CATCGCCAGTC | 1271087 | 176 |
| 9 | .5027 | CCCCAGCCAGT | 1395020 | 177 |
| 8 | .4469 | AGCAGTCCCCT | 601432 | 178 |
| 8 | .4469 | CAAACTCTCAC | 1056210 | 179 |
| 8 | .4469 | CTAATAAAGCC | 1847334 | 180 |
| 8 | .4469 | GGCAAGCCCCA | 2689365 | 181 |
| 7 | .391 | CAAGGTGACAG | 1093139 | 182 |
| 7 | .391 | CCAGAACAGAC | 1343778 | 183 |
| 7 | .391 | CTGAACATCTC | 1967326 | 184 |
| 7 | .391 | GCCTTTATGAG | 2489571 | 185 |
| 7 | .391 | GGAAGCCACTT | 2630944 | 186 |
| 7 | .391 | GTGAACGTGCC | 3016422 | 187 |
| 7 | .391 | GTGGGCGTGTA | 3057389 | 188 |
| 6 | .3351 | AACACCAAGCT | 70696 | 189 |
| 6 | .3351 | CACCACCACAG | 1131795 | 190 |
| 6 | .3351 | CACCACCGTTG | 1131967 | 191 |
| 6 | .3351 | CACGCTCCCGG | 1154395 | 192 |
| 6 | .3351 | CCCGTGTGCTC | 1424286 | 193 |
| 6 | .3351 | CCTTGCTCAAT | 1566532 | 194 |
| 6 | .3351 | CTGCTATCCGA | 1995609 | 195 |
| 6 | .3351 | GAACATTGCAC | 2117522 | 196 |
| 6 | .3351 | GGATTTGGCTT | 2686624 | 197 |
| 6 | .3351 | GGGAAGGCGGC | 2755178 | 198 |
| 6 | .3351 | GTCTGCTGATG | 3008399 | 199 |
| 6 | .3351 | TCACGCTGCCT | 3450776 | 200 |
| 6 | .3351 | TGGATCCTGAG | 3814883 | 201 |
| 5 | .2793 | CGCTGGTTCCA | 1698773 | 202 |
| 5 | .2793 | CTCCTGGACAC | 1931794 | 203 |
| 5 | .2793 | TATGTCAAGCT | 3388456 | 204 |
| 5 | .2793 | TCGTGATTGTG | 3597295 | 205 |
| 5 | .2793 | TTCAGTGGACC | 4009606 | 206 |
| 4 | .2234 | AAGAGGCAAGA | 141577 | 207 |
| 4 | .2234 | ATACTGACATT | 817232 | 208 |
| 4 | .2234 | CAAGTGGAAAA | 1096193 | 209 |
| 4 | .2234 | CCCAATGGCCC | 1379990 | 210 |
| 4 | .2234 | CCTACCAAGAC | 1512482 | 211 |
| 4 | .2234 | GATGACACCAG | 2327635 | 212 |
| 4 | .2234 | GATTCCGTGAG | 2348771 | 213 |
| 4 | .2234 | GCAGAGTGCGC | 2395034 | 214 |
| 4 | .2234 | GCCAAGTGGAG | 2427811 | 215 |
| 4 | .2234 | GCGGCGGATGG | 2529851 | 216 |
| 4 | .2234 | GTGGAGGCGCC | 3050086 | 217 |
| 4 | .2234 | TGCACAGTGCT | 3740392 | 218 |
| 4 | .2234 | TGGATCAGTCT | 3814584 | 219 |
| 4 | .2234 | TGGCTCGGTCA | 3831477 | 220 |
| 4 | .2234 | TGTGCCAAGTG | 3904559 | 221 |
| 4 | .2234 | TTCTTTGGTGA | 4062905 | 222 |
| 3 | .1675 | AGTGAGGAAGA | 756233 | 223 |
| 3 | .1675 | CACCTTGGTGC | 1146554 | 224 |
| 3 | .1675 | CCCTGAGTCCA | 1434325 | 225 |
| 3 | .1675 | CTACCACTCAA | 1855953 | 226 |
| 3 | .1675 | CTGAGAGAGAA | 1974817 | 227 |
| 3 | .1675 | CTGTAGACTGC | 2017402 | 228 |
| 3 | .1675 | CTGTAGGTGAT | 2018020 | 229 |
| 3 | .1675 | CTTGCACACACA | 2065477 | 230 |
| 3 | .1675 | GAGTCTCCCTG | 2284895 | 231 |
| 3 | .1675 | GATGTGGCTGC | 2341498 | 232 |
| 3 | .1675 | GCCGCTAGGCC | 2464934 | 233 |
| 3 | .1675 | GCCTGTGGCCT | 2485912 | 234 |
| 3 | .1675 | GCGCCCTCCCC | 2512726 | 235 |

TABLE 13-continued

SAGE Analysis of MRL Mice Five Days After Wounding

| | | | | |
|---|---|---|---|---|
| 3 | .1675 | GGGGGCCCAGG | 2794827 | 236 |
| 3 | .1675 | GTGTGGGCACT | 3074632 | 237 |
| 3 | .1675 | GTGTTAACCAG | 3076179 | 238 |
| 3 | .1675 | TAAAGAGGCCG | 3154583 | 239 |
| 3 | .1675 | TGCTTATGATG | 3797903 | 240 |
| 3 | .1675 | TGGTGACAAAA | 3858689 | 241 |
| 3 | .1675 | TGTCAGTCTGT | 3885948 | 242 |
| 3 | .1675 | TTCAGCTCGAG | 4007779 | 243 |
| 2 | .1117 | AACAATTTGGG | 69611 | 244 |
| 2 | .1117 | AACAGGTTCAA | 76753 | 245 |
| 2 | .1117 | AAGCGCCTCAC | 157138 | 246 |
| 2 | .1117 | AAGGAAATGGG | 164075 | 247 |
| 2 | .1117 | AAGGTCTGCCT | 178072 | 248 |
| 2 | .1117 | AAGGTGGAAGA | 178697 | 249 |
| 2 | .1117 | ACAGTTCCAGA | 310601 | 250 |
| 2 | .1117 | ACCCTCCTCCC | 357846 | 251 |
| 2 | .1117 | AGAGGAAGCTG | 565407 | 252 |
| 2 | .1117 | AGCAGGGATCC | 600630 | 253 |
| 2 | .1117 | AGGAAGGCGGC | 658026 | 254 |
| 2 | .1117 | AGGGAGCGCTA | 690589 | 255 |
| 2 | .1117 | AGTGACTCTGG | 755579 | 256 |
| 2 | .1117 | ATTCTCCAGTG | 1013039 | 257 |
| 2 | .1117 | ATTTGATTAGC | 1041354 | 258 |
| 2 | .1117 | ATTTTCCAGTG | 1045807 | 259 |
| 2 | .1117 | CAATGTGGGTT | 1109680 | 260 |
| 2 | .1117 | CACAGACTGTG | 1122799 | 261 |
| 2 | .1117 | CACAGCCCACT | 1123656 | 262 |
| 2 | .1117 | CACCGCCAGTG | 1140015 | 263 |
| 2 | .1117 | CACGGCTTTCA | 1157109 | 264 |
| 2 | .1117 | CACGGGACCAC | 1157202 | 265 |
| 2 | .1117 | CAGTCACCAAC | 1233218 | 266 |
| 2 | .1117 | CAGTCTCTCAA | 1236433 | 267 |
| 2 | .1117 | CCAACGCTTTA | 1317373 | 268 |
| 2 | .1117 | CCACCTCCTGT | 1334652 | 269 |
| 2 | .1117 | CCCAGGCTGAA | 1386977 | 270 |
| 2 | .1117 | CCCTAAACTGA | 1425529 | 271 |
| 2 | .1117 | CCCTCTACAAG | 1432643 | 272 |
| 2 | .1117 | CCCTGGGTTCT | 1436408 | 273 |
| 2 | .1117 | CCCTGTGGCCG | 1437335 | 274 |
| 2 | .1117 | CCCTTCTTCTC | 1439710 | 275 |
| 2 | .1117 | CCGCCTGCAAG | 1465923 | 276 |
| 2 | .1117 | CCTCAGCCTGG | 1526139 | 277 |
| 2 | .1117 | CCTCGCACAGT | 1533004 | 278 |
| 2 | .1117 | CCTTTAATCCC | 1568982 | 279 |
| 2 | .1117 | CCTTTGTGACT | 1571720 | 280 |
| 2 | .1117 | CGCCTGCTAGC | 1669578 | 281 |
| 2 | .1117 | CTGAGAGAAAA | 1974785 | 282 |
| 2 | .1117 | CTGCCTCACAG | 1989907 | 283 |
| 2 | .1117 | CTGCGAGATTC | 1991230 | 284 |
| 2 | .1117 | CTGCTTTGTGC | 1998778 | 285 |
| 2 | .1117 | CTGTCTGAAAG | 2022915 | 286 |
| 2 | .1117 | CTTCTCATTTG | 2061567 | 287 |
| 2 | .1117 | CTTGCTCAATG | 2071823 | 288 |
| 2 | .1117 | CTTGGCGAGCG | 2074151 | 289 |
| 2 | .1117 | GAAAGTTGGCC | 2109350 | 290 |
| 2 | .1117 | GAACGCGACGG | 2123291 | 291 |
| 2 | .1117 | GACTTTGGAAA | 2227841 | 292 |
| 2 | .1117 | GAGTTTTCACG | 2293575 | 293 |
| 2 | .1117 | GCACAACTTGC | 2376186 | 294 |
| 2 | .1117 | GCACTGCGCAC | 2390418 | 295 |
| 2 | .1117 | GCCCCCGCATA | 2446925 | 296 |
| 2 | .1117 | GCCCCTGCGCA | 2448997 | 297 |
| 2 | .1117 | GCCTAATGTAC | 2474930 | 298 |
| 2 | .1117 | GCCTCCTCCCA | 2479957 | 299 |
| 2 | .1117 | GCCTTGGTGAA | 2489057 | 300 |
| 2 | .1117 | GCGAAGCTCAG | 2492883 | 301 |
| 2 | .1117 | GCGGCGCCGCA | 2529637 | 302 |
| 2 | .1117 | GCTCTCCAGCA | 2585893 | 303 |
| 2 | .1117 | GCTGCCCTCCA | 2594261 | 304 |
| 2 | .1117 | GCTGTGGCCAC | 2603602 | 305 |
| 2 | .1117 | GGCAGCCCCCT | 2696536 | 306 |
| 2 | .1117 | GGCTGGGGGCT | 2747048 | 307 |
| 2 | .1117 | GGGCCTGTGGG | 2776811 | 308 |
| 2 | .1117 | GGTGCCAACTA | 2855965 | 309 |
| 2 | .1117 | GGTGGGGGGGC | 2861738 | 310 |
| 2 | .1117 | GTCACAGGCAA | 2953873 | 311 |
| 2 | .1117 | GTCTGCGTGCC | 3008230 | 312 |

TABLE 13-continued

SAGE Analysis of MRL Mice Five Days After Wounding

| | | | | |
|---|---|---|---|---|
| 2 | .1117 | GTCTGGGGGA | 3009193 | 313 |
| 2 | .1117 | GTCTGTGCCCA | 3010133 | 314 |
| 2 | .1117 | GTGAGCCCATT | 3024208 | 315 |
| 2 | .1117 | GTGGCGCACGC | 3053850 | 316 |
| 2 | .1117 | GTGGCTCACAG | 3054867 | 317 |
| 2 | .1117 | GTGGGTGTTGG | 3059451 | 318 |
| 2 | .1117 | TATCTGTGCAT | 3373972 | 319 |
| 2 | .1117 | TATTGGCTCTG | 3402207 | 320 |
| 2 | .1117 | TCACTGGCCCC | 3439190 | 321 |
| 2 | .1117 | TCCAACTCCTT | 3475296 | 322 |
| 2 | .1117 | TCCCTGTGGTT | 3505072 | 323 |
| 2 | .1117 | TCCGGGCGAGG | 3516811 | 324 |
| 2 | .1117 | TCTCACCACCC | 3622166 | 325 |
| 2 | .1117 | TCTGCCAATTT | 3642432 | 326 |
| 2 | .1117 | TCTGGACGCGG | 3645851 | 327 |
| 2 | .1117 | TCTTCTCACAA | 3661073 | 328 |
| 2 | .1117 | TGAACCGTCCC | 3675862 | 329 |
| 2 | .1117 | TGACAGCTGCC | 3688934 | 330 |
| 2 | .1117 | TGACCCCGGGC | 3691946 | 331 |
| 2 | .1117 | TGACCCCGGGT | 3691948 | 332 |
| 2 | .1117 | TGAGCATCGGG | 3707755 | 333 |
| 2 | .1117 | TGCGTGCTGGA | 3783145 | 334 |
| 2 | .1117 | TGGCCCAAATT | 3822608 | 335 |
| 2 | .1117 | TGTAACAGGAC | 3867810 | 336 |
| 2 | .1117 | TGTAACTGGTC | 3868590 | 337 |
| 2 | .1117 | TGTGAACTTTG | 3899903 | 338 |
| 2 | .1117 | TGTTCATCTTG | 3920767 | 339 |
| 2 | .1117 | TTCAGCTCGAA | 4007777 | 340 |
| 2 | .1117 | TTCTGTCCTGT | 4058492 | 341 |
| 2 | .1117 | TTGCACCTTCT | 4081144 | 342 |
| 2 | .1117 | TTGGGCCAGAG | 4105507 | 343 |
| 2 | .1117 | TTGGTGAAGGA | 4110377 | 344 |
| 2 | .1117 | TTTCGTGTTGG | 4157179 | 345 |
| 2 | .1117 | TTTTCCACTTG | 4183167 | 346 |

Tags included in this report = 185
    DataBase Link
    Database = c:
23    1.2849%    CGGTCCAGGGA (SEQ ID NO:162)              1758377
Noted Tags = 0    Collected Tags = 0
18    1.0055%    GTGGCTCACAA (SEQ ID NO:163)              3054865
Noted Tags = 207 Collected Tags = 56
CCATCC, Class A, AB0046, Mus musculus mRNA for Rab33B, complete cds.
CCATCT, Class C, L29190, Mouse MHC class I H2-D transplantation antigen gen
CCATCT, Class A, U20225, Mus musculus adenylosuccinate lyase (adi) mRNA, co
CCATCT, Class A, X93168, M. musculus mRNA for cannabinoid receptor 2.
CCATCT, Class A, X56974, M. musculus mRNA for external transcribed spacer (p
CCATCT, Class C, X52915, M. musculus gene for H-2D(q) antigen, partial 3, c
CCATCT, Class C, V00751, Mouse gene H-2Ld coding for a transplantation anti
CCATCT, Class C, X52916, M. musculus H-2L(q) gene for H-2L(q) antigen. 3, p
CCATCT, Class C, U06244, Mus musculus interferon alpha/beta receptor (IFNAR
CCATCC, Class C, X64716, M. musculus NKR-Pi 2 gene for natural killer cell r
16    .8938%    GGCTTCGGTCT (SEQ ID NO:164)              2750136
Noted Tags = 0    Collected Tags = 0
14    .7821%    AGGTCGGGTGG (SEQ ID NO:165)              711355
Noted Tags = 1    Collected Tags = 0
13    .7262%    CACAAACGGTA (SEQ ID NO:166)              1114541
Noted Tags = 0    Collected Tags = 0
13    .7262%    TGGGTTGTCTA (SEQ ID NO:167)              3849949
Noted Tags = 1    Collected Tags = 1
AAAATA, Class A, X06407, Mouse mRNA for 21 kd polypeptide under translation
12    .6703%    CGCCGCCGGCT (SEQ ID NO:168)              1664424
Noted Tags = 1    Collected Tags = 0
12    .6703%    CTGCTCAGGCT (SEQ TD NO:169)              1995944
Noted Tags = 1    Collected Tags = 1
TAGGAG, Class A, M13806, Mouse keratin (epidermal) type I mRNA, clone pkScc
12    .6703%    GCTGGCCCTTC (SEQ ID NO:170)              2598270
Noted Tags = 0    Collected Tags = 0
11    .6145%    AGGCAGACAGT (SEQ ID NO:171)              673868
Noted Tags = 2    Collected Tags = 2
TGCTGT, Class A, X13661, Mouse mRNA for elongation factor 1-alpha (EF 1-alp
TGCTGT, Class A, M22432, Mus musculus protein synthesis elongation factor T
11    .6145%    TTGGCTGCCCA (SEQ ID NO:172)              4103765
Noted Tags = 1    Collected Tags = 1
GGATGT, Class C, Y08307, M. musculus mitochondrial mRNA for ribosomal protei
10    .5586%    GCCCGGGAATA (SEQ ID NO:173)              2451981
Noted Tags = 1    Collected Tags = 1

TABLE 13-continued

SAGE Analysis of MRL Mice Five Days After Wounding

```
AATTCA, Class A, J05277, Mouse hexokinase mRNA, complete cds.
   9    .5027%    AGAGCGAAGTG (SEQ ID NO:174)            563247
Noted Tags = 1    Collected Tags = 1
GCGGAA, Class A, U93862, Mus musculus ribosomal protein L41 mRNA, complete
   9    .5027%    CAGAACCCACG (SEQ ID NO:175)           1180999
Noted Tags = 2    Collected Tags = 2
ACAGTA, Class C, M76762, Mus musculus ribosomal protein (Ke-3) gene, exons
ACAGTA, Class A, M76763, Mus musculus ribosomal protein (Ke-3) mRNA, comple
   9    .5027%    CATCGCCAGTG (SEQ ID NO:176)           1271087
Noted Tags = 3    Collected Tags = 2
GGCAAA, Class A, M12414, Mouse apolipoprotein E mRNA, complete cds.
GGCAAA, Class A, M73490, Mus musculus apolipoprotein E mRNA, 3' end.
   9    .5027%    CCCCAGCCAGT (SEQ ID NO:177)           1395020
Noted Tags = 2    Collected Tags = 1
GCCTAC, Class A, X76772, M. musculus mRNA for ribosomal protein S3.
   8    .4469%    AGCAGTCCCCT (SEQ ID NO:178)            601432
Noted Tags = 4    Collected Tags = 0
   8    .4469%    CAAACTCTCAC (SEQ ID NO:179)           1056210
Noted Tags = 2    Collected Tags = 2
AGCGAT, Class A, X04017, Mouse mRNA for cysteine-rich glycoprotein SPARC.
AGCGAT, Class C, M20692, Mouse osteonectin (Sparc) gene, exon 10.
   8    .4469%    CTAATAAAGCC (SEQ ID NO:180)           1847334
Noted Tags = 3    Collected Tags = 2
ACTGTG, Class A, X65922, M. musculus fau mRNA.
ACTGTG, Class A, D26610, Mouse mRNA for monoclonal nonspecific suppressor f
   8    .4469%    GGCAAGCCCCA (SEQ ID NO:181)           2689365
Noted Tags = 2    Collected Tags = 1
GCGTCT, Class A, U12403, Mus musculus Csa-19 mRNA, complete cds.
   7    .391%     CAAGGTGACAG (SEQ ID NO:182)           1093139
Noted Tags = 3    Collected Tags = 3
GCCGCT, Class A, M20632, Mouse LLReP3 protein mRNA from a repetitive elemen
GCCGCT, Class C, M20633, Mouse LLRep3 protein pseudogene from a repetitive
GCCGCT, Class C, M20634, Mouse LLRep3 protein pseudogene from a repetitive
   7    .391%     CCAGAACAGAC (SEQ ID NO:183)           1343778
Noted Tags = 3    Collected Tags = 0
   7    .391%     CTGAACATCTC (SEQ ID NO:184)           1967326
Noted Tags = 1    Collected Tags = 1
CCCCTT, Class A, X15267, Mouse mRNA for acidic ribosomal phosphoprotein Po
   7    .391%     GCCTTTATGAG (SEQ ID NO:185)           2489571
Noted Tags = 2    Collected Tags = 1
AAGAAA, Class A, X60289, M. musculus mRNA for ribosomal protein S24.
   7    .391%     GGAAGCCACTT (SEQ ID NO:186)           2630944
Noted Tags = 0    Collected Tags = 0
   7    .391%     GTGAACGTGCC (SEQ ID NO:187)           3016422
Noted Tags = 0    Collected Tags = 0
   7    .391%     GTGGGCGTGTA (SEQ ID NO:188)           3057389
Noted Tags = 1    Collected Tags = 1
CAACGG, Class A, M33330, Mouse insulinoma (rig) mRNA, complete cds.
   6    .3351%    AACACCAAGCT (SEQ ID NO:189)             70696
Noted Tags = 2    Collected Tags = 2
GTCCCT, Class A, X74784, M. musculus mk2e mRNA.
GTCCCT, Class A, M24151, Mouse keratin 70 kd type II mRNA, 3' end.
   6    .3351%    CACCACCACAG (SEQ ID NO:190)           1131795
Noted Tags = 1    Collected Tags = 1
GATCAA, Class A, X05021, Murine mRNA with homology to yeast L29 ribosomal p
   6    .3351%    CACCACCGTTG (SEQ ID NO:191)           1131967
Noted Tags = 1    Collected Tags = 1
CCTTCA, Class C, M21460, Mouse surfeit locus surfeit 3 protein gene, exon 6
   6    .3351%    CACGCTCCCGG (SEQ ID NO:192)           1154395
Noted Tags = 0    Collected Tags = 0
   6    .3351%    CCCGTGTGCTC (SEQ ID NO:193)           1424286
Noted Tags = 0    Collected Tags = 0
   6    .3351%    CCTTGCTCAAT (SEQ ID NO:194)           1566532
Noted Tags = 2    Collected Tags = 1
TAAAA, Class A, M59470, Mouse cystatin C mRNA, complete cds.
   6    .3351%    CTGCTATCCGA (SEQ ID NO:195)           1995609
Noted Tags = 1    Collected Tags = 1
GAGAAT, Class A, X83590, M. musculus mRNA for ribosomal protein LS, 3' end.
   6    .3351%    GAACATTGCAC (SEQ ID NO:196)           2117522
Noted Tags = 3    Collected Tags = 2
CACACG, Class A, X12697, Mouse p2-4 mRNA for SPARC/osteonectin (SPARC = sec
CACACG, Class C, M20691, Mouse osteonectin (Sparc) gene, exon 9.
   6    .3351%    GGATTTGGCTT (SEQ ID NO:197)           2686624
Noted Tags = 0    Collected Tags = 0
   6    .3351%    GGGAAGGCGGC (SEQ ID NO:198)           2755178
Noted Tags = 2    Collected Tags = 1
ACGTCT, Class A, M88335, M. musculus mRNA sequence.
```

TABLE 13-continued

SAGE Analysis of MRL Mice Five Days After Wounding

```
    6     .3351%    GTCTGCTGATG (SEQ ID NO:199)          3008399
Noted Tags = 2   Collected Tags = 2
GCCAGA, Class A, X75313, M. musculus (C57BL/6) GB-like mRNA.
GCCAGA, Class A, D29802, Mouse mRNA for G protein beta subunit homologue, c
    6     .3351%    TCAGGCTGCCT (SEQ ID NO:200)          3450776
Noted Tags = 7   Collected Tags = 6
TCATCT, Class A, X12812, Murine mRNA for macrophage ferritin heavy subunit.
TCATCT, Class C, X52561, Mouse gene for ferritin H subunit.
TCATCT, Class A, J03941, Mouse ferritin heavy chain (MFH) lnRNA, complete cd
TTATCT, Class A, M24509, Mouse ferritin heavy chain, complete cds.
TTATCC, Class C, M73678, Mus musculus (clone PMHFY9) ferritin H pseudogene.
TTATCT, Class C, M73679, Mus musculus (clone pMHFY1) ferritin H pseudogene.
    6     .3351%    TGGATCCTGAG (SEQ ID NO:201)          3814883
Noted Tags = 21  Collected Tags = 4
AACTTC, Class C, V00742, Fragment of the mouse gene for epsilon-globin Y3
AACTTC, Class A, M19236, Mouse beta-globin gene.
AACTTC, Class C, J00414, Mouse beta-globin epsilon y3 gene, exon 2.
AACTTC, Class C, M10688, Mouse beta-globin gene with intron boundary.
    5     .2793%    CGCTGGTTCCA (SEQ ID NO:202)          1698773
Noted Tags = 2   Collected Tags = 0
    5     .2793%    CTCCTGGACAC (SEQ ID NO:203)          1931794
Noted Tags = 1   Collected Tags = 1
CTGGGA, Class A, J04953, Mouse gelsolin gene, complete cds.
    5     .2793%    TATGTCAAGCT (SEQ ID NO:204)          3388456
Noted Tags = 1   Collected Tags = 1
GGTGGA, Class A, X15962, Mouse mRNA for ribosomal protein 512.
    5     .2793%    TCGTGATTGTG (SEQ TD NO:205)          3597295
Noted Tags = 3   Collected Tags = 3
CAGAAT, Class A, U52822, Mus musculus ornithine decarboxylase antizyme mRNA
CAGAAT, Class C, U52823, Mus musculus ornithine decarboxylase antizyme gene
CAGAAT, Class C, U84291, Mus musculus ornithine decarboxylase antizyme gene
    5     .2793%    TTCAGTGGACC (SEQ ID NO:206)          4009606
Noted Tags = 0   Collected Tags = 0
    4     .2234%    AAGAGGCAAGA (SEQ ID NO:207)           141577
Noted Tags = 0   Collected Tags = 0
    4     .2234%    ATACTGACATT (SEQ XD NO:208)           817232
Noted Tags = 4   Collected Tags = 0
    4     .2234%    CAAGTGGAAAA (SEQ ID NO:209)          1096193
Noted Tags = 0   Collected Tags = 0
    4     .2234%    CCCAATGGCCC (SEQ ID NO:210)          1379990
Noted Tags = 3   Collected Tags = 3
AATAAA, Class A, X65582, M. musculus mRNA for alpha-2 collagen VI.
AATAAA, Class A, X62332, M. musculus mRNA for alpha-2 collagen type VI, subu
AATAAA, Class A, Z18272, Mus musculus collagen alpha 2 chain type VI.
    4     .2234%    CCTACCAAGAC (SEQ ID NO:211)          1512482
Noted Tags = 0   Collected Tags = 0
    4     .2234%    GATGACACCAG (SEQ ID NO:212)          2327635
Noted Tags = 1   Collected Tags = 1
CCGCTC, Class A, U11248, Mus musculus C57BL/6J ribosomal protein 528 mRNA,
    4     .2234%    GATTCCGTGAG (SEQ ID NO:213)          2348771
Noted Tags = 0   Collected Tags = 0
    4     .2234%    GCAGAGTGCGC (SEQ ID NO:214)          2395034
Noted Tags = 2   Collected Tags = 1
CTGCTG, Class A, Y00348, Mouse mRNA for ribosomal protein S6.
    4     .2234%    GCCAAGTGGAG (SEQ ID NO:215)          2427811
Noted Tags = 5   Collected Tags = 1
TTCCCA, Class A, M76131, Mouse elongation factor 2 (ef-2) mRNA, 3' end.
    4     .2234%    GCGGCGGATGG (SEQ ID NO:216)          2529851
Noted Tags = 6   Collected Tags = 5
AGACTT, Class C, A27894, Coding sequence for GBP.
AGACTT, Class A, X53067, Mouse mRNA for 14KDa lectin.
AGACTT, Class A, X15986, Mouse 3' mRNA for beta-galactoside specific lectin
AGACTT, Class A, X66532, M. musculus mRNA for L14 lectin.
AGACTT, Class A, M57470, Murine beta-galactoside binding protein mRNA, comp
    4     .2234%    GTGGAGGCGCC (SEQ ID NO:217)          3050086
Noted Tags = 0   Collected Tags = 0
    4     .2234%    TGCACAGTGCT (SEQ TD NO:218)          3740392
Noted Tags = 5   Collected Tags = 5
GAGCAA, Class A, X05835, Mouse mRNA for placental calcium-binding protein.
GAGCAA, Class A, X16190, Mouse mts1 gene.
GAGCAA, Class A, Z36947, Murine retrovirus RNA containing parts of mts1 of
GAGCAA, Class A, D00208, Mus musculus mRNA for pEL98 protein, complete cds.
    4     .2234%    TGGATCAGTCT (SEQ ID NO:219)          3814584
Noted Tags = 1   Collected Tags = 1
TTAAAA, Class A, M62952, Mus musculus ribosomal protein L19, complete cds.
    4     .2234%    TGGCTCGGTCA (SEQ ID NO:220)          3831477
Noted Tags = 6   Collected Tags = 3
```

TABLE 13-continued

SAGE Analysis of MRL Mice Five Days After Wounding

CTTGGG, Class A, X13055, Murine mRNA for cytoplasmic gamma-actin.
CTTGGG, Class C, X13056, Murine gamma-118-actin pseudogene.
CTTGGG, Class A, M21495, Mouse cytoskeletal gamma-actin mRNA, complete cds.
    4    .2234%    TGTGCCAAGTG (SEQ ID NO:221)    3904559
Noted Tags = 0  Collected Tags = 0
    4    .2234%    TTCTTTGGTGA (SEQ ID NO:222)    4062905
Noted Tags = 1  Collected Tags = 0
    3    .1675%    AGTGAGGAAGA (SEQ ID NO:223)    756233
Noted Tags = 1  Collected Tags = 0
    3    .1675%    CACCTTGGTGC (SEQ ID NO:224)    1146554
Noted Tags = 0  Collected Tags = 0
    3    .1675%    CCCTGAGTCCA (SEQ ID NO:225)    1434325
Noted Tags = 2  Collected Tags = 2
CCCCGG, Class A, X03672, Mouse cytoskeletal mRNA for beta-actin.
CCCCGG, Class A, J04181, Mouse A-X actin mRNA, complete cds.
    3    .1675%    CTACCACTCAA (SEQ ID NO:226)    1855953
Noted Tags = 0  Collected Tags = 0
    3    .1675%    CTGAGAGAGAA (SEQ ID NO:227)    1974817
Noted Tags = 0  Collected Tags = 0
    3    .1675%    CTGTAGACTGC (SEQ ID NO:228)    2017402
Noted Tags = 0  Collected Tags = 0
    3    .1675%    CTGTAGGTGAT (SEQ ID NO:229)    2018020
Noted Tags = 0  Collected Tags = 0
    3    .1675%    CTTGACACACA (SEQ ID NO:230)    2065477
Noted Tags = 0  Collected Tags = 0
    3    .1675%    GAGTCTCCCTG (SEQ ID NO:231)    2284895
Noted Tags = 2  Collected Tags = 2
GATTGT, Class C, X59747, Mouse Sm B gene for Sm B protein of U snRNP's, exo
GATTGT, Class A, M58761, Mouse Sm-B protein gene, complete cds.
    3    .1675%    GATGTGGCTGC (SEQ TD NO:232)    2341498
Noted Tags = 0  Collected Tags = 0
    3    .1675%    GCCGCTAGGCC (SEQ ID NO:233)    2464934
Noted Tags = 0  Collected Tags = 0
    3    .1675%    GCCTGTGGCCT (SEQ ID NO:234)    2485912
Noted Tags = 0  Collected Tags = 0
    3    .1675%    GCGCCCTCCCC (SEQ ID NO:235)    2512726
Noted Tags = 1  Collected Tags = 1
TTGTCC, Class A, U88322, Mus musculus beta chemokine Exodus-2 mRNA, complet
    3    .1675%    GGGGGCCCAGG (SEQ ID NO:236)    2794827
Noted Tags = 1  Collected Tags = 1
TGTAGA, Class C, X03059, Mouse germline gene for T-cell receptor J-alpha 65
    3    .1675%    GTGTGGGCACT (SEQ ID NO:237)    3074632
Noted Tags = 1  Collected Tags = 1
GGATTT, Class A, X93035, M. musculus mRNA for BRP39 protein.
    3    .1675%    GTGTTAACCAG (SEQ ID NO:238)    3076179
Noted Tags = 0  Collected Tags = 0
    3    .1675%    TAAAGAGGCCG (SEQ ID NO:239)    3154583
Noted Tags = 1  Collected Tags = 1
TTTTGT, Class A, U67770, Mus musculus: ribosomal protein S26 (RPS26) mRNA, c
    3    .1675%    TGCTTATGATG (SEQ ID NO:240)    3797903
Noted Tags = 0  Collected Tags = 0
    3    .1675%    TGGTGACAAAA (SEQ ID NO:241)    3858689
Noted Tags = 0  Collected Tags = 0
    3    .1675%    TGTCAGTCTGT (SEQ ID NO:242)    3885948
Noted Tags = 1  Collected Tags = 1
TTAACC, Class C, M21050, Mouse lysozyme M gene, exon 4.
    3    .1675%    TTCAGCTCGAG (SEQ ID NO:243)    4007779
Noted Tags = 0  Collected Tags = 0
    2    .1117%    AACAATTTGGG (SEQ ID NO:244)    69611
Noted Tags = 0  Collected Tags = 0
    2    .1117%    AACAGGTTCAA (SEQ ID NO:245)    76753
Noted Tags = 0  Collected Tags = 0
    2    .1117%    AAGCGCCTCAC (SEQ ID NO:246)    157138
Noted Tags = 0  Collected Tags = 0
    2    .1117%    AAGGAAATGGG (SEQ ID NO:247)    164075
Noted Tags = 0  Collected Tags = 0
    2    .1117%    AAGGTCTGCCT (SEQ ID NO:248)    178072
Noted Tags = 1  Collected Tags = 1
GAAAAC, Class A, D87896, Mus inusculus phgpx mRNA for phospholipid hydropero
    2    .1117%    AAGGTGGAAGA (SEQ ID NO:249)    178697
Noted Tags = 0  Collected Tags = 0
    2    .1117%    ACAGTTCCAGA (SEQ ID NO:250)    310601
Noted Tags = 3  Collected Tags = 3
AGTGAT, Class A, AF0234, Mus musculus HS1-associating protein (mHAX-1s) mRN
AGTGAT, Class A, AF0234, Mus musculus HS-1 associating protein HAX-1L (mHAX
AGTGAT, Class A, X81444, M. musculus SIG-111 mRNA.
    2    .1117%    ACCCTCCTCCC (SEQ ID NO:251)    357846

TABLE 13-continued

SAGE Analysis of MRL Mice Five Days After Wounding

```
Noted Tags = 3    Collected Tags = 2
CCCGCT, Class C, K01365, Mouse 18S-5, 8S-28S rRNA gene internal transcribed
CCCGCT, Class C, J00623, Mouse 18S, 5.8S, 28S rRNA gene cluster (clone pMEB
  2      .1117%     AGAGGAAGCTG (SEQ ID NO:252)              565407
Noted Tags = 0    Collected Tags = 0
  2      .1117%     AGCAGGGATCC (SEQ ID NO:253)              600630
Noted Tags = 1    Collected Tags = 1
CCGTGC, Class A, X97490, M. musculus mRNA for PNG protein.
  2      .1117%     AGGAAGGCGGC (SEQ ID NO:254)              658026
Noted Tags = 0    Collected Tags = 0
```

TABLE 14

Accession Numbers for Wound Healing Genes

| | | |
|---|---|---|
| X60671 | Ezrin; Villin 2; NF-2 (merlin) related filament/plasma membrane associated protein | A1f |
| M26391 | Rb; pp105; Retinoblastoma suseptibility-associated protein (tumor suppressor gene; cell cycle regulator) | A1m |
| U52945 | TSG101 tumor suseptibility protein | A1n |
| U54705 | Tumor suppressor maspin | A2a |
| D14340 | ZO-1; Tight junction protein; discs-large family member, partially homologous to a dig-A tumor suppressor in Drosophila | A2d |
| X51983 | c-ErbA oncogene; thyroid hormone receptor | A2g |
| J04115 | c-Jun proto-oncogene (transcription factor AP-1 component) | A2i |
| X83974 | RNA polymercase I termination factor TTF-1 | A2j |
| X01023 | c-myc proto-oncogene protein | A2l |
| U51866 | Casein kinase II (alpha subunit) | A3n |
| M13945 | Plm-1 proto-oncogene | A4a |
| X68932 | c-Fms proto-oncogene (macrophage colony stimulating factor 1 (CSF-1) receptor) | A4b |
| M84607 | PDGFRa; platelet-derived growth factor alpha-receptor | A4e |
| U14173 | Sid proto-oncogene | A4g |
| U18342 | Sky proto-oncogene (Tyro3; Rse; Dtk) | A4h |
| Z50013 | H-ras proto-oncogene: transforming G-protein | A5c |
| X13664 | N-ras proto-oncogene; transforming G-protein | A5e |
| X81580 | IGFBP-2; insulin-like growth factor binding protein 2; autocrine and/or paracrine | A5m |
| X66032 | Cyclin B2 (G2/M-specific) | A6d |
| M83749 | Cyclin D2 (G1/S-specific) | A6g |
| Z37110 | Cyclin G (G2/M-specific) | A6k |
| U19596 | p18lnk4; cdk4 and cdk6 inhibitor | A7c |
| X58135 | Prothymosin alpha | A7m |
| M36829 | HSP84; heat shock 84kD protein | B1a |
| M36830 | HSP86; heat shock 86kD protein | B1d |
| D78645 | Glucose regulated protein, 78kD; Grp78 | B1m |
| U34259 | Golgi 4-transmembrane spanning transporter; MTP | B2d |
| L03529 | Cl2r; coagulation factor II (thrombin) receptor | B2j |
| M83336 | Interleukin-6 receptor beta chain; membrane glycoprotein gp130 | B3c |
| U36277 | I-kappa B alpha chain | B3m |
| U06924 | Stat1; signal transducer and activator of transcription | B4d |
| L47850 | Stat6; signal transducer and activator of transcription 6: IL-4 Stat; STA6 | B4g |
| S72408 | Crk adaptor protein | B4m |
| U28423 | Inhibitor of the RNA-activated protein kinase, 58-kDa | B5l |
| U10871 | MAPK; MAP kinase; p38 | B5m |
| L02526 | MAPKK1; MAP kinase kinase 3 (dual specificity) (MKK1) | B6a |
| D11091 | PKC-theta PI-K p58, | B6h |
| M60851 | PDGF signaling pathway member | B6k |
| X95403 | Rab2 ras-related protein | B7b |
| U57311 | 14-3-3 protein eta | B7g |
| M21065 | IRF1; interferon regulatory factor 1 | B7k |
| X99063 | Zyxin; LIM domain protein; alpha-actinin binding protein | B7n |
| U17162 | BAG-1; bcj-2 binding protein with anti-cell death activity | C1e |
| U13705 | Glutathione peroxidase (plasma protein); selenoprotein | C1l |
| X76341 | Glutathione reductase | C1m |
| J03762 | Glutathione S-transferase (microsomal) | C2a |
| J04696 | Glutathione S-transferase Mu 1 | C2b |
| M94335 | c-Akt proto-oncogene, Rac-alpha: proteine kinase B (PKB) | C2k |
| U97076 | FLIP-L; apoptosis inhibitor: FLICE-like inhibitory protein | C3h |
| L28177 | Gadd45; growth arrest and DNA-damage-inducible protein | C3j |
| X68193 | Nm23-M2: nucleoside diphosphate kinase B; metastasis-reducing protein; c-myc-related transcription factor | C4c |
| D83966 | Protein tyrosine phosphatase | C4g |
| U25995 | RIP cell death protein; Fas/APO-1 (CD95) interactor, contains death domain | C4j |
| U25844 | SP13; serpin; similar to human proteinase inhibitor 6 (placental thrombin inhibitor) serine proteinase inhibitor | C4l |
| M59378 | Tumor necrosis factor receptor 1; TNFR-1 | D5d |

TABLE 14-continued

Accession Numbers for Wound Healing Genes

| | | |
|---|---|---|
| X96618 | PA6 stromal protein; RAG1 gene activator | C6a |
| X92410 | MHR238; Rad23 UV excision repair protein homologue; xeroderma pigmentosum group C (XPC) repair complementing protein | C6j |
| U17698 | Abiphilin-1 (abi-1) similar to HOXD3 | D1a |
| L12721 | Adipocyte differentiation-associated protein | D1c |
| L36435 | Basic domain/leucine zipper transcription factor | D1e |
| M68566 | Butyrate response factor 1 | D1i |
| U36340 | CACCC Box- binding protein BKLF | D1j |
| X72310 | DP-1 (DRTF-polipeptide 1) cell cycle regulatory transcription factor | D2g |
| J04103 | Ets-2 transcription factor | D3b |
| X55123 | GATA-3 transcription factor | D3f |
| U20344 | Gut-specific Kruppel-like factor GKLF | D3i |
| X53478 | HMG-14 non histone chromosomal protein | D3m |
| J03168 | Interferon regulatory factor 2 (IRF 2) | D4i |
| D90176 | NF-1B protein (transcription factor) | D5f |
| U20532 | Nuclear factor related to P45 NF-E2 | D5h |
| U53228 | Nuclear hormone receptor ROR-ALPHA-1 | D5i |
| U41628 | Split hand/foot gene | D5m |
| M35523 | Retinoic acid binding protein II cellular (CRABP-II) | D6e |
| U09419 | Retinoid X receptor interacting protein (RIP 15) | D6g |
| X61753 | Transcription factor 1 for heat shock gene | D6i |
| U51037 | Transcription factor CTCF (11 zinc fingers) | D6j |
| X91763 | Transcription factor SEF2 | D7e |
| X57621 | YB1 DNA binding protein | D7j |
| L13968 | YY1 (UCRBP) transcriptional factor | D7k |
| Z31663 | Activin type I receptor | E1a |
| U58819 | C-C chemokine receptor (Monocyte chemoattractant protein 1 receptor (MCP-1RA) | E1d |
| M98547 | Growth factor receptor | E2f |
| X13358 | Glucocorticoid receptor form A | E3m |
| L06039 | CD31 (Platelet endothelial cell adhesion molecule 1) | E6d |
| M27129 | CD44 antigen | E6e |
| U43512 | Dystroglycan 1 | E6m |
| X04648 | Glutamate receptor channel subunit gamma | E6n |
| X69902 | Integrin alpha 6 | E7d |
| Y00769 | Integrin beta | E7g |
| J02870 | Laminin receptor 1 | E7j |
| L24755 | Bone morphogenetic protein 1 | F1b |
| X81584 | Insulin-like growth factor binding protein-6 (IGFBP 6) | F2i |
| X81581 | Insulin-like growth factor binding protein-3 (IGFBP-3) | F2k |
| X81582 | Insulin-like growth factor binding protein-4 (IGFBP-4) | F2l |
| X81583 | Insulin-like growth factor binding protein-5 (IGFBP-5) | F2m |
| X04480 | Insulin-like growth factor-1A | F3a |
| X12531 | Macrophage inflammatory protein | F3e |
| U80530 | Mad related protein 2 (MADR2) | F3h |
| M14220 | Neuroleukin | F3m |
| U22516 | Placental ribonuclease inhibitor (Anglogenin) | F4a |
| M13177 | Transforming growth factor beta | F4f |
| X57413 | Transforming growth factor beta 2 | F4g |
| M13806 | Cytoskeletal epidermal keratin (14 human) | F5h |
| M10937 | Epidermal keratin (1 human) | F5k |
| U04443 | Non-muscle myosin light chain 3 | F6b |
| X51438 | Vimentin | F6d |
| J04946 | Anglotensin-converting enzyme (ACE) (clone ACE 5.) | F6f |
| M14222 | Cathepsin B | F6g |
| X63337 | Cathepsin D | F6h |
| X06086 | Cathepsin L | F6j |
| M12302 | Cytotoxic T lymphocyte-specific serine protease CCP I gene (CTLA-1) | F6m |
| M55617 | Mast cell protease (MMCP)-4 | F7b |
| X83536 | Membrane type matrix metalloproteinase | F7c |
| X16490 | Plasminogen activator inhibitor-2 | F7i |
| J05609 | Serine protease inhibitor homolog J6 | F7l |
| L19622 | TIMP-3 tissue inhibitor of metalloproteinases-3 | F7n |

TABLE 15

Differentially Expressed Genes in Healer and Non-Healer Dendritic Cells

| GENE NAME | Array location | 50% > |
|---|---|---|
| Elk-1 ets related proto-oncogene | A3a | MRL > |
| Pim-1 proto-oncogene | A4a | MRL > |
| cyclin A | A6a | MRL > |
| BRCA 1 | A1b | MRL > |
| VHL | A2b | MRL > |
| Fli-1 ets related proto-oncogene | A3b | MRL > |
| BRCA2 | A1c | MRL > |
| Fos-B | A3c | MRL > |

TABLE 15-continued

Differentially Expressed Genes in Healer and Non-Healer Dendritic Cells

| GENE NAME | Array location | 50% > |
|---|---|---|
| Dcc; netrin receptor | A1d | MRL > |
| Fra-2 | A3d | MRL > |
| EB1 APC binding protein | A1e | MRL > |
| GII oncogene | A3e | MRL > |
| PDGFRa | A4e | MRL > |
| N-ras | A5e | MRL > |
| ezrin | A1f | B6 > |
| B-myb proto-oncogene | A2f | MRL > |
| Jun-B | A3f | MRL > |
| Ret proto-oncogene | A4f | MRL > |
| Shc transforming adaptor protein | A5f | MRL > |
| Madr1 | A1g | MRL > |
| c-ErbA oncogene | A2g | MRL > |
| Ski proto-oncogene | A4g | MRL > |
| CSF-1 | A5g | MRL > |
| Mdm2 | A1h | MRL > |
| c-Fos proto-oncogene | A2h | MRL > |
| Sky proto-oncogene | A4h | MRL > |
| Nf2; merlin | A1i | MRL > |
| c-Jun proto-oncogene | A2i | MRL > |
| p107; RBL1 | A1j | MRL > |
| p130 | A1k | MRL > |
| p53; tumor suppressor | A1l | MRL > |
| Fyn proto-oncogene | B5a | B6 > |
| Mapkk1 | B6a | B6 > |
| Gem | B7a | B6 > |
| Hck tyrosine protein kinase | B5b | B6 > |
| Mapkk3 | B6b | B6 > |
| Rab-2 ras related protein | B7b | B6 > |
| B7-2; T lymphocyte activation antigen CD86 | B2g | MRL > |
| Mapkapk-2 | B5n | B6 > |
| zyxin | B7n | B6 > |
| Craf-1 | C3c | B6 > |
| Nm23-M2 | C4c | B6 > |
| DAD-1 | C3d | B6 > |
| Nur77 early response protein | C4d | B6 > |
| Faf1 | C3e | B6 > |
| p55cdc | C4e | B6 > |
| Fas1 receptor | C3f | B6 > |
| PD-1 possible cell death inducer | C4f | B6 > |
| Adenosine A2M2 receptor | C2g | B6 > |
| Fas1 | C3g | B6 > |
| protein tyrosine kphosphatase | C4g | B6 > |
| Adenosine A3 receptor | C2h | B6 > |
| MHR23A | C6l | B6 > |
| Blk | C2j | B6 > |
| c-Akt proto-oncogene | C2k | B6 > |
| Glutathione peroxidase | C1l | B6 > |
| iNOS1 | C3m | B6 > |
| interleukin 1 receptor | C3n | B6 > |
| stromolysin 3 | C4n | B6 > |
| activating transcription factor 4 | D1b | MRL > |
| Pax6 | D6b | B6 > |
| SRY-box containing gene 4 | D7b | B6 > |
| adipocyte differentiation-associated protein | D1c | MRL > |
| transcription factor RelB | D7c | B6 > |
| AT motif-binding factor ATBF1 | D1d | MRL > |
| transcription factor NURR-1 | D1g | MRL > |
| nuclear factor related to P45NF-E2 | D5h | B6 > |
| Butyrate response factor 1 | D1i | MRL > |
| CCAAT-binding transcription factor | D1k | MRL > |
| IRF-2 | D4l | B6 > |
| split hand/foot gene | D5m | B6 > |
| Zinc finger transcription factor RU49 | D7m | B6 > |
| SOX-3 | D5n | B6 > |
| Zinc finger X-chromosomal protein ZFX | D7n | B6 > |
| activin type 1 receptor | E1a | B6 > |
| orphan receptor | E1b | B6 > |
| G-protein coupled receptor | E5c | B6 > |
| MCP-1RA | E1d | B6 > |
| CD31 | E6d | B6 > |
| CD4 receptor | E1e | B6 > |
| GABA-A transporter 1 | E5e | B6 > |
| CD44 | E6e | B6 > |
| CD14 | E6h | B6 > |
| CD22 | E6i | B6 > |
| desmocollin 2 | E6l | B6 > |
| interferon-gamma receptor | E2m | B6 > |
| dystroglycan 1 | E6m | B6 > |
| ERBB-3 receptor | E1n | B6 > |
| interleukin-1 receptor type II | E2n | B6 > |
| growth hormone receptor | E3n | B6 > |
| VLA-3 alpha subunit | E7n | B6 > |
| angiogenin | F4a | B6 > |
| interleukin 15 | F5a | B6 > |
| KIF3B | F6a | B6 > |
| non-muscle myosin light chain 3 | F6b | B6 > |
| prepro-endothelin-3 | F4c | B6 > |
| TGF-beta 2 | F4g | B6 > |
| TNF-beta | F4h | B6 > |
| plasminogen activator inhibitor | F7h | B6 > |
| IGFBP-6 | F2i | B6 > |
| uromodulin | F4i | B6 > |
| cathepsin H | F6i | B6 > |
| plasminogen activator inhibitor 2 | F7i | B6 > |
| vascular endothelial growth factor | F4j | B6 > |
| cytoskeletal epidermal keratin 19 | F5j | B6 > |
| cathepsin L | F6j | B6 > |
| Spi-2 | F7j | B6 > |
| interleukin-1 beta | F4k | B6 > |
| collagenase type IV | F6k | B6 > |
| serine protease inhibitor 2.4 | F7k | B6 > |
| follistatin | F1l | B6 > |
| IGFBP-4 | F2l | B6 > |
| interleukin 10 | F4l | B6 > |
| cytotoxic cell protease (B10) | F6l | B6 > |
| serine protease inhibitor homolog J6 | F7l | B6 > |
| M/G | F1m | B6 > |
| neuroleukin | F3m | B6 > |
| interleukin 11 | F4m | B6 > |
| KIF1A | F5m | B6 > |
| CTLA1 | F6m | B6 > |
| TIMP-2 | F7m | B6 > |
| glial cell derived neuronal growth factor | F1n | B6 > |
| IGF-2 | F2n | B6 > |
| oncostatin M | F3n | B6 > |
| interleukin 12 (p40) beta chain | F4n | B6 > |
| gelatinase B | F6n | B6 > |
| TIMP-3 | F7n | B6 > |

TABLE 16

Segregation of Quantitative Trait Loci in Phenotype Congenic Mice

| Marker | 1-2-3-4-5 | 6-7-8-9-10 | 11-12-13- | 14-15-17 |
|---|---|---|---|---|
| 1–185 (59) | B-B-B-B-B | B-B-B-B-B | B--B--B | B--B--B |
| 1–228 (72) | B-B-B-B-B | B-B-B-B-B | B--B--B | B--B--B |
| 2–329 (45) | B-B-B-B-B | B-B-B-B-B | B--B--B | B--B--B |
| 2–207 (60) | B-B-B-B-B | B-B-B-B-B | B--B--B | B--B--B |
| 2–107 (76) | B-B-B-B-B | B-B-B-B-B | B--B--B | B--B--B |
| 2–113 (103) | B-B-B-B-B | B-B-B-B-B | B--B--B | B--B--B |
| 3–310 (38) | B-B-B-B-B | H-H-H-H-B | B--B--B | B--B--H |
| 4–149 (0) | H-H-H-H-H | H-H-H-H-S | S--S--S | S--S-- |
| 4–236 (12) | | U-H- | | B--B--B |
| 4–151 (29) | H-S-B-U-H | H-B-H-H-H | H--S--S | H--H--B |
| 4–306 (51) | | H-H-H-H-H | H--S--U | S--S--B |
| 4–127 (78) | U-B-U-U-U | U-B-U-B | B--B--B | B--B--B |
| 5–255 (34) | H-U-S-U-S | S-S-H-H-S | H--H--H | S--S--B |
| 5–215 (71) | S-U-S-U-U | U-S-U-S-H | H--S--S | S--S--B |
| 7–228 (19) | H-B-B-U-H | B-B-H-B-H | B--H--B | B--B--B |
| 7–220 (52) | H-S-B-S-B | B-H-B-H-S | B--S--S | H--H--H |
| 7–237 (53) | H-S-B-H-B | B-H-B-H-S | H--S--S | H--H--H |
| 8–211 (49) | B-B-B-B-B | B-B-B-B-B | B--B--B | B--B--B |
| 8–166 | B-B-B-B-B | B-B-B-B-B | B--B--B | B--B--B |
| 9–297 (15) | B-B-B-B-B | B-B-B-B-B | B--B--B | B--B--B |
| 9–207 (33) | B-B-B-B-B | B-B-B-B-B | B--B--B | B--B--B |

TABLE 16-continued

Segregation of Quantitative Trait Loci in Phenotype Congenic Mice

| Marker | 1-2-3-4-5 | 6-7-8-9-10 | 11-12-13- | 14-15-17 |
|---|---|---|---|---|
| 10–106 (17) | B-B-B-B-B | B-B-B-B-B | B--B--B | B--B--B |
| 10–198 (40) | H-H-B-B-B | B-H-H-H-S | H--H--S | H--H--B |
| 10–233 (62) | B-B-B-B-B | B-B-B-B-B | B--B--B | B--B--B |
| 11–74 (0) | B-B-B-B-B | B-B-B-B-B | B--B--B | B--B--B |
| 11–235 (20) | B-B-B-B-B | B-B-B-B-B | B--B--B | B--B--B |
| 11–245 (43) | B-B-B-B-B | B-B-B-B-B | B--B--B | B--B--B |
| 11–48 (77) | B-B-B-B-B | B-B-B-B-B | B--B--B | B--B--B |
| 12–158 (38) | B-B-B-B-B | B-B-B-B-B | B--B--B | B--B--B |
| 12–132 (52) | B-B-B-B-B | B-B-B-B-B | B--B--B | H--H--B |
| 12–233 (52) | B-B-B-B-B | B-B-B-B-B | B--B--B | B--B--B |
| 13–135 (10) | B-B-B-B-B | B-B-B-B-B | H--H--H | B--H--H |
| 13–115 (11) | B-B-B-B-B | B-B-B-B-B | H--H--H | B--H--H |
| 13–116 (13) | B-B-B-B-B | B-B-B-B-B | H--H--H | B--H--H |
| 13–60 (16) | B-B-B-S-H | B-S-S-H-B | H--H--H | B--H--H |
| 13–245 (30) | B-B-B-S-H | B-U-S-H-B | H--H--H | B--H--H |
| 13–139 (32) | H-H-S-H-B | B-S-S-H-H | H--S--H | S--S--H |
| 13–NDSI (32) | H-H-S-H-B | B-S-S-H-H | H--S--H | S--S--H |
| 13–13 (35) | H-H-S-H-B | B-S-S-H-H | H--S--H | S--S--H |
| 13–184 (35) | H-H-S-H-B | B-S-S-H-H | H--S--H | S--S--H |
| 13–122 (36) | H-H-S-U-B | B-S-S-H-B | H--S--H | S--S--H |
| 13–124 (37) | H-H-S-U-B | B-S-S-H-B | H--S--H | S--S--H |
| 13–142 (37) | H-H-S-H-B | B-S-S-H-B | H--S--H | S--S--H |
| 13–26 (38) | H-H-S-H-B | B-S-S-H-B | H--S--H | S--S--U |
| 13–231 (39) | H-H-S-B-B | B-S-U-H-B | H--S--H | S--S--H |
| 13–11 (40) | H-H-S-U-B | B-S-U-H-U | H--S--H | S--S--H |
| 13–254 (40) | H-H-S-H-B | B-S-S-H-B | H--S--H | S--S--H |
| 13–191 (45) | H-H-S-U-B | B-S-S-S-B | H--S--H | S--S--H |
| 13–27 (42) | H-H-S-U-B | B-S-S-S-B | B--H--H | H--B--U |
| 13–144 (48) | H-H-S-H-B | B-S-S-S-B | B--H--H | H--B--B |
| 13–148 (59) | B-B-B-B-B | B-B-B-B-B | B--B--B | B--B--U |
| 13–129 (60) | B-B-B-B-B | B-B-B-B-B | B--B--B | B--B--B |
| 13–260 (65) | B-B-B-B-B | B-B-B-B-B | B--B--B | B--B--B |
| 14–110 (3.5) | B-B-B-B-B | B-B-B-B-B | B--B--B | B--B--B |
| 14–121 (17) | B-B-B-B-B | B-B-B-B-B | B--B--B | B--B--B |
| 15–230 (28) | B-B-B-B-B | B-B-B-B-B | B--B--B | B--B--B |
| 15–189 (49) | B-B-B-B-B | B-B-B-B-B | B--B--B | B--B--B |
| 15–242 (56) | B-B-B-B-B | B-B-B-B-B | B--B--B | B--B--B |
| 15–244 (56) | B-B-B-B-B | B-B-B-B-B | B--B--B | B--B--B |
| 16–32 (2) | B-B-B-B-B | B-B-H-H-B | B--B--B | B--B--B |
| 16–39 (29) | S-H-H-S-H | H-H-S-H-H | B--H--H | H--H--B |
| 18–158 (16) | B-B-B-B-B | B-B-B-B-B | B--B--B | B--B--B |
| 18–123 (31) | B-B-B-B-B | B-B-B-B-B | B--B--B | B--B--B |
| 19–101 (26) | B-B-B-B-B | B-B-B-B-B | B--B--B | B--B--B |

REFERENCES

1. Gross, J. Getting to mammalian wound repair and amphibian limb regeneration: a mechanistic link in the early events. *Wound Repair and Regeneration* 4,190–202, 1996.
2. Stocum, D. L. Tissue restoration: approaches and prospects. *Wound Repair and Regeneration.* 4, 3–15, 1996.
3. Borgens, R. B. Mice regrow the tips of the foretoes. *Science* 217,747–50, 1982.
4. Goss, R. J. Problems of antlerogenesis. *Clin. Orthopaedics* 69,227–38, 1970.
5. Goss, R. J. and Grimes, L. N. Epidermal downgrowths in regenerating rabbit ear holes. *J. Morphology* 146, 533–42, 1975.
6. Fausto, N. Hepatic regeneration. In Hepatology: a textbook in liver disease, 2nd edition (eds. Zakim, D. and Boyer, T. D.), pp. 49–65 Saunders, Philadelphia, 1990.
7. Michalopoulos, G. K. and DeFrances, M. C. Liver Regeneration. *Science* 276, 60–66, 1997.
8. Folkman, J. and Klagsbrun, M. Angiogenic factors. *Science* 235, 442–447,1987.
9. Potten, C. S. and Morris, R. J. Epithelial stem cells in vivo. In Stem Cells. (eds. Lord, B. I. and Dexter, T. M.) pp. 45–62, The Company of Biologists Limited, Cambridge, 1988.
10. Martin, P. Wound Healing—Aiming for perfect skin regeneration. *Science* 276, 75–81, 1997.
11. Spangrude, G. J., Heimfeld, S., Weisman I. L. Purification and characterization of mouse hematopoietic stem cells. *Science* 241, 58–62, 1988.
12. Womom, I. L. and Buchman, S. R. Bone and cartilaginous tissue. In Wound healing: biochemical and clinical aspects. (eds. Cohen, I. K., Diegelmann, R. F. and Lindblad, W. J.) pp.356–83, Saunders, Philadelphia, 1992.
13. Murphy, E. D. and Roths, J. B. Autoimmunity and lymphoproliferation: Induction by mutant gene lpr and acceleration by a male-associated factor in strain BXSB. In Genetic Control of Autoimmune Disease. (eds. Rose, N. R., Bigazzi, P. E., and Warner, N. L).pp. 207–220, Elsevier, N.Y., 1979.
14. Cohen, P. L. and Eisenberg, R. A. Lpr and gld: Single Gene models of Systemic Autoimmunity and Lymphoproliferative disease. *Annu. Rev. Immunol.* 9,243–69,1991.
15. Theofilopoulos, A. N. Immunologic genes in mouse lupus models. In The Molecular Pathology of Autoimmune Diseases. (eds. Bona, C., Siminovitch, K. A., Zanetti, M. and Theofilopoulos, A. N.) pp. 281–316, Harwood Academic Publishers, Langhorne, 1993.
16. Watanabe-Fukunaga, R., Brannan, C., Copeland, N. G., Jenkins, N. A. and Nagata, S. Lymphoproliferation disorder in mice is explained by defects in Fas antigen that mediates apoptosis. *Nature* 356, 314–316, 1992.
17. Watson, M. L., et. al. Genetic analysis of MRL-lpr mice: relationship of the Fas apoptosis gene to disease manifestations and renal disease modifying loci. *J. Exp. Med.* 176, 1645–1656, 1992.
18. Russell, P. S. and Billingham, R. E. Some aspects of the repair process in mammals. *Prog. Surg.* 2,1–72, 1962.
19. Chalkley, D. T. The cellular basis of limb regeneration. In Regeneration in vertebrates. (ed. Thornton, C. S.) pp.34–58, Univ. of Chicago Press, Chicago, 1959.
20. Simon, H-G, Kittappa, R., Khan, P. A., Tsilfidis, C., Liversage, R. A., and Oppenheimer, S. A novel family of T-box genes in urodele amphibian limb development and regeneration: candidate genes in vertebrate forelimb/hindlimb patterning. *Development* 124:1355–1366,1997.
21. Muneoka, K., Fox, W. F., and Bryant, S. V. Cellular contribution from dermis and cartilage to the regenerating limb blastema in axolotls. *Developmental Biology* 116: 256–60,1986.
22. Carrel, A. and Hartmann, A. Cicatrization of wounds. I. The relation between the size of the wound and the rate of its cicatrization. *J. Exp. Med.* 24: 429–450, 1916.
23. Adachi, M., Watanabe-Fukunaga, R. and Nagata, S. Aberrant transcription caused by the insertion of an endogenous retrovirus in an apoptosis gene. *PNAS* 90,1756–1760,1993.
24. Costa, O. and Monier, J. C. Anithistone antibodies detected by microELISA and immunoblotting in mice with lupus-like syndrome (MRL/l, MRL/n, PN, AND NZB strains). *Clin. Immunol. Immunopath.* 40, 276–282,1986.
25. Clark, R. A. F. Wound Repair: Overview and general considerations. In The Molecular and Cellular Biology of Wound Repair. (ed.Clark, R.) pp. 3–35, Plenum Press, New York, 1996.
26. Yamada, K. M. and Clark, R. A. F. Provisional Matrix In The Molecular and Cellular Biology of Wound Repair. (ed.Clark, R.) pp.51–82, Plenum Press, New York, 1996.
27. Stocum, D. L. The urodele limb regeneration blastema. Determination and organization of the morphogenetic field. *Differentiation.* 27,13–28, 1984.
28. Mustoe, T. A., Pierce, G. F., Morishima, C. and Deuel, T. F. Growth factor-induced acceleration of tissue repair through direct and inductive activities in a rabbit dermal ulcer model. *J. Clin. Invest.* 87, 694–703, 1991.
29. Pierce, G. F., et. al. Platelet-derived growth factor (BB homodimer), transforming growth factor-B1, and basic fibroblast growth factor in dermal wound healing: Neovessel and matrix formation and cessation of repair. *Am. J. Pathol.* 140, 1375–1388, 1992.
30. Uhl, E., et al. Basic fibroblast growth factor accelerates wound healing in chronically ischaemic tissue. *Br. J. Surg.* 80, 977–980, 1993.
31. McBrearty, B. A., Desquenne Clark, L., Zhang, X-M, Blankenhorn, E. P., and Heber-Katz,E. Genetic analysis of a mammalian wound healing trait. *Proc. Natl. Acad. Sci. U.S.A.,* in press.
32. Ragsdale, C. W., Gates, P., Hill, D. S. and Brockes, J. P. Delta retinoic acid receptor isoform d1 is distinquished by its exceptional N-terminal sequence and abundance in the limb regeneration blastema. *Mechanisms of Development.* 40,99–112, 1992.
33. White, J. A., Boffa, M. B., Jones, B. and Petkovich, M. A zebrafish retinoic acid expressed in the regenerating caudal fin. *Development.* 120, 1861–1872, 1994.
34. Chernoff, E. A. G. and Stocum, D. Developmental aspects of spinal cord and limb regeneration. *Dev. Growth Diff.* 37,133–47, 1995.
35. Joseph, J., and Dyson, M. (1966) *Brit. J. Surg.* 53, 372–380.
36. Clark, L. D., Clark, R. K., and Heber-Katz, E. (1998) *Clin Immunol Immunopath,* 88, 34–45.
37. Murphy E. D. (1981) in *Immunological defects in laboratory animals Vol.2,* eds. Gershwin, M. E., Merchant, B. (New York and London), pp 143–73.
38. Dietrich, W. F. et al. (1994) *Nature Genetics* 7, 220–245.
39. Manly, K. F. (1993) *Mammalian Genome* 4,303–313.
40. Doerge, R. W., and Churchill, G. A. (1996) Genetics 142, 285–294.
41. Churchill, G. A., and Doerge, R. W. (1994) Genetics 138, 963–971.
42. Wright, S. in Quantitative Genetics (1952) eds. Reeve, E. C. and Waddington, C. H.) (HMSO, London), pp. 5–41.
43. Hartl, D. L. in *Basic Genetics* (1991) (Jones and Bartlett, Boston), pp. 218–220.
44. Lander, E. S., and Krugylak, L. (1995). *Nature Genetics* 11, 241–247.
45. Cheveraud, J. M., and Routman, E. J. (1995) *Genetics* 139, 1455–61.
46. Frankel, W. (1995) *Trends Genet* 11, 471–477.
47. Simon, M I, Strathmann, M P, and Gautum, N. (1991) *Science* 252, 802–808.
48. Bryant, S. V. and Gardinar, D. M. (1997) in *Metamorphosis and regeneration: Keys to tissue Regeneration,* p. 12.
49. Reginelli, A. D., Wang,Y-Q, Sassoon, D., and Muneoka, K. (1995) *Development* 121, 1065–1076.
50. Chuong, C. M., Widelitz, R. B., Ting-Berreth, S., and Jiang., T. X. (1996) *J. Invest. Derm.* 107, 639–646.
51. Ron, D., Reich,R., Chedid, M., Lengel, C., Cohen, O. E., Chan, A. M. Neufeld, G., Miki, T., and Tronick, S. R. (1993) *J. Biol. Chem.* 268, 5388–5394.
52. Percrino, L. T., Lo, D. C., Brockes, J. P. (1994) *Development* 20, 325–333.
53. Sucov, H. M. and Evans, R. M. (1995) *Molecular Neurobiology* 10, 1969–184.
54. Shah, M., et al. (1995) *J. Cell Sci.* 108, 15–17.

What is claimed is:

1. A method of identifying a chromosomal locus containing at least one candidate gene involved in enhanced wound healing, comprising the steps of:
 (a) identifying a first and a second form of a polymorphic DNA microsatellite marker, wherein the first form identifies a first mouse strain and the second form identifies a second mouse strain, wherein the first mouse strain is a healer mouse strain and wherein the second mouse strain is not a healer mouse strain;
 (b) performing a first cross between a mouse of the first mouse strain and a first mouse of the second mouse strain to form $F_1$ mice;
 (c) performing a second cross between (1) a first $F_1$ mouse and (2) a mouse selected from the group consisting of (i) a second $F_1$ mouse, (ii) a second mouse of the second mouse strain, and (iii) a second mouse of the first mouse strain;
 (d) identifying progeny of the second cross that exhibit an enhanced wound healing phenotype and progeny of the second cross that exhibit a non-enhanced wound healing phenotype;
 (e) identifying genotypes of progeny of the second cross, wherein the genotypes are selected from the group consisting of (1) a genotype homozygous for the first form of the polymorphic DNA microsatellite marker, (2) a genotype homozygous for the second form of the polymorphic DNA microsatellite marker, and (3) a genotype heterozygous for the first and second forms of the polymorphic DNA microsatellite marker; and
 (f) performing a statistical analysis to determine whether the first form of the polymorphic DNA microsatellite marker segregates with progeny of the second cross that exhibit the enhanced wound healing phenotype, whereby a chromosomal locus containing at least one candidate gene involved in enhanced wound healing is identified.

2. The method of claim 1 wherein the first mouse strain is an MRL mouse strain.

3. The method of claim 1 wherein the first mouse strain comprises at least one quantitative trait locus selected from the group consisting of the quantitative trait loci shown in Tables 2, 9, and 16, wherein the first mouse strain exhibits an enhanced healing response to a wound compared to a second mouse strain which does not comprise the at least one quantitative trait locus, wherein the first mouse strain is not an MRL mouse strain.

4. The method of claim 1 wherein the second mouse strain is C57BL/6.

5. The method of claim 1 wherein the mouse of the first mouse strain is a female.

6. The method of claim 1 wherein the mouse of the first mouse strain is a male.

7. The method of claim 1 wherein the first $F_1$ mouse is a female.

8. The method of claim 1 wherein the first $F_1$ mouse is a male.

9. The method of claim 1 wherein the first mouse strain is MRL/MpJ.

10. The method of claim 1 wherein the first mouse strain is MRL/lpr.

11. The method of claim 1 wherein the first mouse strain is LG.

12. The method of claim 1 further comprising the steps of:

(g) performing a third cross between (1) a first progeny of a cross between an $F_1$ mouse and a mouse of the first strain that exhibits the non-enhanced wound healing phenotype and (2) a mouse selected from the group consisting of (i) a second progeny of the second cross that exhibits non-enhanced wound healing and (ii) a mouse of the first mouse strain;

(h) identifying genotypes of progeny of the third cross wherein the genotypes are selected from the group consisting of (1) a genotype homozygous for the first form of the polymorphic DNA microsatellite marker, (2) a genotype homozygous for the second form of the polymorphic DNA microsatellite marker; and (3) a genotype heterozygous for the first and second forms of the polymorphic DNA microsatellite marker; and (i) performing a statistical analysis to determine whether the second form of the polymorphic DNA microsatellite marker segregates with progeny of the third cross that exhibit the non-enhanced wound healing phenotype, whereby either the chromosomal locus identified in step (f) is confirmed, the chromosomal locus identified in step (f) is narrowed, or a new chromosomal locus containing at least one candidate gene involved in enhanced wound healing is identified.

13. The method of claim 12 wherein the first mouse strain is an MRL mouse strain.

14. The method of claim 12 wherein the first progeny of the cross between the $F_1$ mouse and the mouse of the first strain is a female.

15. The method of claim 12 wherein the first progeny of the cross between the $F_1$ mouse and the mouse of the first strain is a male.

16. The method of claim 1 further comprising the steps of:

(g) performing a third cross between (1) a first progeny of a cross between an $F_1$ mouse and a mouse of the second strain that exhibits enhanced wound healing and (2) a mouse selected from the group consisting of (i) a second progeny of the second cross that exhibits enhanced wound healing and (ii) a mouse of the second mouse strain;

(h) identifying genotypes of progeny of the third cross, wherein the genotypes are selected from the group consisting of (1) a genotype homozygous for the first form of the polymorphic DNA microsatellite marker, (2) a genotype homozygous for the second form of the polymorphic DNA microsatellite marker, and (3) a genotype heterozygous for the first and second forms of the polymorphic DNA microsatellite marker; and (i) performing a statistical analysis to determine whether the first form of the polymorphic DNA microsatellite marker segregates with progeny of the third cross that exhibit the enhanced wound healing phenotype, whereby either (1) the chromosomal locus identified in step (f) is confirmed, (2) the chromosomal locus identified in step (f) is narrowed, or (3) a new chromosomal locus containing at least one candidate gene involved in enhanced wound healing is identified.

17. The method of claim 16 wherein the first progeny of the cross between the $F_1$ mouse and the mouse of the second strain is a female.

18. The method of claim 16 wherein the first progeny of the cross between the $F_1$ mouse and the mouse of the second strain is a male.

19. A method of identifying candidate genes involved in enhanced wound healing, comprising the steps of:

(a) identifying a first and a second form of a polymorphic DNA microsatellite marker, wherein the first form identifies a first mouse strain and the second form identifies a second mouse strain, wherein the first mouse strain is a healer mouse strain and wherein the second mouse strain is not a healer mouse strain;

(b) performing a first cross between a mouse of the first mouse strain and a first mouse of the second mouse strain to form $F_1$ mice;

(c) performing a second cross between (1) a first $F_1$ mouse and (2) a mouse selected from the group consisting of (i) a second $F_1$ mouse, (ii) a second mouse of the second mouse strain, and (iii) a second mouse of the first mouse strain;

(d) identifying progeny of the second cross that exhibit an enhanced wound healing phenotype and progeny of the second cross that exhibit a non-enhanced wound healing phenotype;

(e) identifying genotypes of progeny of the second cross, wherein the genotypes are selected from the group consisting of (1) a genotype homozygous for the first form of the polymorphic DNA microsatellite marker, (2) a genotype homozygous for the second form of the polymorphic DNA microsatellite marker, and (3) a genotype heterozygous for the first and second forms of the polymorphic DNA microsatellite marker;

(f) performing a statistical analysis to determine whether the first form of the polymorphic DNA microsatellite marker segregates with progeny of the second cross that exhibit the enhanced wound healing phenotype, whereby a chromosomal locus is identified;

(g) identifying genes in the chromosomal locus as candidate genes involved in enhanced wound healing.

20. The method of claim 19, further comprising the step of assaying for differential expression of at least one gene in the chromosomal locus identified in step (g) in mice having the enhanced wound healing phenotype relative to mice having the non-enhanced wound healing phenotype, wherein differential expression of the at least one gene confirms the identification of the at least one gene as a candidate gene involved in enhanced wound healing.

* * * * *

SEQUENCE LISTING

<160> NUMBER OF SEQ ID NOS: 346

<210> SEQ ID NO 1
<211> LENGTH: 11
<212> TYPE: DNA
<213> ORGANISM: Mus musculus

<400> SEQUENCE: 1
ggcttcggtc t                                                          11

<210> SEQ ID NO 2
<211> LENGTH: 11
<212> TYPE: DNA
<213> ORGANISM: Mus musculus

<400> SEQUENCE: 2
agagcgaagt g                                                          11

```
<210> SEQ ID NO 3
<211> LENGTH: 11
<212> TYPE: DNA
<213> ORGANISM: Mus musculus

<400> SEQUENCE: 3
agcagtcccc t                                                    11

<210> SEQ ID NO 4
<211> LENGTH: 11
<212> TYPE: DNA
<213> ORGANISM: Mus musculus

<400> SEQUENCE: 4
gtggctcaca a                                                    11

<210> SEQ ID NO 5
<211> LENGTH: 11
<212> TYPE: DNA
<213> ORGANISM: Mus musculus

<400> SEQUENCE: 5
aggcagacag t                                                    11

<210> SEQ ID NO 6
<211> LENGTH: 11
<212> TYPE: DNA
<213> ORGANISM: Mus musculus

<400> SEQUENCE: 6
gctggccctt c                                                    11

<210> SEQ ID NO 7
<211> LENGTH: 11
<212> TYPE: DNA
<213> ORGANISM: Mus musculus

<400> SEQUENCE: 7
aggtcgggtg g                                                    11

<210> SEQ ID NO 8
<211> LENGTH: 11
<212> TYPE: DNA
<213> ORGANISM: Mus musculus

<400> SEQUENCE: 8
cgccgccggc t                                                    11

<210> SEQ ID NO 9
<211> LENGTH: 11
<212> TYPE: DNA
<213> ORGANISM: Mus musculus

<400> SEQUENCE: 9
ctgctcaggc t                                                    11

<210> SEQ ID NO 10
<211> LENGTH: 11
<212> TYPE: DNA
<213> ORGANISM: Mus musculus

<400> SEQUENCE: 10
```

-continued tgggcatcca c    11

<210> SEQ ID NO 11
<211> LENGTH: 11
<212> TYPE: DNA
<213> ORGANISM: Mus musculus

<400> SEQUENCE: 11
aaggaaatgg g    11

<210> SEQ ID NO 12
<211> LENGTH: 11
<212> TYPE: DNA
<213> ORGANISM: Mus musculus

<400> SEQUENCE: 12
atactgacat t    11

<210> SEQ ID NO 13
<211> LENGTH: 11
<212> TYPE: DNA
<213> ORGANISM: Mus musculus

<400> SEQUENCE: 13
cctttgtgac t    11

<210> SEQ ID NO 14
<211> LENGTH: 11
<212> TYPE: DNA
<213> ORGANISM: Mus musculus

<400> SEQUENCE: 14
gaacattgca c    11

<210> SEQ ID NO 15
<211> LENGTH: 11
<212> TYPE: DNA
<213> ORGANISM: Mus musculus

<400> SEQUENCE: 15
gggaaggcgg c    11

<210> SEQ ID NO 16
<211> LENGTH: 11
<212> TYPE: DNA
<213> ORGANISM: Mus musculus

<400> SEQUENCE: 16
atgactgata g    11

<210> SEQ ID NO 17
<211> LENGTH: 11
<212> TYPE: DNA
<213> ORGANISM: Mus musculus

<400> SEQUENCE: 17
cacaaacggt a    11

<210> SEQ ID NO 18
<211> LENGTH: 11
<212> TYPE: DNA
<213> ORGANISM: Mus musculus

<400> SEQUENCE: 18
caccaccgtt g                                    11

<210> SEQ ID NO 19
<211> LENGTH: 11
<212> TYPE: DNA
<213> ORGANISM: Mus musculus

<400> SEQUENCE: 19
cagaacccac g                                    11

<210> SEQ ID NO 20
<211> LENGTH: 11
<212> TYPE: DNA
<213> ORGANISM: Mus musculus

<400> SEQUENCE: 20
ccctgagtcc a                                    11

<210> SEQ ID NO 21
<211> LENGTH: 11
<212> TYPE: DNA
<213> ORGANISM: Mus musculus

<400> SEQUENCE: 21
ccctgggttc t                                    11

<210> SEQ ID NO 22
<211> LENGTH: 11
<212> TYPE: DNA
<213> ORGANISM: Mus musculus

<400> SEQUENCE: 22
gcccgggaat a                                    11

<210> SEQ ID NO 23
<211> LENGTH: 11
<212> TYPE: DNA
<213> ORGANISM: Mus musculus

<400> SEQUENCE: 23
gcggcggatg g                                    11

<210> SEQ ID NO 24
<211> LENGTH: 11
<212> TYPE: DNA
<213> ORGANISM: Mus musculus

<400> SEQUENCE: 24
ggaagccact t                                    11

<210> SEQ ID NO 25
<211> LENGTH: 11
<212> TYPE: DNA
<213> ORGANISM: Mus musculus

<400> SEQUENCE: 25
taaagaggcc g                                    11

<210> SEQ ID NO 26
<211> LENGTH: 11
<212> TYPE: DNA
<213> ORGANISM: Mus musculus -continued

<400> SEQUENCE: 26
tatgtcaagc t                                                           11

<210> SEQ ID NO 27
<211> LENGTH: 11
<212> TYPE: DNA
<213> ORGANISM: Mus musculus

<400> SEQUENCE: 27
tgggttgtct a                                                           11

<210> SEQ ID NO 28
<211> LENGTH: 11
<212> TYPE: DNA
<213> ORGANISM: Mus musculus

<400> SEQUENCE: 28
tgtagtgtaa t                                                           11

<210> SEQ ID NO 29
<211> LENGTH: 11
<212> TYPE: DNA
<213> ORGANISM: Mus musculus

<400> SEQUENCE: 29
ttcagtggac c                                                           11

<210> SEQ ID NO 30
<211> LENGTH: 11
<212> TYPE: DNA
<213> ORGANISM: Mus musculus

<400> SEQUENCE: 30
ttggtgaagg a                                                           11

<210> SEQ ID NO 31
<211> LENGTH: 11
<212> TYPE: DNA
<213> ORGANISM: Mus musculus

<400> SEQUENCE: 31
agaaaccaat a                                                           11

<210> SEQ ID NO 32
<211> LENGTH: 11
<212> TYPE: DNA
<213> ORGANISM: Mus musculus

<400> SEQUENCE: 32
agtgaggaag a                                                           11

<210> SEQ ID NO 33
<211> LENGTH: 11
<212> TYPE: DNA
<213> ORGANISM: Mus musculus

<400> SEQUENCE: 33
ataatacata a                                                           11

<210> SEQ ID NO 34
<211> LENGTH: 11
<212> TYPE: DNA
<213> ORGANISM: Mus musculus

```
<400> SEQUENCE: 34
atactgaagc c                                                      11

<210> SEQ ID NO 35
<211> LENGTH: 11
<212> TYPE: DNA
<213> ORGANISM: Mus musculus

<400> SEQUENCE: 35
attctccagt g                                                      11

<210> SEQ ID NO 36
<211> LENGTH: 11
<212> TYPE: DNA
<213> ORGANISM: Mus musculus

<400> SEQUENCE: 36
caaactctca c                                                      11

<210> SEQ ID NO 37
<211> LENGTH: 11
<212> TYPE: DNA
<213> ORGANISM: Mus musculus

<400> SEQUENCE: 37
cagtcaccaa c                                                      11

<210> SEQ ID NO 38
<211> LENGTH: 11
<212> TYPE: DNA
<213> ORGANISM: Mus musculus

<400> SEQUENCE: 38
cccacaaggt a                                                      11

<210> SEQ ID NO 39
<211> LENGTH: 11
<212> TYPE: DNA
<213> ORGANISM: Mus musculus

<400> SEQUENCE: 39
ccttgctcaa t                                                      11

<210> SEQ ID NO 40
<211> LENGTH: 11
<212> TYPE: DNA
<213> ORGANISM: Mus musculus

<400> SEQUENCE: 40
cctttgagat c                                                      11

<210> SEQ ID NO 41
<211> LENGTH: 11
<212> TYPE: DNA
<213> ORGANISM: Mus musculus

<400> SEQUENCE: 41
ctagtctttg t                                                      11

<210> SEQ ID NO 42
<211> LENGTH: 11
<212> TYPE: DNA
```

```
<213> ORGANISM: Mus musculus

<400> SEQUENCE: 42
ctgaacatct c                                                          11

<210> SEQ ID NO 43
<211> LENGTH: 11
<212> TYPE: DNA
<213> ORGANISM: Mus musculus

<400> SEQUENCE: 43
ggcaagcccc a                                                          11

<210> SEQ ID NO 44
<211> LENGTH: 11
<212> TYPE: DNA
<213> ORGANISM: Mus musculus

<400> SEQUENCE: 44
ggcctggctt a                                                          11

<210> SEQ ID NO 45
<211> LENGTH: 11
<212> TYPE: DNA
<213> ORGANISM: Mus musculus

<400> SEQUENCE: 45
tccccgtaca t                                                          11

<210> SEQ ID NO 46
<211> LENGTH: 11
<212> TYPE: DNA
<213> ORGANISM: Mus musculus

<400> SEQUENCE: 46
tccctattaa g                                                          11

<210> SEQ ID NO 47
<211> LENGTH: 11
<212> TYPE: DNA
<213> ORGANISM: Mus musculus

<400> SEQUENCE: 47
tcttctcaca a                                                          11

<210> SEQ ID NO 48
<211> LENGTH: 11
<212> TYPE: DNA
<213> ORGANISM: Mus musculus

<400> SEQUENCE: 48
tggcccaaat t                                                          11

<210> SEQ ID NO 49
<211> LENGTH: 11
<212> TYPE: DNA
<213> ORGANISM: Mus musculus

<400> SEQUENCE: 49
aaggtggaag a                                                          11

<210> SEQ ID NO 50
<211> LENGTH: 11
```

-continued

```
<212> TYPE: DNA
<213> ORGANISM: Mus musculus

<400> SEQUENCE: 50
acatcataga t                                                        11

<210> SEQ ID NO 51
<211> LENGTH: 11
<212> TYPE: DNA
<213> ORGANISM: Mus musculus

<400> SEQUENCE: 51
aggaaggcgg c                                                        11

<210> SEQ ID NO 52
<211> LENGTH: 11
<212> TYPE: DNA
<213> ORGANISM: Mus musculus

<400> SEQUENCE: 52
caagtggaaa a                                                        11

<210> SEQ ID NO 53
<211> LENGTH: 11
<212> TYPE: DNA
<213> ORGANISM: Mus musculus

<400> SEQUENCE: 53
cacgctcccg g                                                        11

<210> SEQ ID NO 54
<211> LENGTH: 11
<212> TYPE: DNA
<213> ORGANISM: Mus musculus

<400> SEQUENCE: 54
caggccacac a                                                        11

<210> SEQ ID NO 55
<211> LENGTH: 11
<212> TYPE: DNA
<213> ORGANISM: Mus musculus

<400> SEQUENCE: 55
ccagaacaga c                                                        11

<210> SEQ ID NO 56
<211> LENGTH: 11
<212> TYPE: DNA
<213> ORGANISM: Mus musculus

<400> SEQUENCE: 56
cccagagcac t                                                        11

<210> SEQ ID NO 57
<211> LENGTH: 11
<212> TYPE: DNA
<213> ORGANISM: Mus musculus

<400> SEQUENCE: 57
ccctaaactg a                                                        11

<210> SEQ ID NO 58
```

-continued

<210> SEQ ID NO 58
<211> LENGTH: 11
<212> TYPE: DNA
<213> ORGANISM: Mus musculus

<400> SEQUENCE: 58
cctgatcttt a                                                          11

<210> SEQ ID NO 59
<211> LENGTH: 11
<212> TYPE: DNA
<213> ORGANISM: Mus musculus

<400> SEQUENCE: 59
cctttaatcc c                                                          11

<210> SEQ ID NO 60
<211> LENGTH: 11
<212> TYPE: DNA
<213> ORGANISM: Mus musculus

<400> SEQUENCE: 60
ctcaacagca a                                                          11

<210> SEQ ID NO 61
<211> LENGTH: 11
<212> TYPE: DNA
<213> ORGANISM: Mus musculus

<400> SEQUENCE: 61
ctcctggaca c                                                          11

<210> SEQ ID NO 62
<211> LENGTH: 11
<212> TYPE: DNA
<213> ORGANISM: Mus musculus

<400> SEQUENCE: 62
ctggctttca g                                                          11

<210> SEQ ID NO 63
<211> LENGTH: 11
<212> TYPE: DNA
<213> ORGANISM: Mus musculus

<400> SEQUENCE: 63
gactttggaa a                                                          11

<210> SEQ ID NO 64
<211> LENGTH: 11
<212> TYPE: DNA
<213> ORGANISM: Mus musculus

<400> SEQUENCE: 64
gagcgttttg g                                                          11

<210> SEQ ID NO 65
<211> LENGTH: 11
<212> TYPE: DNA
<213> ORGANISM: Mus musculus

<400> SEQUENCE: 65
gatgacacca g                                                          11

```
<210> SEQ ID NO 66
<211> LENGTH: 11
<212> TYPE: DNA
<213> ORGANISM: Mus musculus

<400> SEQUENCE: 66
gctgcagttg a                                                        11

<210> SEQ ID NO 67
<211> LENGTH: 11
<212> TYPE: DNA
<213> ORGANISM: Mus musculus

<400> SEQUENCE: 67
gctgccctcc a                                                        11

<210> SEQ ID NO 68
<211> LENGTH: 11
<212> TYPE: DNA
<213> ORGANISM: Mus musculus

<400> SEQUENCE: 68
gtctgctgat g                                                        11

<210> SEQ ID NO 69
<211> LENGTH: 11
<212> TYPE: DNA
<213> ORGANISM: Mus musculus

<400> SEQUENCE: 69
gtggaggcgc c                                                        11

<210> SEQ ID NO 70
<211> LENGTH: 11
<212> TYPE: DNA
<213> ORGANISM: Mus musculus

<400> SEQUENCE: 70
gtgggcgtgt a                                                        11

<210> SEQ ID NO 71
<211> LENGTH: 11
<212> TYPE: DNA
<213> ORGANISM: Mus musculus

<400> SEQUENCE: 71
taaacctgct a                                                        11

<210> SEQ ID NO 72
<211> LENGTH: 11
<212> TYPE: DNA
<213> ORGANISM: Mus musculus

<400> SEQUENCE: 72
tatcccacgc c                                                        11

<210> SEQ ID NO 73
<211> LENGTH: 11
<212> TYPE: DNA
<213> ORGANISM: Mus musculus

<400> SEQUENCE: 73
tcggtttctg c                                                        11
```

<210> SEQ ID NO 74
<211> LENGTH: 11
<212> TYPE: DNA
<213> ORGANISM: Mus musculus

<400> SEQUENCE: 74
tctcaccacc c                                                    11

<210> SEQ ID NO 75
<211> LENGTH: 11
<212> TYPE: DNA
<213> ORGANISM: Mus musculus

<400> SEQUENCE: 75
tgaccccggg a                                                    11

<210> SEQ ID NO 76
<211> LENGTH: 11
<212> TYPE: DNA
<213> ORGANISM: Mus musculus

<400> SEQUENCE: 76
tgcacagtgc t                                                    11

<210> SEQ ID NO 77
<211> LENGTH: 11
<212> TYPE: DNA
<213> ORGANISM: Mus musculus

<400> SEQUENCE: 77
tggtctggtc c                                                    11

<210> SEQ ID NO 78
<211> LENGTH: 11
<212> TYPE: DNA
<213> ORGANISM: Mus musculus

<400> SEQUENCE: 78
tgtaacagga c                                                    11

<210> SEQ ID NO 79
<211> LENGTH: 11
<212> TYPE: DNA
<213> ORGANISM: Mus musculus

<400> SEQUENCE: 79
ttcaggtggt t                                                    11

<210> SEQ ID NO 80
<211> LENGTH: 11
<212> TYPE: DNA
<213> ORGANISM: Mus musculus

<400> SEQUENCE: 80
ttggctgccc a                                                    11

<210> SEQ ID NO 81
<211> LENGTH: 11
<212> TYPE: DNA
<213> ORGANISM: Mus musculus

<400> SEQUENCE: 81
aaaacagtgg c                                                    11

```
<210> SEQ ID NO 82
<211> LENGTH: 11
<212> TYPE: DNA
<213> ORGANISM: Mus musculus

<400> SEQUENCE: 82
aaagcagtgc t                                                          11

<210> SEQ ID NO 83
<211> LENGTH: 11
<212> TYPE: DNA
<213> ORGANISM: Mus musculus

<400> SEQUENCE: 83
aagaggcaag a                                                          11

<210> SEQ ID NO 84
<211> LENGTH: 11
<212> TYPE: DNA
<213> ORGANISM: Mus musculus

<400> SEQUENCE: 84
aagcaacagg t                                                          11

<210> SEQ ID NO 85
<211> LENGTH: 11
<212> TYPE: DNA
<213> ORGANISM: Mus musculus

<400> SEQUENCE: 85
aaggtcgagc t                                                          11

<210> SEQ ID NO 86
<211> LENGTH: 11
<212> TYPE: DNA
<213> ORGANISM: Mus musculus

<400> SEQUENCE: 86
acagaactct t                                                          11

<210> SEQ ID NO 87
<211> LENGTH: 11
<212> TYPE: DNA
<213> ORGANISM: Mus musculus

<400> SEQUENCE: 87
accttggaag g                                                          11

<210> SEQ ID NO 88
<211> LENGTH: 11
<212> TYPE: DNA
<213> ORGANISM: Mus musculus

<400> SEQUENCE: 88
actctttgtt t                                                          11

<210> SEQ ID NO 89
<211> LENGTH: 11
<212> TYPE: DNA
<213> ORGANISM: Mus musculus

<400> SEQUENCE: 89
```
actggctggg c        11

<210> SEQ ID NO 90
<211> LENGTH: 11
<212> TYPE: DNA
<213> ORGANISM: Mus musculus

<400> SEQUENCE: 90
acttattatg c        11

<210> SEQ ID NO 91
<211> LENGTH: 11
<212> TYPE: DNA
<213> ORGANISM: Mus musculus

<400> SEQUENCE: 91
agaaccatta a        11

<210> SEQ ID NO 92
<211> LENGTH: 11
<212> TYPE: DNA
<213> ORGANISM: Mus musculus

<400> SEQUENCE: 92
agaccctctc a        11

<210> SEQ ID NO 93
<211> LENGTH: 11
<212> TYPE: DNA
<213> ORGANISM: Mus musculus

<400> SEQUENCE: 93
agcaattcaa a        11

<210> SEQ ID NO 94
<211> LENGTH: 11
<212> TYPE: DNA
<213> ORGANISM: Mus musculus

<400> SEQUENCE: 94
atcaacaccg c        11

<210> SEQ ID NO 95
<211> LENGTH: 11
<212> TYPE: DNA
<213> ORGANISM: Mus musculus

<400> SEQUENCE: 95
atccgaaaga t        11

<210> SEQ ID NO 96
<211> LENGTH: 11
<212> TYPE: DNA
<213> ORGANISM: Mus musculus

<400> SEQUENCE: 96
caccaccaca g        11

<210> SEQ ID NO 97
<211> LENGTH: 11
<212> TYPE: DNA
<213> ORGANISM: Mus musculus

<400> SEQUENCE: 97

-continued caccttggtg c                                            11

<210> SEQ ID NO 98
<211> LENGTH: 11
<212> TYPE: DNA
<213> ORGANISM: Mus musculus

<400> SEQUENCE: 98
cacgggacca c                                            11

<210> SEQ ID NO 99
<211> LENGTH: 11
<212> TYPE: DNA
<213> ORGANISM: Mus musculus

<400> SEQUENCE: 99
cactgacctc c                                            11

<210> SEQ ID NO 100
<211> LENGTH: 11
<212> TYPE: DNA
<213> ORGANISM: Mus musculus

<400> SEQUENCE: 100
cattatgggt g                                            11

<210> SEQ ID NO 101
<211> LENGTH: 11
<212> TYPE: DNA
<213> ORGANISM: Mus musculus

<400> SEQUENCE: 101
cccaatggcc c                                            11

<210> SEQ ID NO 102
<211> LENGTH: 11
<212> TYPE: DNA
<213> ORGANISM: Mus musculus

<400> SEQUENCE: 102
cccggactta c                                            11

<210> SEQ ID NO 103
<211> LENGTH: 11
<212> TYPE: DNA
<213> ORGANISM: Mus musculus

<400> SEQUENCE: 103
cccgtagccc c                                            11

<210> SEQ ID NO 104
<211> LENGTH: 11
<212> TYPE: DNA
<213> ORGANISM: Mus musculus

<400> SEQUENCE: 104
cctacagttg a                                            11

<210> SEQ ID NO 105
<211> LENGTH: 11
<212> TYPE: DNA
<213> ORGANISM: Mus musculus -continued

<400> SEQUENCE: 105
cctcggaaaa t    11

<210> SEQ ID NO 106
<211> LENGTH: 11
<212> TYPE: DNA
<213> ORGANISM: Mus musculus

<400> SEQUENCE: 106
cctgtgtgaa a    11

<210> SEQ ID NO 107
<211> LENGTH: 11
<212> TYPE: DNA
<213> ORGANISM: Mus musculus

<400> SEQUENCE: 107
cgcctgctag c    11

<210> SEQ ID NO 108
<211> LENGTH: 11
<212> TYPE: DNA
<213> ORGANISM: Mus musculus

<400> SEQUENCE: 108
cgctggttcc a    11

<210> SEQ ID NO 109
<211> LENGTH: 11
<212> TYPE: DNA
<213> ORGANISM: Mus musculus

<400> SEQUENCE: 109
cggttccacc c    11

<210> SEQ ID NO 110
<211> LENGTH: 11
<212> TYPE: DNA
<213> ORGANISM: Mus musculus

<400> SEQUENCE: 110
ctaataaagc c    11

<210> SEQ ID NO 111
<211> LENGTH: 11
<212> TYPE: DNA
<213> ORGANISM: Mus musculus

<400> SEQUENCE: 111
ctaccaggat a    11

<210> SEQ ID NO 112
<211> LENGTH: 11
<212> TYPE: DNA
<213> ORGANISM: Mus musculus

<400> SEQUENCE: 112
ctgctatccg a    11

<210> SEQ ID NO 113
<211> LENGTH: 11
<212> TYPE: DNA
<213> ORGANISM: Mus musculus

<400> SEQUENCE: 113
ctgctttgtg c    11

<210> SEQ ID NO 114
<211> LENGTH: 11
<212> TYPE: DNA
<213> ORGANISM: Mus musculus

<400> SEQUENCE: 114
ctgggcgtgt c    11

<210> SEQ ID NO 115
<211> LENGTH: 11
<212> TYPE: DNA
<213> ORGANISM: Mus musculus

<400> SEQUENCE: 115
ctgtaggtga t    11

<210> SEQ ID NO 116
<211> LENGTH: 11
<212> TYPE: DNA
<213> ORGANISM: Mus musculus

<400> SEQUENCE: 116
ctgtgccctc c    11

<210> SEQ ID NO 117
<211> LENGTH: 11
<212> TYPE: DNA
<213> ORGANISM: Mus musculus

<400> SEQUENCE: 117
cttaaggatc c    11

<210> SEQ ID NO 118
<211> LENGTH: 11
<212> TYPE: DNA
<213> ORGANISM: Mus musculus

<400> SEQUENCE: 118
gaatctgaag t    11

<210> SEQ ID NO 119
<211> LENGTH: 11
<212> TYPE: DNA
<213> ORGANISM: Mus musculus

<400> SEQUENCE: 119
gaatgcaggg a    11

<210> SEQ ID NO 120
<211> LENGTH: 11
<212> TYPE: DNA
<213> ORGANISM: Mus musculus

<400> SEQUENCE: 120
gaggagaaga a    11

<210> SEQ ID NO 121
<211> LENGTH: 11
<212> TYPE: DNA

<213> ORGANISM: Mus musculus

<400> SEQUENCE: 121
gatgcatagt g  11

<210> SEQ ID NO 122
<211> LENGTH: 11
<212> TYPE: DNA
<213> ORGANISM: Mus musculus

<400> SEQUENCE: 122
gatgtgacca c  11

<210> SEQ ID NO 123
<211> LENGTH: 11
<212> TYPE: DNA
<213> ORGANISM: Mus musculus

<400> SEQUENCE: 123
gatttctgtc t  11

<210> SEQ ID NO 124
<211> LENGTH: 11
<212> TYPE: DNA
<213> ORGANISM: Mus musculus

<400> SEQUENCE: 124
gcaccgaaca c  11

<210> SEQ ID NO 125
<211> LENGTH: 11
<212> TYPE: DNA
<213> ORGANISM: Mus musculus

<400> SEQUENCE: 125
gcatacggcg c  11

<210> SEQ ID NO 126
<211> LENGTH: 11
<212> TYPE: DNA
<213> ORGANISM: Mus musculus

<400> SEQUENCE: 126
gcattgcatc t  11

<210> SEQ ID NO 127
<211> LENGTH: 11
<212> TYPE: DNA
<213> ORGANISM: Mus musculus

<400> SEQUENCE: 127
gccaagggtc a  11

<210> SEQ ID NO 128
<211> LENGTH: 11
<212> TYPE: DNA
<213> ORGANISM: Mus musculus

<400> SEQUENCE: 128
gccaagtgga g  11

<210> SEQ ID NO 129
<211> LENGTH: 11

```
<212> TYPE: DNA
<213> ORGANISM: Mus musculus

<400> SEQUENCE: 129
gcctaatgta c                                                    11

<210> SEQ ID NO 130
<211> LENGTH: 11
<212> TYPE: DNA
<213> ORGANISM: Mus musculus

<400> SEQUENCE: 130
gcctcggggg a                                                    11

<210> SEQ ID NO 131
<211> LENGTH: 11
<212> TYPE: DNA
<213> ORGANISM: Mus musculus

<400> SEQUENCE: 131
gcgacgcggg c                                                    11

<210> SEQ ID NO 132
<211> LENGTH: 11
<212> TYPE: DNA
<213> ORGANISM: Mus musculus

<400> SEQUENCE: 132
gcggcgggat g                                                    11

<210> SEQ ID NO 133
<211> LENGTH: 11
<212> TYPE: DNA
<213> ORGANISM: Mus musculus

<400> SEQUENCE: 133
gctcaggatt c                                                    11

<210> SEQ ID NO 134
<211> LENGTH: 11
<212> TYPE: DNA
<213> ORGANISM: Mus musculus

<400> SEQUENCE: 134
gctggcagac g                                                    11

<210> SEQ ID NO 135
<211> LENGTH: 11
<212> TYPE: DNA
<213> ORGANISM: Mus musculus

<400> SEQUENCE: 135
gcttgcttcc t                                                    11

<210> SEQ ID NO 136
<211> LENGTH: 11
<212> TYPE: DNA
<213> ORGANISM: Mus musculus

<400> SEQUENCE: 136
ggaaggtgtc t                                                    11

<210> SEQ ID NO 137
```

-continued

<210> SEQ ID NO 137
<211> LENGTH: 11
<212> TYPE: DNA
<213> ORGANISM: Mus musculus

<400> SEQUENCE: 137
ggatttggct t                                                          11

<210> SEQ ID NO 138
<211> LENGTH: 11
<212> TYPE: DNA
<213> ORGANISM: Mus musculus

<400> SEQUENCE: 138
gggagctgtg c                                                          11

<210> SEQ ID NO 139
<211> LENGTH: 11
<212> TYPE: DNA
<213> ORGANISM: Mus musculus

<400> SEQUENCE: 139
ggggaaatcg c                                                          11

<210> SEQ ID NO 140
<211> LENGTH: 11
<212> TYPE: DNA
<213> ORGANISM: Mus musculus

<400> SEQUENCE: 140
ggggctcagc c                                                          11

<210> SEQ ID NO 141
<211> LENGTH: 11
<212> TYPE: DNA
<213> ORGANISM: Mus musculus

<400> SEQUENCE: 141
ggtgagcctg a                                                          11

<210> SEQ ID NO 142
<211> LENGTH: 11
<212> TYPE: DNA
<213> ORGANISM: Mus musculus

<400> SEQUENCE: 142
ggtgggacac a                                                          11

<210> SEQ ID NO 143
<211> LENGTH: 11
<212> TYPE: DNA
<213> ORGANISM: Mus musculus

<400> SEQUENCE: 143
gtaagcataa a                                                          11

<210> SEQ ID NO 144
<211> LENGTH: 11
<212> TYPE: DNA
<213> ORGANISM: Mus musculus

<400> SEQUENCE: 144
gtctgggggg a                                                          11

<210> SEQ ID NO 145
<211> LENGTH: 11
<212> TYPE: DNA
<213> ORGANISM: Mus musculus

<400> SEQUENCE: 145
gtggtaggct a                                                                11

<210> SEQ ID NO 146
<211> LENGTH: 11
<212> TYPE: DNA
<213> ORGANISM: Mus musculus

<400> SEQUENCE: 146
gttgctgaga a                                                                11

<210> SEQ ID NO 147
<211> LENGTH: 11
<212> TYPE: DNA
<213> ORGANISM: Mus musculus

<400> SEQUENCE: 147 gttgggggggg g                                                               11

<210> SEQ ID NO 148
<211> LENGTH: 11
<212> TYPE: DNA
<213> ORGANISM: Mus musculus

<400> SEQUENCE: 148
taactgacaa t                                                                11

<210> SEQ ID NO 149
<211> LENGTH: 11
<212> TYPE: DNA
<213> ORGANISM: Mus musculus

<400> SEQUENCE: 149
tatacaatac a                                                                11

<210> SEQ ID NO 150
<211> LENGTH: 11
<212> TYPE: DNA
<213> ORGANISM: Mus musculus

<400> SEQUENCE: 150
tccactgtgc a                                                                11

<210> SEQ ID NO 151
<211> LENGTH: 11
<212> TYPE: DNA
<213> ORGANISM: Mus musculus

<400> SEQUENCE: 151
tctggacgcg g                                                                11

<210> SEQ ID NO 152
<211> LENGTH: 11
<212> TYPE: DNA
<213> ORGANISM: Mus musculus

<400> SEQUENCE: 152
tgaaacactg t                                                                11

<210> SEQ ID NO 153
<211> LENGTH: 11
<212> TYPE: DNA
<213> ORGANISM: Mus musculus

<400> SEQUENCE: 153 tgacccoggg t                                                    11

<210> SEQ ID NO 154
<211> LENGTH: 11
<212> TYPE: DNA
<213> ORGANISM: Mus musculus

<400> SEQUENCE: 154
tgcctgtgat a                                                    11

<210> SEQ ID NO 155
<211> LENGTH: 11
<212> TYPE: DNA
<213> ORGANISM: Mus musculus

<400> SEQUENCE: 155
tggatcctga g                                                    11

<210> SEQ ID NO 156
<211> LENGTH: 11
<212> TYPE: DNA
<213> ORGANISM: Mus musculus

<400> SEQUENCE: 156
tgggcaaagc c                                                    11

<210> SEQ ID NO 157
<211> LENGTH: 11
<212> TYPE: DNA
<213> ORGANISM: Mus musculus

<400> SEQUENCE: 157
tggtgacaaa a                                                    11

<210> SEQ ID NO 158
<211> LENGTH: 11
<212> TYPE: DNA
<213> ORGANISM: Mus musculus

<400> SEQUENCE: 158
tgtgccaagt g                                                    11

<210> SEQ ID NO 159
<211> LENGTH: 11
<212> TYPE: DNA
<213> ORGANISM: Mus musculus

<400> SEQUENCE: 159
tgttcatctt g                                                    11

<210> SEQ ID NO 160
<211> LENGTH: 11
<212> TYPE: DNA
<213> ORGANISM: Mus musculus

<400> SEQUENCE: 160
ttcagctcga g                                                    11

<210> SEQ ID NO 161
<211> LENGTH: 11
<212> TYPE: DNA
<213> ORGANISM: Mus musculus

<400> SEQUENCE: 161
ttgctgcagt g                                              11

<210> SEQ ID NO 162
<211> LENGTH: 11
<212> TYPE: DNA
<213> ORGANISM: Mus musculus

<400> SEQUENCE: 162
cggtccaggg a                                              11

<210> SEQ ID NO 163
<211> LENGTH: 11
<212> TYPE: DNA
<213> ORGANISM: Mus musculus

<400> SEQUENCE: 163
gtggctcaca a                                              11

<210> SEQ ID NO 164
<211> LENGTH: 11
<212> TYPE: DNA
<213> ORGANISM: Mus musculus

<400> SEQUENCE: 164
ggcttcggtc t                                              11

<210> SEQ ID NO 165
<211> LENGTH: 11
<212> TYPE: DNA
<213> ORGANISM: Mus musculus

<400> SEQUENCE: 165
aggtcgggtg g                                              11

<210> SEQ ID NO 166
<211> LENGTH: 11
<212> TYPE: DNA
<213> ORGANISM: Mus musculus

<400> SEQUENCE: 166
cacaaacggt a                                              11

<210> SEQ ID NO 167
<211> LENGTH: 11
<212> TYPE: DNA
<213> ORGANISM: Mus musculus

<400> SEQUENCE: 167
tgggttgtct a                                              11

<210> SEQ ID NO 168
<211> LENGTH: 11
<212> TYPE: DNA
<213> ORGANISM: Mus musculus

<400> SEQUENCE: 168

-continued cgccgccggc t                                                    11

<210> SEQ ID NO 169
<211> LENGTH: 11
<212> TYPE: DNA
<213> ORGANISM: Mus musculus

<400> SEQUENCE: 169
ctgctcaggc t                                                    11

<210> SEQ ID NO 170
<211> LENGTH: 11
<212> TYPE: DNA
<213> ORGANISM: Mus musculus

<400> SEQUENCE: 170
gctggccctt c                                                    11

<210> SEQ ID NO 171
<211> LENGTH: 11
<212> TYPE: DNA
<213> ORGANISM: Mus musculus

<400> SEQUENCE: 171
aggcagacag t                                                    11

<210> SEQ ID NO 172
<211> LENGTH: 11
<212> TYPE: DNA
<213> ORGANISM: Mus musculus

<400> SEQUENCE: 172
ttggctgccc a                                                    11

<210> SEQ ID NO 173
<211> LENGTH: 11
<212> TYPE: DNA
<213> ORGANISM: Mus musculus

<400> SEQUENCE: 173
gcccgggaat a                                                    11

<210> SEQ ID NO 174
<211> LENGTH: 11
<212> TYPE: DNA
<213> ORGANISM: Mus musculus

<400> SEQUENCE: 174
agagcgaagt g                                                    11

<210> SEQ ID NO 175
<211> LENGTH: 11
<212> TYPE: DNA
<213> ORGANISM: Mus musculus

<400> SEQUENCE: 175
cagaacccac g                                                    11

<210> SEQ ID NO 176
<211> LENGTH: 11
<212> TYPE: DNA
<213> ORGANISM: Mus musculus

<400> SEQUENCE: 176

```
catcgccagt g                                                          11

<210> SEQ ID NO 177
<211> LENGTH: 11
<212> TYPE: DNA
<213> ORGANISM: Mus musculus

<400> SEQUENCE: 177
ccccagccag t                                                          11

<210> SEQ ID NO 178
<211> LENGTH: 11
<212> TYPE: DNA
<213> ORGANISM: Mus musculus

<400> SEQUENCE: 178
agcagtcccc t                                                          11

<210> SEQ ID NO 179
<211> LENGTH: 11
<212> TYPE: DNA
<213> ORGANISM: Mus musculus

<400> SEQUENCE: 179
caaactctca c                                                          11

<210> SEQ ID NO 180
<211> LENGTH: 11
<212> TYPE: DNA
<213> ORGANISM: Mus musculus

<400> SEQUENCE: 180
ctaataaagc c                                                          11

<210> SEQ ID NO 181
<211> LENGTH: 11
<212> TYPE: DNA
<213> ORGANISM: Mus musculus

<400> SEQUENCE: 181
ggcaagcccc a                                                          11

<210> SEQ ID NO 182
<211> LENGTH: 11
<212> TYPE: DNA
<213> ORGANISM: Mus musculus

<400> SEQUENCE: 182
caaggtgaca g                                                          11

<210> SEQ ID NO 183
<211> LENGTH: 11
<212> TYPE: DNA
<213> ORGANISM: Mus musculus

<400> SEQUENCE: 183
ccagaacaga c                                                          11

<210> SEQ ID NO 184
<211> LENGTH: 11
<212> TYPE: DNA
<213> ORGANISM: Mus musculus
```

-continued

<400> SEQUENCE: 184
ctgaacatct c					11

<210> SEQ ID NO 185
<211> LENGTH: 11
<212> TYPE: DNA
<213> ORGANISM: Mus musculus

<400> SEQUENCE: 185
gcctttatga g					11

<210> SEQ ID NO 186
<211> LENGTH: 11
<212> TYPE: DNA
<213> ORGANISM: Mus musculus

<400> SEQUENCE: 186
ggaagccact t					11

<210> SEQ ID NO 187
<211> LENGTH: 11
<212> TYPE: DNA
<213> ORGANISM: Mus musculus

<400> SEQUENCE: 187
gtgaacgtgc c					11

<210> SEQ ID NO 188
<211> LENGTH: 11
<212> TYPE: DNA
<213> ORGANISM: Mus musculus

<400> SEQUENCE: 188
gtgggcgtgt a					11

<210> SEQ ID NO 189
<211> LENGTH: 11
<212> TYPE: DNA
<213> ORGANISM: Mus musculus

<400> SEQUENCE: 189
aacaccaagc t					11

<210> SEQ ID NO 190
<211> LENGTH: 11
<212> TYPE: DNA
<213> ORGANISM: Mus musculus

<400> SEQUENCE: 190
caccaccaca g					11

<210> SEQ ID NO 191
<211> LENGTH: 11
<212> TYPE: DNA
<213> ORGANISM: Mus musculus

<400> SEQUENCE: 191
caccaccgtt g					11

<210> SEQ ID NO 192
<211> LENGTH: 11
<212> TYPE: DNA
<213> ORGANISM: Mus musculus -continued

<400> SEQUENCE: 192
cacgctcccg g                                                          11

<210> SEQ ID NO 193
<211> LENGTH: 11
<212> TYPE: DNA
<213> ORGANISM: Mus musculus

<400> SEQUENCE: 193
cccgtgtgct c                                                          11

<210> SEQ ID NO 194
<211> LENGTH: 11
<212> TYPE: DNA
<213> ORGANISM: Mus musculus

<400> SEQUENCE: 194
ccttgctcaa t                                                          11

<210> SEQ ID NO 195
<211> LENGTH: 11
<212> TYPE: DNA
<213> ORGANISM: Mus musculus

<400> SEQUENCE: 195
ctgctatccg a                                                          11

<210> SEQ ID NO 196
<211> LENGTH: 11
<212> TYPE: DNA
<213> ORGANISM: Mus musculus

<400> SEQUENCE: 196
gaacattgca c                                                          11

<210> SEQ ID NO 197
<211> LENGTH: 11
<212> TYPE: DNA
<213> ORGANISM: Mus musculus

<400> SEQUENCE: 197
ggatttggct t                                                          11

<210> SEQ ID NO 198
<211> LENGTH: 11
<212> TYPE: DNA
<213> ORGANISM: Mus musculus

<400> SEQUENCE: 198
gggaaggcgg c                                                          11

<210> SEQ ID NO 199
<211> LENGTH: 11
<212> TYPE: DNA
<213> ORGANISM: Mus musculus

<400> SEQUENCE: 199
gtctgctgat g                                                          11

<210> SEQ ID NO 200
<211> LENGTH: 11
<212> TYPE: DNA

<213> ORGANISM: Mus musculus

<400> SEQUENCE: 200
tcaggctgcc t                                                              11

<210> SEQ ID NO 201
    <211> LENGTH: 11
    <212> TYPE: DNA
    <213> ORGANISM: Mus musculus

<400> SEQUENCE: 201
tggatcctga g                                                              11

<210> SEQ ID NO 202
    <211> LENGTH: 11
    <212> TYPE: DNA
    <213> ORGANISM: Mus musculus

<400> SEQUENCE: 202
cgctggttcc a                                                              11

<210> SEQ ID NO 203
    <211> LENGTH: 11
    <212> TYPE: DNA
    <213> ORGANISM: Mus musculus

<400> SEQUENCE: 203
ctcctggaca c                                                              11

<210> SEQ ID NO 204
    <211> LENGTH: 11
    <212> TYPE: DNA
    <213> ORGANISM: Mus musculus

<400> SEQUENCE: 204
tatgtcaagc t                                                              11

<210> SEQ ID NO 205
    <211> LENGTH: 11
    <212> TYPE: DNA
    <213> ORGANISM: Mus musculus

<400> SEQUENCE: 205
tcgtgattgt g                                                              11

<210> SEQ ID NO 206
    <211> LENGTH: 11
    <212> TYPE: DNA
    <213> ORGANISM: Mus musculus

<400> SEQUENCE: 206
ttcagtggac c                                                              11

<210> SEQ ID NO 207
    <211> LENGTH: 11
    <212> TYPE: DNA
    <213> ORGANISM: Mus musculus

<400> SEQUENCE: 207
aagaggcaag a                                                              11

<210> SEQ ID NO 208
    <211> LENGTH: 11

-continued

```
<212> TYPE: DNA
<213> ORGANISM: Mus musculus

<400> SEQUENCE: 208
atactgacat t                                                    11

<210> SEQ ID NO 209
<211> LENGTH: 11
<212> TYPE: DNA
<213> ORGANISM: Mus musculus

<400> SEQUENCE: 209
caagtggaaa a                                                    11

<210> SEQ ID NO 210
<211> LENGTH: 11
<212> TYPE: DNA
<213> ORGANISM: Mus musculus

<400> SEQUENCE: 210
cccaatggcc c                                                    11

<210> SEQ ID NO 211
<211> LENGTH: 11
<212> TYPE: DNA
<213> ORGANISM: Mus musculus

<400> SEQUENCE: 211
cctaccaaga c                                                    11

<210> SEQ ID NO 212
<211> LENGTH: 11
<212> TYPE: DNA
<213> ORGANISM: Mus musculus

<400> SEQUENCE: 212
gatgacacca g                                                    11

<210> SEQ ID NO 213
<211> LENGTH: 11
<212> TYPE: DNA
<213> ORGANISM: Mus musculus

<400> SEQUENCE: 213
gattccgtga g                                                    11

<210> SEQ ID NO 214
<211> LENGTH: 11
<212> TYPE: DNA
<213> ORGANISM: Mus musculus

<400> SEQUENCE: 214
gcagagtgcg c                                                    11

<210> SEQ ID NO 215
<211> LENGTH: 11
<212> TYPE: DNA
<213> ORGANISM: Mus musculus

<400> SEQUENCE: 215
gccaagtgga g                                                    11

<210> SEQ ID NO 216
```

<211> LENGTH: 11
<212> TYPE: DNA
<213> ORGANISM: Mus musculus

<400> SEQUENCE: 216
gcggcggatg g                                                    11

<210> SEQ ID NO 217
<211> LENGTH: 11
<212> TYPE: DNA
<213> ORGANISM: Mus musculus

<400> SEQUENCE: 217
gtggaggcgc c                                                    11

<210> SEQ ID NO 218
<211> LENGTH: 11
<212> TYPE: DNA
<213> ORGANISM: Mus musculus

<400> SEQUENCE: 218
tgcacagtgc t                                                    11

<210> SEQ ID NO 219
<211> LENGTH: 11
<212> TYPE: DNA
<213> ORGANISM: Mus musculus

<400> SEQUENCE: 219
tggatcagtc t                                                    11

<210> SEQ ID NO 220
<211> LENGTH: 11
<212> TYPE: DNA
<213> ORGANISM: Mus musculus

<400> SEQUENCE: 220
tggctcggtc a                                                    11

<210> SEQ ID NO 221
<211> LENGTH: 11
<212> TYPE: DNA
<213> ORGANISM: Mus musculus

<400> SEQUENCE: 221
tgtgccaagt g                                                    11

<210> SEQ ID NO 222
<211> LENGTH: 11
<212> TYPE: DNA
<213> ORGANISM: Mus musculus

<400> SEQUENCE: 222
ttctttggtg a                                                    11

<210> SEQ ID NO 223
<211> LENGTH: 11
<212> TYPE: DNA
<213> ORGANISM: Mus musculus

<400> SEQUENCE: 223
agtgaggaag a                                                    11

```
<210> SEQ ID NO 224
<211> LENGTH: 11
<212> TYPE: DNA
<213> ORGANISM: Mus musculus

<400> SEQUENCE: 224
caccttggtg c                                                         11

<210> SEQ ID NO 225
<211> LENGTH: 11
<212> TYPE: DNA
<213> ORGANISM: Mus musculus

<400> SEQUENCE: 225
ccctgagtcc a                                                         11

<210> SEQ ID NO 226
<211> LENGTH: 11
<212> TYPE: DNA
<213> ORGANISM: Mus musculus

<400> SEQUENCE: 226
ctaccactca a                                                         11

<210> SEQ ID NO 227
<211> LENGTH: 11
<212> TYPE: DNA
<213> ORGANISM: Mus musculus

<400> SEQUENCE: 227
ctgagagaga a                                                         11

<210> SEQ ID NO 228
<211> LENGTH: 11
<212> TYPE: DNA
<213> ORGANISM: Mus musculus

<400> SEQUENCE: 228
ctgtagactg c                                                         11

<210> SEQ ID NO 229
<211> LENGTH: 11
<212> TYPE: DNA
<213> ORGANISM: Mus musculus

<400> SEQUENCE: 229
ctgtaggtga t                                                         11

<210> SEQ ID NO 230
<211> LENGTH: 11
<212> TYPE: DNA
<213> ORGANISM: Mus musculus

<400> SEQUENCE: 230
cttgacacac a                                                         11

<210> SEQ ID NO 231
<211> LENGTH: 11
<212> TYPE: DNA
<213> ORGANISM: Mus musculus

<400> SEQUENCE: 231
gagtctccct g                                                         11
```

<210> SEQ ID NO 232
<211> LENGTH: 11
<212> TYPE: DNA
<213> ORGANISM: Mus musculus

<400> SEQUENCE: 232
gatgtggctg c                                                                 11

<210> SEQ ID NO 233
<211> LENGTH: 11
<212> TYPE: DNA
<213> ORGANISM: Mus musculus

<400> SEQUENCE: 233
gccgctaggc c                                                                 11

<210> SEQ ID NO 234
<211> LENGTH: 11
<212> TYPE: DNA
<213> ORGANISM: Mus musculus

<400> SEQUENCE: 234
gcctgtggcc t                                                                 11

<210> SEQ ID NO 235
<211> LENGTH: 11
<212> TYPE: DNA
<213> ORGANISM: Mus musculus

<400> SEQUENCE: 235
gcgccctccc c                                                                 11

<210> SEQ ID NO 236
<211> LENGTH: 11
<212> TYPE: DNA
<213> ORGANISM: Mus musculus

<400> SEQUENCE: 236
gggggcccag g                                                                 11

<210> SEQ ID NO 237
<211> LENGTH: 11
<212> TYPE: DNA
<213> ORGANISM: Mus musculus

<400> SEQUENCE: 237
gtgtgggcac t                                                                 11

<210> SEQ ID NO 238
<211> LENGTH: 11
<212> TYPE: DNA
<213> ORGANISM: Mus musculus

<400> SEQUENCE: 238
gtgttaacca g                                                                 11

<210> SEQ ID NO 239
<211> LENGTH: 11
<212> TYPE: DNA
<213> ORGANISM: Mus musculus

<400> SEQUENCE: 239
taaagaggcc g                                                                 11

-continued

<210> SEQ ID NO 240
<211> LENGTH: 11
<212> TYPE: DNA
<213> ORGANISM: Mus musculus

<400> SEQUENCE: 240
tgcttatgat g                                                         11

<210> SEQ ID NO 241
<211> LENGTH: 11
<212> TYPE: DNA
<213> ORGANISM: Mus musculus

<400> SEQUENCE: 241
tggtgacaaa a                                                         11

<210> SEQ ID NO 242
<211> LENGTH: 11
<212> TYPE: DNA
<213> ORGANISM: Mus musculus

<400> SEQUENCE: 242
tgtcagtctg t                                                         11

<210> SEQ ID NO 243
<211> LENGTH: 11
<212> TYPE: DNA
<213> ORGANISM: Mus musculus

<400> SEQUENCE: 243
ttcagctcga g                                                         11

<210> SEQ ID NO 244
<211> LENGTH: 11
<212> TYPE: DNA
<213> ORGANISM: Mus musculus

<400> SEQUENCE: 244
aacaatttgg g                                                         11

<210> SEQ ID NO 245
<211> LENGTH: 11
<212> TYPE: DNA
<213> ORGANISM: Mus musculus

<400> SEQUENCE: 245
aacaggttca a                                                         11

<210> SEQ ID NO 246
<211> LENGTH: 11
<212> TYPE: DNA
<213> ORGANISM: Mus musculus

<400> SEQUENCE: 246
aagcgcctca c                                                         11

<210> SEQ ID NO 247
<211> LENGTH: 11
<212> TYPE: DNA
<213> ORGANISM: Mus musculus

<400> SEQUENCE: 247

-continued aaggaaatgg g    11

<210> SEQ ID NO 248
<211> LENGTH: 11
<212> TYPE: DNA
<213> ORGANISM: Mus musculus

<400> SEQUENCE: 248
aaggtctgcc t    11

<210> SEQ ID NO 249
<211> LENGTH: 11
<212> TYPE: DNA
<213> ORGANISM: Mus musculus

<400> SEQUENCE: 249
aaggtggaag a    11

<210> SEQ ID NO 250
<211> LENGTH: 11
<212> TYPE: DNA
<213> ORGANISM: Mus musculus

<400> SEQUENCE: 250
acagttccag a    11

<210> SEQ ID NO 251
<211> LENGTH: 11
<212> TYPE: DNA
<213> ORGANISM: Mus musculus

<400> SEQUENCE: 251
accctcctcc c    11

<210> SEQ ID NO 252
<211> LENGTH: 11
<212> TYPE: DNA
<213> ORGANISM: Mus musculus

<400> SEQUENCE: 252
agaggaagct g    11

<210> SEQ ID NO 253
<211> LENGTH: 11
<212> TYPE: DNA
<213> ORGANISM: Mus musculus

<400> SEQUENCE: 253
agcagggatc c    11

<210> SEQ ID NO 254
<211> LENGTH: 11
<212> TYPE: DNA
<213> ORGANISM: Mus musculus

<400> SEQUENCE: 254
aggaaggcgg c    11

<210> SEQ ID NO 255
<211> LENGTH: 11
<212> TYPE: DNA
<213> ORGANISM: Mus musculus

<400> SEQUENCE: 255

-continued agggagcgct a                                                    11

<210> SEQ ID NO 256
<211> LENGTH: 11
<212> TYPE: DNA
<213> ORGANISM: Mus musculus

<400> SEQUENCE: 256
agtgactctg g                                                    11

<210> SEQ ID NO 257
<211> LENGTH: 11
<212> TYPE: DNA
<213> ORGANISM: Mus musculus

<400> SEQUENCE: 257
attctccagt g                                                    11

<210> SEQ ID NO 258
<211> LENGTH: 11
<212> TYPE: DNA
<213> ORGANISM: Mus musculus

<400> SEQUENCE: 258
atttgattag c                                                    11

<210> SEQ ID NO 259
<211> LENGTH: 11
<212> TYPE: DNA
<213> ORGANISM: Mus musculus

<400> SEQUENCE: 259
attttccagt g                                                    11

<210> SEQ ID NO 260
<211> LENGTH: 11
<212> TYPE: DNA
<213> ORGANISM: Mus musculus

<400> SEQUENCE: 260
caatgtgggt t                                                    11

<210> SEQ ID NO 261
<211> LENGTH: 11
<212> TYPE: DNA
<213> ORGANISM: Mus musculus

<400> SEQUENCE: 261
cacagactgt g                                                    11

<210> SEQ ID NO 262
<211> LENGTH: 11
<212> TYPE: DNA
<213> ORGANISM: Mus musculus

<400> SEQUENCE: 262
cacagcccac t                                                    11

<210> SEQ ID NO 263
<211> LENGTH: 11
<212> TYPE: DNA
<213> ORGANISM: Mus musculus -continued

<400> SEQUENCE: 263
caccgccagt g                                                          11

<210> SEQ ID NO 264
<211> LENGTH: 11
<212> TYPE: DNA
<213> ORGANISM: Mus musculus

<400> SEQUENCE: 264
cacggctttc a                                                          11

<210> SEQ ID NO 265
<211> LENGTH: 11
<212> TYPE: DNA
<213> ORGANISM: Mus musculus

<400> SEQUENCE: 265
cacgggacca c                                                          11

<210> SEQ ID NO 266
<211> LENGTH: 11
<212> TYPE: DNA
<213> ORGANISM: Mus musculus

<400> SEQUENCE: 266
cagtcaccaa c                                                          11

<210> SEQ ID NO 267
<211> LENGTH: 11
<212> TYPE: DNA
<213> ORGANISM: Mus musculus

<400> SEQUENCE: 267
cagtctctca a                                                          11

<210> SEQ ID NO 268
<211> LENGTH: 11
<212> TYPE: DNA
<213> ORGANISM: Mus musculus

<400> SEQUENCE: 268
ccaacgcttt a                                                          11

<210> SEQ ID NO 269
<211> LENGTH: 11
<212> TYPE: DNA
<213> ORGANISM: Mus musculus

<400> SEQUENCE: 269
ccacctcctg t                                                          11

<210> SEQ ID NO 270
<211> LENGTH: 11
<212> TYPE: DNA
<213> ORGANISM: Mus musculus

<400> SEQUENCE: 270
cccaggctga a                                                          11

<210> SEQ ID NO 271
<211> LENGTH: 11
<212> TYPE: DNA
<213> ORGANISM: Mus musculus

```
<400> SEQUENCE: 271
ccctaaactg a                                                            11

<210> SEQ ID NO 272
<211> LENGTH: 11
<212> TYPE: DNA
<213> ORGANISM: Mus musculus

<400> SEQUENCE: 272
ccctctacaa g                                                            11

<210> SEQ ID NO 273
<211> LENGTH: 11
<212> TYPE: DNA
<213> ORGANISM: Mus musculus

<400> SEQUENCE: 273
ccctgggttc t                                                            11

<210> SEQ ID NO 274
<211> LENGTH: 11
<212> TYPE: DNA
<213> ORGANISM: Mus musculus

<400> SEQUENCE: 274
ccctgtggcc g                                                            11

<210> SEQ ID NO 275
<211> LENGTH: 11
<212> TYPE: DNA
<213> ORGANISM: Mus musculus

<400> SEQUENCE: 275
cccttcttct c                                                            11

<210> SEQ ID NO 276
<211> LENGTH: 11
<212> TYPE: DNA
<213> ORGANISM: Mus musculus

<400> SEQUENCE: 276
ccgcctgcaa g                                                            11

<210> SEQ ID NO 277
<211> LENGTH: 11
<212> TYPE: DNA
<213> ORGANISM: Mus musculus

<400> SEQUENCE: 277
cctcagcctg g                                                            11

<210> SEQ ID NO 278
<211> LENGTH: 11
<212> TYPE: DNA
<213> ORGANISM: Mus musculus

<400> SEQUENCE: 278
cctcgcacag t                                                            11

<210> SEQ ID NO 279
<211> LENGTH: 11
<212> TYPE: DNA
```

<213> ORGANISM: Mus musculus

<400> SEQUENCE: 279
cctttaatcc c                                                    11

<210> SEQ ID NO 280
<211> LENGTH: 11
<212> TYPE: DNA
<213> ORGANISM: Mus musculus

<400> SEQUENCE: 280
cctttgtgac t                                                    11

<210> SEQ ID NO 281
<211> LENGTH: 11
<212> TYPE: DNA
<213> ORGANISM: Mus musculus

<400> SEQUENCE: 281
cgcctgctag c                                                    11

<210> SEQ ID NO 282
<211> LENGTH: 11
<212> TYPE: DNA
<213> ORGANISM: Mus musculus

<400> SEQUENCE: 282
ctgagagaaa a                                                    11

<210> SEQ ID NO 283
<211> LENGTH: 11
<212> TYPE: DNA
<213> ORGANISM: Mus musculus

<400> SEQUENCE: 283
ctgcctcaca g                                                    11

<210> SEQ ID NO 284
<211> LENGTH: 11
<212> TYPE: DNA
<213> ORGANISM: Mus musculus

<400> SEQUENCE: 284
ctgcgagatt c                                                    11

<210> SEQ ID NO 285
<211> LENGTH: 11
<212> TYPE: DNA
<213> ORGANISM: Mus musculus

<400> SEQUENCE: 285
ctgctttgtg c                                                    11

<210> SEQ ID NO 286
<211> LENGTH: 11
<212> TYPE: DNA
<213> ORGANISM: Mus musculus

<400> SEQUENCE: 286
ctgtctgaaa g                                                    11

<210> SEQ ID NO 287
<211> LENGTH: 11

-continued

```
<210> SEQ ID NO 287
<211> LENGTH: 11
<212> TYPE: DNA
<213> ORGANISM: Mus musculus

<400> SEQUENCE: 287
cttctcattt g                                                         11

<210> SEQ ID NO 288
<211> LENGTH: 11
<212> TYPE: DNA
<213> ORGANISM: Mus musculus

<400> SEQUENCE: 288
cttgctcaat g                                                         11

<210> SEQ ID NO 289
<211> LENGTH: 11
<212> TYPE: DNA
<213> ORGANISM: Mus musculus

<400> SEQUENCE: 289
cttggcgagc g                                                         11

<210> SEQ ID NO 290
<211> LENGTH: 11
<212> TYPE: DNA
<213> ORGANISM: Mus musculus

<400> SEQUENCE: 290
gaaagttggc c                                                         11

<210> SEQ ID NO 291
<211> LENGTH: 11
<212> TYPE: DNA
<213> ORGANISM: Mus musculus

<400> SEQUENCE: 291
gaacgcgacg g                                                         11

<210> SEQ ID NO 292
<211> LENGTH: 11
<212> TYPE: DNA
<213> ORGANISM: Mus musculus

<400> SEQUENCE: 292
gactttggaa a                                                         11

<210> SEQ ID NO 293
<211> LENGTH: 11
<212> TYPE: DNA
<213> ORGANISM: Mus musculus

<400> SEQUENCE: 293
gagttttcac g                                                         11

<210> SEQ ID NO 294
<211> LENGTH: 11
<212> TYPE: DNA
<213> ORGANISM: Mus musculus

<400> SEQUENCE: 294
gcacaacttg c                                                         11

<210> SEQ ID NO 295
```

-continued

<210> SEQ ID NO 295
<211> LENGTH: 11
<212> TYPE: DNA
<213> ORGANISM: Mus musculus

<400> SEQUENCE: 295
gcactgcgca c                                               11

<210> SEQ ID NO 296
<211> LENGTH: 11
<212> TYPE: DNA
<213> ORGANISM: Mus musculus

<400> SEQUENCE: 296
gcccccgcat a                                               11

<210> SEQ ID NO 297
<211> LENGTH: 11
<212> TYPE: DNA
<213> ORGANISM: Mus musculus

<400> SEQUENCE: 297
gcccctgcgc a                                               11

<210> SEQ ID NO 298
<211> LENGTH: 11
<212> TYPE: DNA
<213> ORGANISM: Mus musculus

<400> SEQUENCE: 298
gcctaatgta c                                               11

<210> SEQ ID NO 299
<211> LENGTH: 11
<212> TYPE: DNA
<213> ORGANISM: Mus musculus

<400> SEQUENCE: 299
gcctcctccc a                                               11

<210> SEQ ID NO 300
<211> LENGTH: 11
<212> TYPE: DNA
<213> ORGANISM: Mus musculus

<400> SEQUENCE: 300
gccttggtga a                                               11

<210> SEQ ID NO 301
<211> LENGTH: 11
<212> TYPE: DNA
<213> ORGANISM: Mus musculus

<400> SEQUENCE: 301
gcgaagctca g                                               11

<210> SEQ ID NO 302
<211> LENGTH: 11
<212> TYPE: DNA
<213> ORGANISM: Mus musculus

<400> SEQUENCE: 302
gcggcgccgc a                                               11

<210> SEQ ID NO 303
<211> LENGTH: 11
<212> TYPE: DNA
<213> ORGANISM: Mus musculus

<400> SEQUENCE: 303
gctctccagc a                                                          11

<210> SEQ ID NO 304
<211> LENGTH: 11
<212> TYPE: DNA
<213> ORGANISM: Mus musculus

<400> SEQUENCE: 304
gctgccctcc a                                                          11

<210> SEQ ID NO 305
<211> LENGTH: 11
<212> TYPE: DNA
<213> ORGANISM: Mus musculus

<400> SEQUENCE: 305
gctgtggcca c                                                          11

<210> SEQ ID NO 306
<211> LENGTH: 11
<212> TYPE: DNA
<213> ORGANISM: Mus musculus

<400> SEQUENCE: 306
ggcagccccc t                                                          11

<210> SEQ ID NO 307
<211> LENGTH: 11
<212> TYPE: DNA
<213> ORGANISM: Mus musculus

<400> SEQUENCE: 307
ggctgggggc t                                                          11

<210> SEQ ID NO 308
<211> LENGTH: 11
<212> TYPE: DNA
<213> ORGANISM: Mus musculus

<400> SEQUENCE: 308
gggcctgtgg g                                                          11

<210> SEQ ID NO 309
<211> LENGTH: 11
<212> TYPE: DNA
<213> ORGANISM: Mus musculus

<400> SEQUENCE: 309
ggtgccaact a                                                          11

<210> SEQ ID NO 310
<211> LENGTH: 11
<212> TYPE: DNA
<213> ORGANISM: Mus musculus

<400> SEQUENCE: 310 ggtgggggggg c                                                         11

<210> SEQ ID NO 311
<211> LENGTH: 11
<212> TYPE: DNA
<213> ORGANISM: Mus musculus

<400> SEQUENCE: 311
gtcacaggca a                                                           11

<210> SEQ ID NO 312
<211> LENGTH: 11
<212> TYPE: DNA
<213> ORGANISM: Mus musculus

<400> SEQUENCE: 312
gtctgcgtgc c                                                           11

<210> SEQ ID NO 313
<211> LENGTH: 11
<212> TYPE: DNA
<213> ORGANISM: Mus musculus

<400> SEQUENCE: 313
gtctgggggg a                                                           11

<210> SEQ ID NO 314
<211> LENGTH: 11
<212> TYPE: DNA
<213> ORGANISM: Mus musculus

<400> SEQUENCE: 314
gtctgtgccc a                                                           11

<210> SEQ ID NO 315
<211> LENGTH: 11
<212> TYPE: DNA
<213> ORGANISM: Mus musculus

<400> SEQUENCE: 315
gtgagcccat t                                                           11

<210> SEQ ID NO 316
<211> LENGTH: 11
<212> TYPE: DNA
<213> ORGANISM: Mus musculus

<400> SEQUENCE: 316
gtggcgcacg c                                                           11

<210> SEQ ID NO 317
<211> LENGTH: 11
<212> TYPE: DNA
<213> ORGANISM: Mus musculus

<400> SEQUENCE: 317
gtggctcaca g                                                           11

<210> SEQ ID NO 318
<211> LENGTH: 11
<212> TYPE: DNA
<213> ORGANISM: Mus musculus

<400> SEQUENCE: 318
gtgggtgttg g                                                           11

```
<210> SEQ ID NO 319
<211> LENGTH: 11
<212> TYPE: DNA
<213> ORGANISM: Mus musculus

<400> SEQUENCE: 319
tatctgtgca t                                                          11

<210> SEQ ID NO 320
<211> LENGTH: 11
<212> TYPE: DNA
<213> ORGANISM: Mus musculus

<400> SEQUENCE: 320
tattggctct g                                                          11

<210> SEQ ID NO 321
<211> LENGTH: 11
<212> TYPE: DNA
<213> ORGANISM: Mus musculus

<400> SEQUENCE: 321
tcactggccc c                                                          11

<210> SEQ ID NO 322
<211> LENGTH: 11
<212> TYPE: DNA
<213> ORGANISM: Mus musculus

<400> SEQUENCE: 322
tccaactcct t                                                          11

<210> SEQ ID NO 323
<211> LENGTH: 11
<212> TYPE: DNA
<213> ORGANISM: Mus musculus

<400> SEQUENCE: 323
tccctgtggt t                                                          11

<210> SEQ ID NO 324
<211> LENGTH: 11
<212> TYPE: DNA
<213> ORGANISM: Mus musculus

<400> SEQUENCE: 324
tccgggcgag g                                                          11

<210> SEQ ID NO 325
<211> LENGTH: 11
<212> TYPE: DNA
<213> ORGANISM: Mus musculus

<400> SEQUENCE: 325
tctcaccacc c                                                          11

<210> SEQ ID NO 326
<211> LENGTH: 11
<212> TYPE: DNA
<213> ORGANISM: Mus musculus

<400> SEQUENCE: 326
```
tctgccaatt t    11

<210> SEQ ID NO 327
<211> LENGTH: 11
<212> TYPE: DNA
<213> ORGANISM: Mus musculus

<400> SEQUENCE: 327
tctggacgcg g    11

<210> SEQ ID NO 328
<211> LENGTH: 11
<212> TYPE: DNA
<213> ORGANISM: Mus musculus

<400> SEQUENCE: 328
tcttctcaca a    11

<210> SEQ ID NO 329
<211> LENGTH: 11
<212> TYPE: DNA
<213> ORGANISM: Mus musculus

<400> SEQUENCE: 329
tgaaccgtcc c    11

<210> SEQ ID NO 330
<211> LENGTH: 11
<212> TYPE: DNA
<213> ORGANISM: Mus musculus

<400> SEQUENCE: 330
tgacagctgc c    11

<210> SEQ ID NO 331
<211> LENGTH: 11
<212> TYPE: DNA
<213> ORGANISM: Mus musculus

<400> SEQUENCE: 331
tgaccccggg c    11

<210> SEQ ID NO 332
<211> LENGTH: 11
<212> TYPE: DNA
<213> ORGANISM: Mus musculus

<400> SEQUENCE: 332
tgaccccggg t    11

<210> SEQ ID NO 333
<211> LENGTH: 11
<212> TYPE: DNA
<213> ORGANISM: Mus musculus

<400> SEQUENCE: 333
tgagcatcgg g    11

<210> SEQ ID NO 334
<211> LENGTH: 11
<212> TYPE: DNA
<213> ORGANISM: Mus musculus

<400> SEQUENCE: 334
tgcgtgctgg a                                                            11

<210> SEQ ID NO 335
<211> LENGTH: 11
<212> TYPE: DNA
<213> ORGANISM: Mus musculus

<400> SEQUENCE: 335
tggcccaaat t                                                            11

<210> SEQ ID NO 336
<211> LENGTH: 11
<212> TYPE: DNA
<213> ORGANISM: Mus musculus

<400> SEQUENCE: 336
tgtaacagga c                                                            11

<210> SEQ ID NO 337
<211> LENGTH: 11
<212> TYPE: DNA
<213> ORGANISM: Mus musculus

<400> SEQUENCE: 337
tgtaactggt c                                                            11

<210> SEQ ID NO 338
<211> LENGTH: 11
<212> TYPE: DNA
<213> ORGANISM: Mus musculus

<400> SEQUENCE: 338
tgtgaacttt g                                                            11

<210> SEQ ID NO 339
<211> LENGTH: 11
<212> TYPE: DNA
<213> ORGANISM: Mus musculus

<400> SEQUENCE: 339
tgttcatctt g                                                            11

<210> SEQ ID NO 340
<211> LENGTH: 11
<212> TYPE: DNA
<213> ORGANISM: Mus musculus

<400> SEQUENCE: 340
ttcagctcga a                                                            11

<210> SEQ ID NO 341
<211> LENGTH: 11
<212> TYPE: DNA
<213> ORGANISM: Mus musculus

<400> SEQUENCE: 341
ttctgtcctg t                                                            11

<210> SEQ ID NO 342
<211> LENGTH: 11
<212> TYPE: DNA
<213> ORGANISM: Mus musculus

```
-continued

<400> SEQUENCE: 342
ttgcaccttc t                                                              11

<210> SEQ ID NO 343
<211> LENGTH: 11
<212> TYPE: DNA
<213> ORGANISM: Mus musculus

<400> SEQUENCE: 343
ttgggccaga g                                                              11

<210> SEQ ID NO 344
<211> LENGTH: 11
<212> TYPE: DNA
<213> ORGANISM: Mus musculus

<400> SEQUENCE: 344
ttggtgaagg a                                                              11

<210> SEQ ID NO 345
<211> LENGTH: 11
<212> TYPE: DNA
<213> ORGANISM: Mus musculus

<400> SEQUENCE: 345
tttcgtgttg g                                                              11

<210> SEQ ID NO 346
<211> LENGTH: 11
<212> TYPE: DNA
<213> ORGANISM: Mus musculus

<400> SEQUENCE: 346
ttttccactt g                                                              11
```